(12) United States Patent
Francis et al.

(10) Patent No.: US 7,820,383 B2
(45) Date of Patent: Oct. 26, 2010

(54) METHOD FOR DIAGNOSING MYOCARDIAL INFARCTION

(75) Inventors: Sheila E. Francis, Sheffield (GB); David C. Crossman, Sheffield (GB); Gordon W. Duff, Sheffield (GB); Kenneth S. Kornman, Newton, MA (US); Katherine Martinez, San Antonio, TX (US)

(73) Assignee: Interleukin Genetics, Inc., Waltham, MA (US)

( * ) Notice: Subject to any disclaimer, the term of this patent is extended or adjusted under 35 U.S.C. 154(b) by 62 days.

(21) Appl. No.: 11/283,168

(22) Filed: Nov. 17, 2005

(65) Prior Publication Data

US 2006/0252055 A1 Nov. 9, 2006

Related U.S. Application Data

(63) Continuation-in-part of application No. 10/320,360, filed on Dec. 13, 2002, now abandoned, which is a continuation of application No. 09/431,352, filed on Nov. 1, 1999, now Pat. No. 6,524,795, which is a continuation-in-part of application No. 09/320,395, filed on May 26, 1999, now abandoned, which is a continuation-in-part of application No. 08/813,456, filed on Mar. 10, 1997, now Pat. No. 6,210,877.

(51) Int. Cl.
*C12Q 1/68* (2006.01)
*C07H 21/02* (2006.01)
*C07H 21/04* (2006.01)

(52) U.S. Cl. .................. 435/6; 536/23.5; 536/24.31

(58) Field of Classification Search ................. None
See application file for complete search history.

(56) References Cited

U.S. PATENT DOCUMENTS

| | | | | |
|---|---|---|---|---|
| 4,582,788 | A | 4/1986 | Erlich | 435/6 |
| 4,623,619 | A | 11/1986 | Owerbach et al. | 435/6 |
| 4,666,828 | A | 5/1987 | Gusella | 435/6 |
| 4,801,531 | A | 1/1989 | Frossard | 435/6 |
| 4,965,188 | A | 10/1990 | Mullis et al. | 435/6 |
| 4,968,607 | A | 11/1990 | Dower et al. | 435/69 |
| 5,110,920 | A | 5/1992 | Erlich | 536/27 |
| 5,268,267 | A | 12/1993 | Smith | 435/6 |
| 5,554,509 | A | 9/1996 | Collucci et al. | 435/6 |
| 5,658,729 | A | 8/1997 | Hayden et al. | 435/6 |
| 5,686,246 | A | 11/1997 | Kornman et al. | 435/6 |
| 5,698,399 | A | 12/1997 | Duff et al. | 435/6 |
| 6,140,047 | A | 10/2000 | Duff et al. | 435/6 |
| 6,210,877 | B1 | 4/2001 | Francis et al. | 435/6 |
| 6,268,142 | B1 | 7/2001 | Duff et al. | 435/6 |
| 6,524,795 | B1 | 2/2003 | Francis et al. | 435/6 |
| 6,706,478 | B2 | 3/2004 | Duff et al. | 435/6 |
| 6,720,141 | B1 | 4/2004 | Crossman et al. | 435/6 |
| 2003/0152947 | A1* | 8/2003 | Crossman et al. | 435/6 |

FOREIGN PATENT DOCUMENTS

| | | |
|---|---|---|
| AU | 738875 | 9/1998 |
| AU | 780318 | 12/2000 |
| AU | 782836 | 12/2000 |
| CA | 2282746 A1 | 9/1998 |
| CA | 2374916 A1 | 11/2000 |
| CN | 1255948 A | 6/2000 |
| DE | 0983381 T1 | 12/2007 |
| DE | 69838250 T2 | 5/2008 |
| EP | 0609059 A2 | 8/1994 |
| EP | 0269260 A2 | 1/1998 |
| EP | 1192279 B1 | 3/2008 |
| ES | 2156843 T1 | 8/2001 |
| ES | 2311459 | 2/2009 |
| WO | 9840517 | 9/1998 |
| WO | WO 98/40517 | 9/1998 |
| WO | 98/54359 | 12/1998 |
| WO | 00/71753 A2 | 11/2000 |
| WO | WO 00/72015 A2 | 11/2000 |
| WO | WO 02/103031 A2 | 12/2002 |
| WO | WO 03/044176 A2 | 5/2003 |
| WO | WO 2005/108619 A2 | 11/2005 |
| WO | 2007061906 A2 | 5/2007 |

OTHER PUBLICATIONS

Hirschhorn et al. Genetics in Medicine. 2002. 4(2): 45-61.*
Lucentini, J. The Scientist. Dec. 2004, p. 20.*
Halushka et al. Nature. Jul. 1999. 22: 239-247.*
Rosenmann et al. Neuroscience Letters. 2004. 363: 131-133.*
Francis et al. et al. Heart. 2001. 86: 336-340.*
Greestein et al. JADA. 2002. 133: 452-459.*
Lloyd-Jones et al. JAMA. May 2004. 291: 2204-2211.*
Alexander, R.W. *N.E.J.M.*, 331(7):468-469 (1994).
Anderson et al. *Am Heart J.*, 123(5):1312-1323 (1992).
Badimon et al. *Circulation (Suppl. II)*, 87(3):II3-II16 (1993).
Berger et al. *Cytokine.*, 17(4):171-174 (2002).
Clark et al. *Nucl. Acids Res.*, 14(20):7897-7914 (1986); Erratum in *Nucl. Acids Res.*, 15(2):868 (1987).
Clay et al. *Hum. Genet.*, 94:407-410 (1994).
Clay et al. *Hum. Genet.*, 97(6):723-726 (1996).
Cox et al. *Am. J. Hum. Genet.*, 62:1180-1188 (1998).

(Continued)

*Primary Examiner*—Carla Myers
(74) *Attorney, Agent, or Firm*—Mintz Levin Cohn Ferris Glovsky and Popeo, P.C.; Ivor R. Elrifi; Cynthia Kozakiewicz

(57) ABSTRACT

The kits and methods of the present invention relate to the diagnosis of cardiovascular disorders. In one aspect, the invention discloses a method and a kit for determining whether a subject has a fragile plaque disorder. In one aspect, the invention discloses a method and a kit for determining whether the subject has an occlusive disorder. In one aspect, the invention discloses a method and a kit for determining whether the subject has a restenosis disorder. Other methods of the present invention relate to the selection of therapeutics for a patient with a cardiovascular disease.

2 Claims, 14 Drawing Sheets

OTHER PUBLICATIONS

Di Giovine et al. *Hum. Mol. Genet.*, 1(6):450 (1992).
Dinarello et al. *JAMA*, 269(14):1829-1835 (1993).
Dinarello et al. *N.E.J.M.*, 328(2):106-113 (1993).
Duff *The Cytokine Handbook*, 2$^{nd}$ Ed., Chapter 2, pp. 21-30 (1994).
Eklund et al. *Eur. Cytokine Netw.*, 14(3):168-171 (2003).
Francis et al. *Circualtion*, 99(7):861 (1999).
Galea et al. *Ath. Thromb. Vasc. Biol.*, 16(8):1000-1006 (1996).
GenBank Accession No. X04500 (1997).
GenBank Accession No. X64532 (2004).
GenBank Accession No. X77090 (1996).
GenBank Accession No. Z17008 (1994).
GenBank Accession No. Z16545 (1994).
GIBCO BRL, *Product Catalog and Reference Guide*, pp. 18-15 to 18-16 (1995/1996).
Hall et al. *Arthritis Rheum.*, 50(6):1976-1983 (2004).
Hasdai et al. *Heart*, 76:24-28 (1996).
Iacoviello et al. *Arterioscler. Thromb. Vasc. Biol.*, 25:222-227 (2005).
Jaenisch, R. *PNAS*, 73(4):1260-1264 (1976).
Jähner et al. *Nature*, 298:623-628 (1982).
Jähner et al. *PNAS*, 82:6927-6931 (1985).
Knox *Houston Chronicle*, "Discovery May Help Battle Heart Attacks" (Jan. 10, 1996).
Kornman et al. *J. Periodont. Res.*, 34:353 (1999).
Latkovskis et al. *Eur. J. Immunogenet.*, 31(5):207-213 (2004).
Libby, P. *Circulation*, 91(11):2844-2850 (1995).
Liuzzo et al. *N.E.J.M.*, 33(7):417-424 (1994).
Mansfield et al. *Gastroenterol.*, 106(2):637-642 (1994).
McConnell et al. *Science*, 257:1906-1912 (1992).
Munro et al. *Lab. Invest.*, 58(3):249-261 (1988).
Nicklin et al. *Genomics*, 19:382-384 (1994).
Pankow et al. 71$^{st}$ EAS Congress and Satellite Symposia, p. 124 (1999).
Russell, R. *Nature*, 362:801-809 (1993).
Stewart et al. *EMBO J.*, 6(2):383-388 (1987).
Tarlow et al. *Hum. Genet.*, 91:403-404 (1993).
Tarlow et al. *J. Invest. Dermatol.*, 103:387-390 (1994).
Van der Putten et al. *PNAS*, 82:6148-6152 (1985).
Database GenBank (online), ss44355203, retrieved from GENBANK accession No. rs1143633, Abstract, Jul. 18, 2005.
Muraki et al, "Polymorphisms of IL-1μ Gene in Japanese Patients with Sjögren's Syndrome and Systemic Lupus Erythematosus", *J. Rheumatol.*, 31(4):720-725 (2004).
International Search Report for PCT/US2006/044793, mailed May 21, 2007.
Examination Report, Application No. EP 00937731.8, Date: Sep. 30, 2005.
Examination Report, Application No. EP 00937731.8, Date: Jan. 19, 2004.
Examination Report, Application No. EP 00939389.3, Date: Nov. 16, 2006.
Examination Report, Application No. EP 00939389.3, Date: Nov. 25, 2004.
Examination Report, Application No. EP 00939389.3, Date: Aug. 1, 2003.
Examination Report, Application No. EP 06837989.0, Date: Dec. 5, 2008.
Examination Report, Application No. EP 98910298.3, Date: Nov. 11, 2005.
Examination Report, Application No. EP 98910298.3, Date: Apr. 19, 2005.
Examination Report, Application No. EP 98910298.3, Date: Aug. 17, 2004.
Examination Report, Application No. EP 08015454.5, Date: May 25, 2009.
Blacmore et al. (1996), Interleukin-1 Receptor Antagonist Allele (IL1 RN*2) Associated with Nephropathy in Diabetes Mellitus, Hum. Genet, 97:369-374.
Kastrati et al., (2000), Protective Role Against Restenosis from an Interleukin-1 Receptor Antagonist Gene Polymorphism in Patients Treated With Coronary Stenting, J. Am. College of Cardiol. 36(7):2168-2173.
Kornman et al., (1999), Interleukin-1 Genotypes and the Association Between Periodontitis and Cardiovascular Disease, J. Periodont. Res., 34:353-357.
Muraki et al., (2004), Polymorphisms of IL-1 beta gene in Japanese Patients with Sjorgren's Syndrome and Systemic Lupus Erythematosus, J. of Rheumatol. 31(4):720-725.
Zee et al., (1999), Genetic Risk Factors for Post-PTCA Restenosis: A Comprehensive Analysis of Multiple Candidate Genes. J. of Am. Heart Assoc. Abstracts from the 72nd Scientific Session. Abstract 3985.
Databasee Genbank Accession No. rs1143633, Jul. 18, 2005.
Examination Report, Application No. EP 00937731.8, Date: Sep. 25, 2006.
Kastrati et al., (2000), Protection Against Restenosis From an Interleukin-1 Receptor Antagonist Gene Polymorphism in Patients Treated with Coronary Stenting, J. Am. College of Cardiol. 35(2):36A (Abstract).
Furutani et al. (1986), Nucleic Acid Research, 14:3167-3179.

* cited by examiner

CLINICAL TRIAL: GENETIC MARKER ASSOCIATED
WITH SYMPTOMATIC CORONARY ARTERY STENOSIS

- ALL PATIENTS PRESENTED WITH CHEST PAIN AND WERE EXAMINED BY ANGIOGRAPHY
- CONTROLS
  - N=85, MEAN AGE = 57.6 ± 10.4 YRS
  - ANGIOGRAPHICALLY NORMAL CORONARY ARTERIES
    - "NO OBVIOUS LUMENAL IRREGULARITIES"
- SINGLE VESSEL DISEASE
  - N=58, MEAN AGE = 56.4 ± 9.4 YRS
  - SINGLE VESSEL CORONARY ARTERY DISEASE
    - "1 OF 3 CORONARY VESSELS CONTAINED AN EPICARDIAL STENOSIS CAUSING >50% REDUCTION IN LUMENAL DIAMETER"
- MULTIPLE VESSEL DISEASE EXCLUDED BY DESIGN

Fig. 5

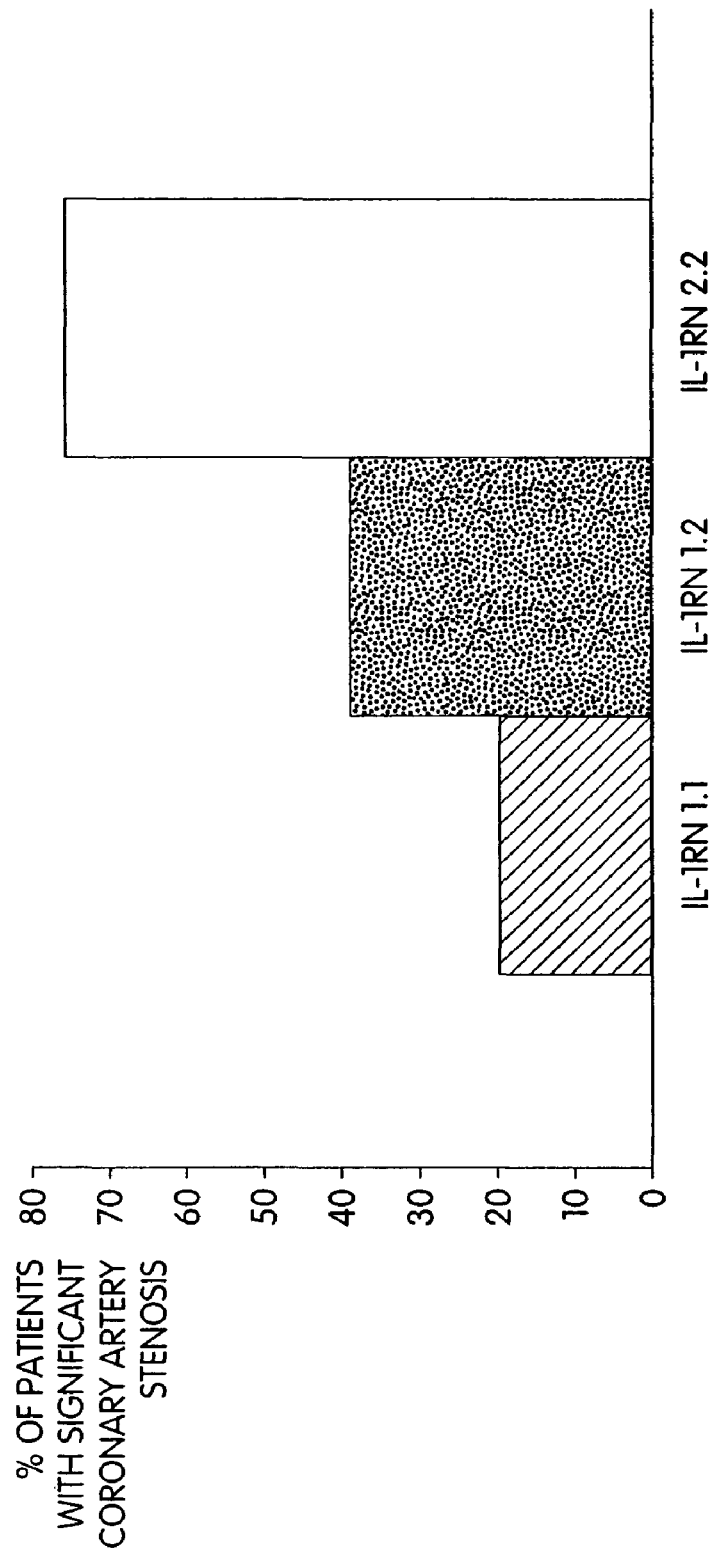

METHOD FOR DIAGNOSING MYOCARDIAL INFARCTION

RELATED U.S. APPLICATIONS

The present application is a continuation-in-part of U.S. application Ser. No. 10/320,360, filed Dec. 13, 2002, now abandoned, which is a continuation of U.S. application Ser. No. 09/431,352, filed Nov. 1, 1999, now U.S. Pat. No. 6,524, 795, which is a continuation-in-part of U.S. application Ser. No. 09/320,395, filed May 26, 1999, now abandoned, which is a continuation-in-part of U.S. application Ser. No. 08/813, 456, filed Mar. 10, 1997, now U.S. Pat. No. 6,210,877. The contents of these applications are hereby incorporated by reference in their entireties.

TECHNICAL FIELD

The present invention relates to kits and methods for the diagnosis and treatment of cardiovascular disorders, and more specifically to kits and methods related to diagnosis of disorders associated with IL-1 genotype patterns.

BACKGROUND OF THE INVENTION

Atherosclerosis (or arteriosclerosis) is the term used to describe progressive luminal narrowing and hardening of the arteries that can result in an aneurysm, ischemia, thrombosis, embolism formation or other vascular insufficiency. The disease process can occur in any systemic artery in the human body. For example, atherosclerosis in the arteries that supply the brain (e.g. the carotids, intracerebral, etc.,) can result in stroke. Gangrene may occur when the peripheral arteries are blocked, and coronary artery disease occurs when the arteries that supply oxygen and nutrients to the myocardium are affected.

Coronary artery disease is a multifactorial disease that results in the deposition of atheromatous plaque and progressive luminal narrowing of the arteries that supply the heart muscle. The atherosclerosis process involves lipid induced biological changes in the arterial walls resulting in a disruption of homeostatic mechanisms that keeps the fluid phase of the blood compartment separate from the vessel wall. Since the normal response to all injury is inflammation, the atherosclerotic lesion shows a complex chronic inflammatory response, including infiltration of mononuclear leukocytes, cell proliferation and migration, reorganization of extracellular matrix, and neovascularization. In fact, the atheromatous plaque consists of a mixture of inflammatory and immune cells, fibrous tissue, and fatty material such as low density lipids (LDL) and modifications thereof, and $\alpha$-lipoprotein. The luminal narrowing or blockage results in reduced ability to deliver oxygen and nutrients to the heart muscle, producing myocardial infarction, angina, unstable angina, and sudden ischemic death as heart failure. Though occlusion usually progresses slowly, blood supply may be cut off suddenly when a portion of the built-up arterial plaque breaks off and lodges somewhere in an artery to block it temporarily, or more usually, when thrombosis occurs within the arterial lumen. Rupture of the fibrous cap overlaying a vulnerable plaque is the most common cause of coronary thrombosis. Depending on the volume of muscle distal to the blockage during such an attack, a portion of the myocardial tissue may die, weakening the heart muscle and often leading to the death of the individual.

For many years, the most common measure of imminent risk for a heart disease "clinical event", such as a myocardial infarction or death, was physical blockage of the coronary arteries, as assessed by techniques such as angiography. During the early 80's studies by DeWood and coworkers (N. Engl. J. of Med. (1980) 303:1137-40), revealed that occlusive thrombus was responsible for most cases of acute myocardial infarction. At that time, the prevailing concept was that myocardial infarction resulted from occlusion at a site of high grade stenosis. In 1988, Little et al. (Circulation (1988) 78:1157-66), showed most of the infarctions resulted from a coronary blockage that had previously shown a stenosis of less than 50% on angiography. Therefore, the severity of the coronary stenosis did not accurately predict the location of a subsequent coronary blockage. With these studies the importance of vulnerable atherosclerotic plaque became evident.

It is now clear that rupture at the site of a vulnerable atherosclerotic plaque is the most frequent cause of acute coronary syndromes. Such plaque does not cause high grade stenosis, but may result in acute coronary syndrome, such as unstable angina, myocardial infarction, or sudden death. No methods are currently available that can reliably identify plaques prone to rupture. In fact, development of clinically useful imaging techniques for identifying vulnerable plaques is an active area of research. Some of the methods are being used to identify such plaques include for example, thermography (atherosclerotic plaques show thermal heterogeneity), spectroscopy (used to quantify the amount of cholesterol, cholesterol esters, triglycerides, phospholipids and calcium salts present in small volumes of the coronary arterial tissue), radioisotope scintigraphy (various constituents of vulnerable plaques such as inflammatory cells may be imaged with radioisotope techniques), and detection of inflammatory serum markers such as C-reactive protein levels.

Arterial sites that show acute plaque rupture are characterized by chronic inflammatory components that are not found, or are at much lower levels, in arterial plaques that are stable and unlikely to cause clinical events (Ross R. The pathogenesis of atherosclerosis: a perspective for the 1990s. Nature 1993; 362:801-809.) (Libby P. Molecular basis of the acute coronary syndromes. Circulation 1995; 91:2844-2850). The current published clinical data from many sources clearly demonstrate that various components of inflammation are strong independent influences on the severity and clinical outcomes of coronary artery disease (Ross R. The pathogenesis of atherosclerosis: a perspective for the 1990s. Nature 1993; 362:801-809.) (Libby P. Molecular basis of the acute coronary syndromes. Circulation 1995; 91:2844-2850). In addition, laboratory work has shown that pro-inflammatory mediators are critical elements in the atherosclerosis process (Ross R. The pathogenesis of atherosclerosis: a perspective for the 1990s. Nature 1993; 362:801-809.) (Libby P. Molecular basis of the acute coronary syndromes. Circulation 1995; 91:2844-2850).

The causes and mechanisms of the atheromatous plaque build-up are not completely understood, though many theories exist. One theory on the pathogenesis of atherosclerosis involves the following stages: (1) endothelial cell dysfunction and/or injury, (2) monocyte recruitment and macrophage formation, (3) lipid deposition and modification, (4) vascular smooth muscle cell proliferation, and (5) synthesis of extracellular matrix. According to this theory, the initiation of atherosclerosis is potentially due to a form of injury, possibly from mechanical stress or from chemical stress. How the body responds to this injury then defines whether, and how rapidly, the injury deteriorates into an atherosclerotic lesion. This, in turn, can result in arterial luminal narrowing and damage to the heart tissue which depends on the blood flow of oxygen and nutrients.

For many years, epidemiologic studies have indicated that an individual's genetic composition is a significant risk factor for development of a vascular disease. For example, a family history of heart disease is associated with an increased individual risk of developing coronary artery disease. Lipid and cholesterol metabolism have historically been considered the primary genetic influence on coronary artery disease. For example, deficiency in cell receptors for low-density lipids (LDL), such as in familial hypercholesterolemia, is associated with high levels of plasma LDL and premature development of atherosclerosis (Brown & Goldstein, *Sci.*, 191 (4223):150-4 (1976)).

Inflammation is now generally regarded as an important component of the pathogenic process of atherosclerosis (Munro, *Lab Invest.*, 58:249-261 (1988); Badimon, et al., *Circulation*, 87:3-16 (1993); Liuzzo, et al., *N.E.J.M.*, 331(7):417-24 (1994); Alexander, *N.E.J.M.*, 331(7):468-9 (1994)). Damage to endothelial cells that line the vessels leads to an accumulation of inflammatory cytokines, including IL-1, TNFα, and the release of prostanoids and growth factors such as prostaglandin $I_2$ ($PGI_2$), platelet-derived growth factor (PDGF), basic fibroblast growth factor (bFGF), and granulocyte-monocyte cell stimulating factor (GM-CSF). These factors lead to accumulation and regulation of inflammatory cells, such as monocytes, that accumulate within the vessel walls. The monocytes then release additional inflammatory mediators, including IL-1, TNF, prostaglandin $E_2$, ($PGE_2$), bFGF, and transforming growth factors α and β (TGFα, TGFβ). All of these inflammatory mediators recruit more inflammatory cells to the damaged area, regulate the behavior of endothelial and smooth muscle cells and lead to the accumulation of atheromatous plaques.

Several inflammatory products, including IL-1β, have been identified in atherosclerotic lesions or in the endothelium of diseased coronary arteries (Galea, et al., *Ath. Thromb. Vasc. Biol.*, 16:1000-6 (1996)). Also, serum concentrations of IL-1β have been found to be elevated in patients with coronary disease (Hasdai, et al., *Heart*, 76:24-8 (1996)). Although it was historically believed that the presence of inflammatory agents was responsive to injury or monocyte activation, it is also possible that an abnormal inflammatory response may be causative of coronary artery disease or create an increased susceptibility to the disease.

A key problem in treating vascular diseases is proper diagnosis. Often the first sign of the disease is sudden death. For example, approximately half of all individuals who die of coronary artery disease die suddenly, Furthermore, for 40-60% of the patients who are eventually diagnosed as having coronary artery disease, myocardial infarction is the first presentation of the disease. Unfortunately, approximately 40% of those initial events go unnoticed by the patient. It is now believed that, identification and stabilization of vulnerable plaques is an important element in the treatment of coronary atherosclerosis. Identification of the haplotype patterns in various subjects would allow in the management of cardiovascular disorders and treatment could be aimed at plaque stabilization rather than revascularization and other more invasive methods. This is especially important, because, for various reasons, the perception of symptoms by the patient does not correlate well with the total burden of coronary artery disease (Anderson & Kin, *Am. Heart J.*, 123(5): 1312-23 (1992)).

Percutaneous transluminal coronary angioplasty (PTCA) is used to treat obstructive coronary artery disease by compressing atheromatous plaque to the sides of the vessel wall. PTCA is widely used with an initial success rate of over 90%. However, the long-term success of PTCA is limited by intraluminal renarrowing or restenosis at the site of the procedure. This occurs within 6 months following the procedure in approximately 30% to 40% of patients who undergo a single vessel procedure and in more than 50% of those who undergo multivessel angioplasty.

Stent placement has largely supplanted balloon angioplasty because it is able to more widely restore intraluminal dimensions which has the effect of reducing restenosis by approximately 50%. Ironically, stent placement actually increases neointimal growth at the treatment site, but because a larger lumen can be achieved with stent placement, the tissue growth is more readily accommodated, and sufficient luminal dimensions are maintained, so that the restenosis rate is nearly halved by stent placement compared with balloon angioplasty alone.

The pathophysiological mechanisms involved in restenosis are not fully understood. While a number of clinical, anatomical and technical factors have been linked to the development of restenosis, at least 50% of the process has yet to be explained. However, it is known that following endothelial injury, a series of repair mechanisms are initiated. Within minutes of the injury, a layer of platelets and fibrin is deposited over the damaged endothelium. Within hours to days, inflammatory cells begin to infiltrate the injured area. Within 24 hours after an injury, vascular smooth muscle cells (SMCs) located in the vessel media commence DNA synthesis. A few days later, these activated, synthetic SMCs migrate through the internal elastic lamina towards the luminal surface. A neointima is formed by these cells by their continued replication and their production of extracellular matrix. An increase in the intimal thickness occurs with ongoing cellular proliferation matrix deposition. When these processes of vascular healing progress excessively, the pathological condition is termed intimal hyperplasia or myointimal hyperplasia. The biology of vascular wall healing implicated in restenosis therefore includes the general processes of wound healing and the specific processes of myointimal hyperplasia. Inflammation is generally regarded as an important component in both these processes. (Munro and Cotran (1993) Lab. Investig. 58:249-261; and Badimon et al. (1993), Supp II 87:3-6). Understanding the effects of acute and chronic inflammation in the blood vessel wall can thus suggest methods for diagnosing and treating restenosis and related conditions.

In its initial phase, inflammation is characterized by the adherence of leukocytes to the vessel wall. Leukocyte adhesion to the surface of damaged endothelium is mediated by several complex glycoproteins on the endothelial and neutrophil surfaces. Two of these binding molecules have been well-characterized: the endothelial leukocyte adhesion molecule-1 (ELAM-1) and the intercellular adhesion molecule-1 (ICAM-1). During inflammatory states, the attachment of neutrophils to the involved cell surfaces is greatly increased, primarily due to the upregulation and enhanced expression of these binding molecules. Substances thought to be primary mediators of the inflammatory response to tissue injury, including interleukin-1 (IL-1), tumor necrosis factor alpha (TNF), lymphotoxin and bacterial endotoxins, all increase the production of these binding substances.

After binding to the damaged vessel wall, leukocytes migrate into it. Once in place within the vessel wall, the leukocytes, in particular activated macrophages, then release additional inflammatory mediators, including IL-1, TNF, prostaglandin $E_2$, ($PGE_2$), bFGF, and transforming growth factors α and β (TGFα, TGFβ). All of these inflammatory mediators recruit more inflammatory cells to the damaged area, and regulate the further proliferation and migration of smooth muscle. A well-known growth factor elaborated by the monocyte-macrophage is monocyte- and macrophage-derived growth factor (MDGF), a stimulant of smooth muscle cell and fibroblast proliferation. MDGF is understood to be similar to platelet-derived growth factor (PDGF); in fact, the two substances may be identical. By stimulating smooth muscle cell proliferation, inflammation can contribute to the development and the progression of myointimal hyperplasia.

Leukocytes, attracted to the vessel wall by the abovementioned chemical mediators of inflammation, produce substances that have direct effects on the vessel wall that may exacerbate the local injury and prolong the healing response. First, leukocytes activated by the processes of inflammation secrete lysosomal enzymes that can digest collagen and other structural proteins. Releasing these enzymes within the vessel wall can affect the integrity of its extracellular matrix, permitting SMCs and other migratory cells to pass through the wall more readily. Hence, the release of these lysosomal proteases can enhance the processes leading to myointimal hyperplasia. Second, activated leukocytes produce free radicals by the action of the NADPH system on their cell membranes. These free radicals can damage cellular elements directly, leading to an extension of a local injury or a prolongation of the cycle of injury-inflammation-healing.

It would be desirable to determine which patients would respond well to invasive treatments for occlusive vascular disease such as angioplasty and intravascular stent placement. It would be further desirable to identify those patients at increased risk for stenosis so that they could be targeted with appropriate therapies to prevent, modulate or reverse the condition. It would be desirable, moreover, to identify those individuals for whom PTCA and stent placement is a suboptimal therapeutic choice because of the risk of restenosis. Those patients might become candidates at earlier stages for vascular reconstructive procedures, possibly combined with other pharmacological interventions.

Genetics of the IL-1 Gene Cluster

The IL-1 gene cluster is on the long arm of chromosome 2 (2q13) and contains at least the genes for IL-1α (IL-1A), IL-1β (IL-1B), and the IL-1 receptor antagonist (IL-1RN), within a region of 430 Kb (Nicklin, et al. (1994) Genomics, 19: 382-4). The agonist molecules, IL-1α and IL-1β, have potent pro-inflammatory activity and are at the head of many inflammatory cascades. Their actions, often via the induction of other cytokines such as IL-6 and IL-8, lead to activation and recruitment of leukocytes into damaged tissue, local production of vasoactive agents, fever response in the brain and hepatic acute phase response. All three IL-1 molecules bind to type I and to type II IL-1 receptors, but only the type I receptor transduces a signal to the interior of the cell. In contrast, the type II receptor is shed from the cell membrane and acts as a decoy receptor. The receptor antagonist and the type II receptor, therefore, are both anti-inflammatory in their actions.

Inappropriate production of IL-1 plays a central role in the pathology of many autoimmune and inflammatory diseases, including rheumatoid arthritis, inflammatory bowel disorder, psoriasis, and the like. In addition, there are stable interindividual differences in the rates of production of IL-1, and some of this variation may be accounted for by genetic differences at IL-1 gene loci. Thus, the IL-1 genes are reasonable candidates for determining part of the genetic susceptibility to inflammatory diseases, most of which have a multifactorial etiology with a polygenic component.

Certain alleles from the IL-1 gene cluster are known to be associated with particular disease states. For example, IL-1RN (VNTR) allele 2 has been shown to be associated with osteoporosis (U.S. Pat. No. 5,698,399), nephropathy in diabetes mellitus (Blakemore, et al. (1996) Hum. Genet. 97(3): 369-74), alopecia greata (Cork, et al., (1995) J. Invest. Dermatol. 104(5 Supp.): 15S-16S; Cork et al. (1996) Dermatol Clin 14: 671-8), Graves disease (Blakemore, et al. (1995) J. Clin. Endocrinol. 80(1): 111-5), systemic lupus erythematosus (Blakemore, et al. (1994) Arthritis Rheum. 37: 1380-85), lichen sclerosis (Clay, et al. (1994) Hum. Genet. 94: 407-10), and ulcerative colitis (Mansfield, et al. (1994) Gastoenterol. 106(3): 637-42)).

In addition, the IL-1A allele 2 from marker-889 and IL-1B (TaqI) allele 2 from marker +3954 have been found to be associated with periodontal disease (U.S. Pat. No. 5,686,246; Kornman and diGiovine (1998) Ann Periodont 3: 327-38; Hart and Kornman (1997) Periodontol 2000 14: 202-15; Newman (1997) Compend Contin Educ Dent 18: 881-4; Kornman et al. (1997) J. Clin Periodontol 24: 72-77). The IL-1A allele 2 from marker −889 has also been found to be associated with juvenile chronic arthritis, particularly chronic iridocyclitis (McDowell, et al. (1995) Arthritis Rheum. 38: 221-28). The IL-1B (TaqI) allele 2 from marker +3954 of IL-1B has also been found to be associated with psoriasis and insulin dependent diabetes in DR3/4 patients (di Giovine, et al. (1995) Cytokine 7: 606; Pociot, et al. (1992) Eur J. Clin. Invest. 22: 396-402). Additionally, the IL-1RN (VNTR) allele 1 has been found to be associated with diabetic retinopathy (see U.S. Ser. No. 09/037,472, and PCT/GB97/02790). Furthermore allele 2 of IL-1RN (VNTR) has been found to be associated with ulcerative colitis in Caucasian populations from North America and Europe (Mansfield, J. et al., (1994) Gastroenterology 106: 637-42). Interestingly, this association is particularly strong within populations of ethnically related Ashkenazi Jews (PCT WO97/25445).

Genotype Screening

Traditional methods for the screening of heritable diseases have depended on either the identification of abnormal gene products (e.g., sickle cell anemia) or an abnormal phenotype (e.g., mental retardation). These methods are of limited utility for heritable diseases with late onset and no easily identifiable phenotypes such as, for example, vascular disease. With the development of simple and inexpensive genetic screening methodology, it is now possible to identify polymorphisms that indicate a propensity to develop disease, even when the disease is of polygenic origin. The number of diseases that can be screened by molecular biological methods continues to grow with increased understanding of the genetic basis of multifactorial disorders.

Genetic screening (also called genotyping or molecular screening), can be broadly defined as testing to determine if a patient has mutations (or alleles or polymorphisms) that either cause a disease state or are "linked" to the mutation causing a disease state. Linkage refers to the phenomenon wherein DNA sequences which are close together in the genome have a tendency to be inherited together. Two sequences may be linked because of some selective advantage of co-inheritance. More typically, however, two polymorphic sequences are co-inherited because of the relative infrequency with which meiotic recombination events occur within the region between the two polymorphisms. The co-inherited polymorphic alleles are said to be in linkage disequilibrium with one another because, in a given human population, they tend to either both occur together or else not occur at all in any particular member of the population. Indeed, where multiple polymorphisms in a given chromosomal region are found to be in linkage disequilibrium with one another, they define a quasi-stable genetic "haplotype." In contrast, recombination events occurring between two polymorphic loci cause them to become separated onto distinct homologous chromosomes. If meiotic recombination between two physically linked polymorphisms occurs frequently enough, the two polymorphisms will appear to segregate independently and are said to be in linkage equilibrium.

While the frequency of meiotic recombination between two markers is generally proportional to the physical distance between them on the chromosome, the occurrence of "hot spots" as well as regions of repressed chromosomal recombination can result in discrepancies between the physical and recombinational distance between two markers. Thus, in certain chromosomal regions, multiple polymorphic loci spanning a broad chromosomal domain may be in linkage disequilibrium with one another, and thereby define a broad-spanning genetic haplotype. Furthermore, where a disease-causing mutation is found within or in linkage with this haplotype, one or more polymorphic alleles of the haplotype can be used as a diagnostic or prognostic indicator of the likelihood of developing the disease. This association between otherwise benign polymorphisms and a disease-causing polymorphism occurs if the disease mutation arose in the recent past, so that sufficient time has not elapsed for equilibrium to be achieved through recombination events. Therefore identification of a human haplotype which spans or is linked to a disease-causing mutational change, serves as a predictive measure of an individual's likelihood of having inherited that disease-causing mutation. Importantly, such prognostic or diagnostic procedures can be utilized without necessitating the identification and isolation of the actual disease-causing lesion. This is significant because the precise determination of the molecular defect involved in a disease process can be difficult and laborious, especially in the case of multifactorial diseases such as inflammatory disorders.

Indeed, the statistical correlation between an inflammatory disorder and an IL-1 polymorphism does not necessarily indicate that the polymorphism directly causes the disorder. Rather the correlated polymorphism may be a benign allelic variant which is linked to (i.e. in linkage disequilibrium with) a disorder-causing mutation which has occurred in the recent human evolutionary past, so that sufficient time has not elapsed for equilibrium to be achieved through recombination events in the intervening chromosomal segment. Thus, for the purposes of diagnostic and prognostic assays for a particular disease, detection of a polymorphic allele associated with that disease can be utilized without consideration of whether the polymorphism is directly involved in the etiology of the disease. Furthermore, where a given benign polymorphic locus is in linkage disequilibrium with an apparent disease-causing polymorphic locus, still other polymorphic loci which are in linkage disequilibrium with the benign polymorphic locus are also likely to be in linkage disequilibrium with the disease-causing polymorphic locus. Thus these other polymorphic loci will also be prognostic or diagnostic of the likelihood of having inherited the disease-causing polymorphic locus. Indeed, a broad-spanning human haplotype (describing the typical pattern of co-inheritance of alleles of a set of linked polymorphic markers) can be targeted for diagnostic purposes once an association has been drawn between a particular disease or condition and a corresponding human haplotype. Thus, the determination of an individual's likelihood for developing a particular disease of condition can be made by characterizing one or more disease-associated polymorphic alleles (or even one or more disease-associated haplotypes) without necessarily determining or characterizing the causative genetic variation.

SUMMARY OF THE INVENTION

In one aspect, the present invention provides novel methods and kits for determining whether a subject has a cardiovascular disorder. In one embodiment, the kits and methods of the present invention are directed to the diagnosis of fragile plaque disorder. Diagnosis of the presence of fragile plaque disorder identifies those patients predisposed to the development of fragile plaque disease, characterized by clinical events such as myocardial infarction and stroke. Diagnosing these individuals predisposed to the development of fragile plaque disease is especially important because the onset of the disease can be abrupt and catastrophic, without premonitory signs and symptoms. Determining which patients are at risk for developing the disease because they have the disorder thus opens the possibility of early diagnosis of disease conditions and treating the disorder and the disease through appropriate therapeutics.

In another embodiment, the kits and methods of the present invention are directed to the diagnosis of an occlusive disorder. Diagnosis of the presence of an occlusive disorder identifies those patients predisposed to the development of occlusive disease, characterized by clinical events such as ischemia, angina, claudication, rest pain and gangrene. Determining which patients are at risk for developing the disease because they have the disorder thus opens the possibility of early diagnosis and therapeutic intervention, at a stage before irreversible tissue changes have occurred in the tissues served by the affected vessels.

In yet another embodiment, the kits and methods of the present invention are directed to the diagnosis of a restenosis disorder. Diagnosis of the presence of a restenosis disorder identifies those patients predisposed to the development of a restenosis disease, characterized by clinical events related to the recurrence of the initial vascular stenosis that is being treated by the stent. Determining which patients are at risk for developing the disease because they have the disorder thus opens the possibility of selecting therapies for the initial vascular stenosis most likely to avoid subsequent stenoses. Such patients might be candidates for surgical revascularization rather than percutaneous transluminal angioplasty, for example, or such patients may benefit from pharmacological or topical interventions at an early stage that could affect the progression of the restenosis disorder.

In another aspect, the methods of the present invention provide for the treatment of a patient with a cardiovascular disorder of the abovementioned types. Treatment includes determining whether a patient has an allelic pattern associated with a cardiovascular disorder and administering to the patient a therapeutic adapted to the treatment of the cardiovascular disorder. In one embodiment, the method can include the identification of a risk factor for the cardiovascular disorder and the formulation of a treatment plan that reduces the effect of the risk factor on the patient.

These and other embodiments of the present invention rely at least in part upon the novel finding that there is an association of patterns of alleles at four polymorphic loci in the IL-1 gene cluster with cardiovascular disorders. These patterns are referred to herein patterns 1, 2 and 3. Pattern 1 comprises an allelic pattern including allele 2 of IL-1A (+4845) or IL-1B (+3954) and allele 1 of IL-1B (−511) or IL-1RN (+2018), or an allele that is in linkage disequilibrium with one of the aforementioned allele. In a preferred embodiment, this allelic pattern permits the diagnosis of fragile plaque disorder. Pattern 2 comprises an allelic pattern including allele 2 of IL-1B (−511) or IL-1RN (+2018) and allele 1 of IL-1A (+4845) or IL-1B (+3954), or an allele that is in linkage disequilibrium with one of the aforementioned alleles. In a preferred embodiment, this allelic pattern permits the diagnosis of fragile plaque disorder. Pattern 3 comprises an allelic pattern including allele 1 of IL-1A (+4845) or allele 1 of IL-1B (+3954), and allele 1 of IL-1B (−511) or allele 1 of IL-1RN (+2018), or an allele that is in linkage disequilibrium with one of the aforementioned alleles. In a preferred embodiment, this allelic pattern permits the diagnosis of a restenosis disorder.

An allele associated with a cardiovascular disorder can be detected by any of a variety of available techniques, including: 1) performing a hybridization reaction between a nucleic acid sample and a probe that is capable of hybridizing to the allele; 2) sequencing at least a portion of the allele; or 3) determining the electrophoretic mobility of the allele or fragments thereof (e.g., fragments generated by endonuclease digestion). The allele can optionally be subjected to an amplification step prior to performance of the detection step. Preferred amplification methods are selected from the group consisting of: the polymerase chain reaction (PCR), the ligase chain reaction (LCR), strand displacement amplification (SDA), cloning, and variations of the above (e.g. RT-PCR and allele specific amplification). Oligonucleotides necessary for amplification may be selected for example, from within the IL-1 gene loci, either flanking the marker of interest (as required for PCR amplification) or directly overlapping the marker (as in ASO hybridization). In a particularly preferred embodiment, the sample is hybridized with a set of primers, which hybridize 5' and 3' in a sense or antisense sequence to the vascular disease associated allele, and is subjected to a PCR amplification.

An allele associated with a cardiovascular disorder may also be detected indirectly, e.g. by analyzing the protein product encoded by the DNA. For example, where the marker in question results in the translation of a mutant protein, the protein can be detected by any of a variety of protein detection methods. Such methods include immunodetection and biochemical tests, such as size fractionation, where the protein has a change in apparent molecular weight either through truncation, elongation, altered folding or altered post-translational modifications.

In another aspect, the invention features kits for performing the above-described assays. The kit can include a nucleic acid sample collection means and a means for determining whether a subject carries a cardiovascular disorder associated allele. The kit may also contain a control sample either positive or negative or a standard and/or an algorithmic device for assessing the results and additional reagents and components including: DNA amplification reagents, DNA polymerase, nucleic acid amplification reagents, restrictive enzymes, buffers, a nucleic acid sampling device, DNA purification device, deoxynucleotides, oligonucleotides (e.g. probes and primers) etc.

As described above, the control samples may be positive or negative controls. Further, the control sample may contain the positive (or negative) products of the allele detection technique employed. For example, where the allele detection technique is PCR amplification, followed by size fractionation, the control sample may comprise DNA fragments of the appropriate size. Likewise, where the allele detection technique involves detection of a mutated protein, the control sample may comprise a sample of mutated protein. However, it is preferred that the control sample comprises the material to be tested. For example, the controls may be a sample of genomic DNA or a cloned portion of the IL-1 gene cluster. Preferably, however, the control sample is a highly purified sample of genomic DNA where the sample to be tested is genomic DNA.

The oligonucleotides present in said kit may be used for amplification of the region of interest or for direct allele specific oligonucleotide (ASO) hybridization to the markers in question. Thus, the oligonucleotides may either flank the marker of interest (as required for PCR amplification) or directly overlap the marker (as in ASO hybridization).

Information obtained using the assays and kits described herein (alone or in conjunction with information on a risk factor, such as a concurrent disease, a genetic defect or environmental factor which contributes to a vascular disorder) is useful for determining whether a non-symptomatic subject has a cardiovascular disorder or is likely to develop a cardiovascular disease. In addition, the information can allow a more customized approach and allow one to determine whether the course of action should involve the use of more invasive procedures or whether treatment should be aimed at plaque stabilization. This information can enable a clinician to more effectively prescribe a therapy that will address the molecular or genetic basis of the disorder.

In a further aspect, the invention features methods for treating or preventing the development of a cardiovascular disorder in a subject by administering to the subject an appropriate therapeutic of the invention. In still another aspect, the invention provides in vitro or in vivo assays for screening test compounds to identify therapeutics for treating or preventing a cardiovascular disorder. In one embodiment, the assay comprises contacting a cell transfected with a causative mutation that is operably linked to an appropriate promoter with a test compound and determining the level of expression of a protein in the cell in the presence and in the absence of the test compound. In one embodiment, the causative mutation affects the systemic levels of IL-1 receptor antagonist, and is associated with increased serum levels of IL-1RA, so that the therapeutic efficacy of a particular compound can be gauged by whether serum levels of IL-1RA fall in its presence. In another preferred embodiment, if the cardiovascular disorder causative mutation results in increased production of IL-1α or IL-1β, and decreased production of IL-1α or IL-1β in the presence of the test compound indicates that the compound is an antagonist of IL-1α or IL-1β activity. In another embodiment, the invention features transgenic non-human animals and their use in identifying antagonists of IL-1α or IL-1β activity or agonists of IL-1Ra activity.

Other features and advantages of the invention are set forth in the following detailed description and claims.

BRIEF DESCRIPTION OF THE FIGURES

FIG. 5 shows features of a clinical trial related to genetic markers.

FIG. 6 presents a bar graph of the association between an IL-1 genotype and coronary artery stenosis.

DETAILED DESCRIPTION OF THE INVENTION

4.1 Definitions

Figure 1:
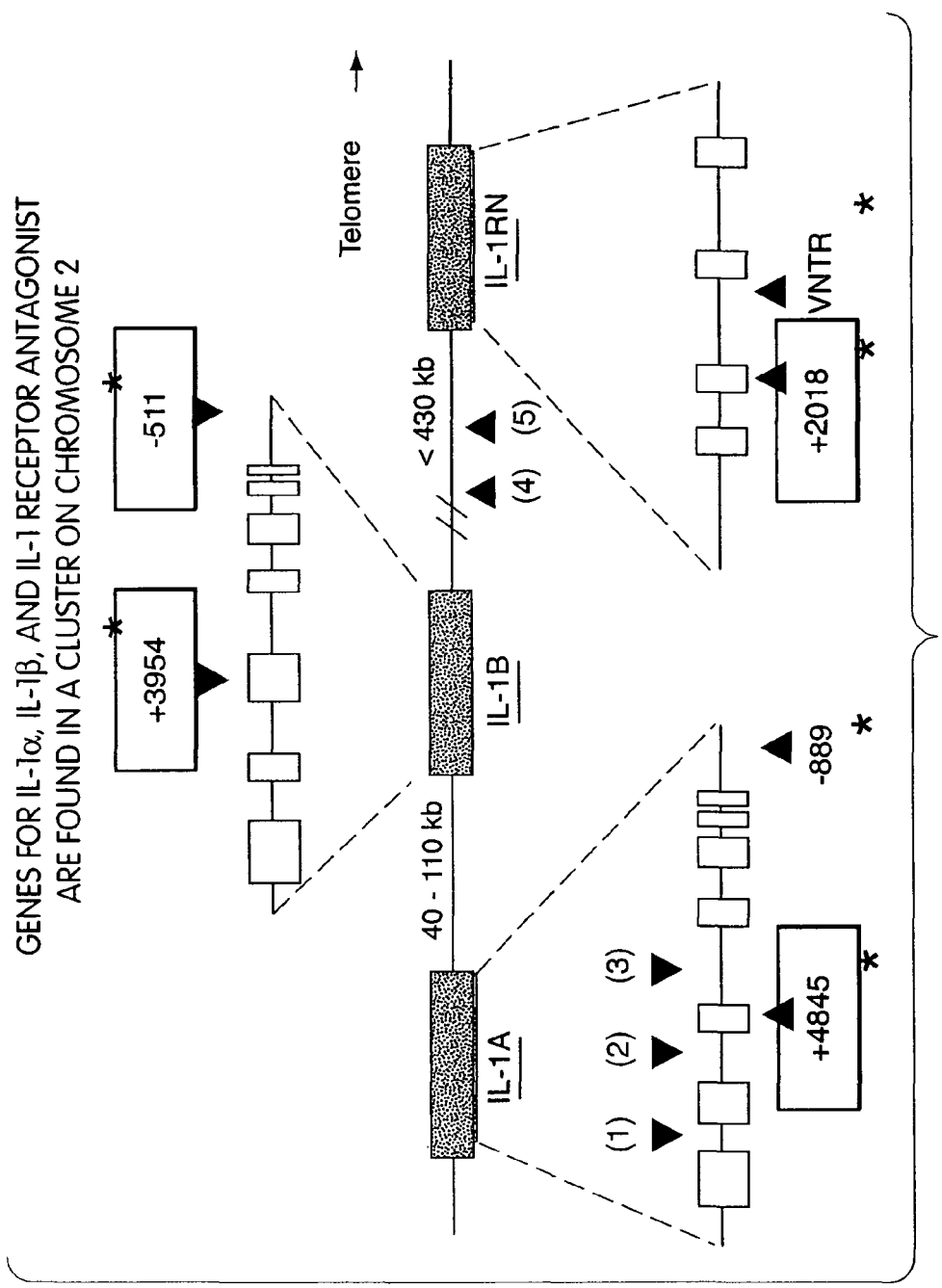
FIG. 1 depicts schematically a position of genes on Chromosome 2.

For convenience, the meaning of certain terms and phrases employed in the specification, examples, and appended claims are provided below.

The term "aberrant activity", as applied to an activity of a polypeptide such as IL-1, refers to an activity which differs from the activity of a native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example an aberrant polypeptide can interact with a different target peptide. A cell can have an aberrant IL-1 activity due to overexpression or underexpression of an IL-1 locus gene encoding an IL-1 locus polypeptide.

The term "allele" refers to the different sequence variants found at different polymorphic regions. For example, IL-1RN (VNTR) has at least five different alleles. The sequence variants may be single or multiple base changes, including without limitation insertions, deletions, or substitutions, or may be a variable number of sequence repeats.

The term "allelic pattern" refers to the identity of an allele or alleles at one or more polymorphic regions. For example, an allelic pattern may consist of a single allele at a polymorphic site, as for IL-1RN (VNTR) allele 1, which is an allelic pattern having at least one copy of IL-1RN allele 1 at the VNTR of the IL-1RN gene loci. Alternatively, an allelic pattern may consist of either a homozygous or heterozygous state at a single polymorphic site. For example, IL1-RN (VNTR) allele 2,2 is an allelic pattern in which there are two copies of the second allele at the VNTR marker of IL-1RN and that corresponds to the homozygous IL-RN (VNTR) allele 2 state. Alternatively, an allelic pattern may consist of the identity of alleles at more than one polymorphic site.

The term "antibody" as used herein is intended to refer to a binding agent including a whole antibody or a binding fragment thereof which is specifically reactive with an IL-1B polypeptide. Antibodies can be fragmented using conventional techniques and the fragments screened for utility in the same manner as described above for whole antibodies. For example, $F(ab)_2$ fragments can be generated by treating an antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for an IL-1B polypeptide conferred by at least one CDR region of the antibody.

"Biological activity" or "bioactivity" or "activity" or "biological function", which are used interchangeably, for the purposes herein when applied to IL-1 means an effector or antigenic function that is directly or indirectly performed by an IL-1 polypeptide (whether in its native or denatured conformation), or by any subsequence (fragment) thereof. A biological activity can include binding, effecting signal transduction from a receptor, modulation of gene expression or an antigenic effector function.

As used herein the term "bioactive fragment of an IL-1 polypeptide" refers to a fragment of a full-length IL-1 polypeptide, wherein the fragment specifically mimics or antagonizes the activity of a wild-type IL-1 polypeptide. The bioactive fragment preferably is a fragment capable of interacting with an interleukin receptor.

"Cells", "host cells" or "recombinant host cells" are terms used interchangeably herein to refer not only to the particular subject cell, but to the progeny or potential progeny of such a cell. Because certain modifications may occur in succeeding generations due to either mutation or environmental influences, such progeny may not, in fact be identical to the parent cell, but is still included within the scope of the term as used herein.

A "chimera," "mosaic," "chimeric mammal" and the like, refers to a transgenic mammal with a knock-out or knock-in construct in at least some of its genome-containing cells.

The terms "control" or "control sample" refer to any sample appropriate to the detection technique employed. The control sample may contain the products of the allele detection technique employed or the material to be tested. Further, the controls may be positive or negative controls. By way of example, where the allele detection technique is PCR amplification, followed by size fractionation, the control sample may comprise DNA fragments of an appropriate size. Likewise, where the allele detection technique involves detection of a mutated protein, the control sample may comprise a sample of a mutant protein. However, it is preferred that the control sample comprises the material to be tested. For example, the controls may be a sample of genomic DNA or a cloned portion of the IL-1 gene cluster. However, where the sample to be tested is genomic DNA, the control sample is preferably a highly purified sample of genomic DNA.

A "cardiovascular disease" is a cardiovascular disorder, as defined herein, characterized by clinical events including clinical symptoms and clinical signs. Clinical symptoms are those experiences reported by a patient that indicate to the clinician the presence of pathology. Clinical signs are those objective findings on physical or laboratory examination that indicate to the clinician the presence of pathology. "Cardiovascular disease" includes both "coronary artery disease" and "peripheral vascular disease," both terms being defined below. Clinical symptoms in cardiovascular disease include chest pain, shortness of breath, weakness, fainting spells, alterations in consciousness, extremity pain, paroxysmal nocturnal dyspnea, transient ischemic attacks and other such phenomena experienced by the patient. Clinical signs in cardiovascular disease include such findings as EKG abnormalities, altered peripheral pulses, arterial bruits, abnormal heart sounds, rales and wheezes, jugular venous distention, neurological alterations and other such findings discerned by the clinician. Clinical symptoms and clinical signs can combine in a cardiovascular disease such as a myocardial infarction (MI) or a stroke (also termed a "cerebrovascular accident" or "CVA"), where the patient will report certain phenomena (symptoms) and the clinician will perceive other phenomena (signs) all indicative of an underlying pathology. "Cardiovascular disease" includes those diseases related to the cardiovascular disorders of fragile plaque disorder, occlusive disorder and stenosis. For example, a cardiovascular disease resulting from a fragile plaque disorder, as that term is defined below, can be termed a "fragile plaque disease." Clinical events associated with fragile plaque disease include those signs and symptoms where the rupture of a fragile plaque with subsequent acute thrombosis or with distal embolization are hallmarks. Examples of fragile plaque disease include certain strokes and myocardial infarctions. As another example, a cardiovascular disease resulting from an occlusive disorder can be termed an "occlusive disease." Clinical events associated with occlusive disease include those signs and symptoms where the progressive occlusion of an artery affects the amount of circulation that reaches a target tissue. Progressive arterial occlusion may result in progressive ischemia that may ultimately progress to tissue death if the amount of circulation is insufficient to maintain the tissues. Signs and symptoms of occlusive disease include claudication, rest pain, angina, and gangrene, as well as physical and laboratory findings indicative of vessel stenosis and decreased distal perfusion. As yet another example, a cardiovascular disease resulting from restenosis can be termed an in-stent stenosis disease. In-stent stenosis disease includes the signs and symptoms resulting from the progressive blockage of an arterial stent that has been positioned as part of a procedure like a percutaneous transluminal angioplasty, where the presence of the stent is intended to help hold the vessel in its newly expanded configuration. The clinical events that accompany in-stent stenosis disease are those attributable to the restenosis of the reconstructed artery.

A "cardiovascular disorder" refers broadly to both to coronary artery disorders and peripheral arterial disorders. The term "cardiovascular disorder" can apply to any abnormality of an artery, whether structural, histological, biochemical or any other abnormality. This term includes those disorders characterized by fragile plaque (termed herein "fragile plaque disorders"), those disorders characterized by vaso-occlusion (termed herein "occlusive disorders"), and those disorders characterized by restenosis. A "cardiovascular disorder" can occur in an artery primarily, that is, prior to any medical or surgical intervention. Primary cardiovascular disorders include, among others, atherosclerosis, arterial occlusion, aneurysm formation and thrombosis. A "cardiovascular disorder" can occur in an artery secondarily, that is, following a medical or surgical intervention. Secondary cardiovascular disorders include, among others, post-traumatic aneurysm formation, restenosis, and post-operative graft occlusion.

A "cardiovascular disorder causative functional mutation" refers to a mutation which causes or contributes to the development of a cardiovascular disorder in a subject. Preferred mutations occur within the IL-1 complex. A cardiovascular disorder causative functional mutation occurring within an IL-1 gene (e.g. IL-1A, IL-1B or IL-1RN) or a gene locus, which is linked thereto, may alter, for example, the open reading frame or splicing pattern of the gene, thereby resulting in the formation of an inactive or hypoactive gene product. For example, a mutation which occurs in intron 6 of the IL-1A locus corresponds to a variable number of tandem repeat 46 bp sequences corresponding to from five to 18 repeat units (Bailly, et al. (1993) Eur. J. Immunol. 23: 1240-45). These repeat sequences contain three potential binding sites for transcriptional factors: an SP 1 site, a viral enhancer element, and a glucocorticoid-responsive element; therefore individuals carrying IL-1A intron 6 VNTR alleles with large numbers of repeat units may be subject to altered transcriptional regulation of the IL-1A gene and consequent perturbations of inflammatory cytokine production. Indeed, there is evidence that increased repeat number at this polymorphic IL-1A locus leads to decreased IL-1α synthesis (Bailly et al. (1996) Mol Immunol 33: 999-1006). Alternatively, a mutation can result in a hyperactive gene product. For example, allele 2 of the IL-1B (G at +6912) polymorphism occurs in the 3' UTR (untranslated region) of the IL-1B mRNA and is associated with an approximately four-fold increase in the steady state levels of both IL-1B mRNA and IL-1B protein compared to those levels associated with allele 1 of the IL-1B gene at +6912). Further, an IL-1B (−511) mutation occurs near a promoter binding site for a negative glucocorticoid response element (Zhang et al. (1997) DNA Cell Biol 16: 145-52). This element potentiates a four-fold repression of IL-1B expression by dexamethosone and a deletion of this negative response elements causes a 2.5-fold increase in IL-1B promoter activity. The IL-1B (−511) polymorphism may thus directly affect cytokine production and inflammatory responses. These examples demonstrate that genetic variants occurring in the IL-1A or IL-1B gene can directly lead to the altered production or regulation of IL-1 cytokine activity.

A "cardiovascular disorder therapeutic" refers to any agent or therapeutic regimen (including pharmaceuticals, nutraceuticals and surgical means) that prevents or postpones the development of or reduces the extent of an abnormality constitutive of a cardiovascular disorder in a subject. Cardiovascular disorder therapeutics can be directed to the treatment of any cardiovascular disorder, including fragile plaque disorder, occlusive disorder and restenosis. Examples of therapeutic agents directed to each category of cardiovascular disorder are provided herein. It is understood that a therapeutic agent may be useful for more than one category of cardiovascular disorder. The therapeutic can be a polypeptide, peptidomimetic, nucleic acid or other inorganic or organic molecule, preferably a "small molecule" including vitamins, minerals and other nutrients. Preferably the therapeutic can modulate at least one activity of an IL-1 polypeptide, e.g., interaction with a receptor, by mimicking or potentiating (agonizing) or inhibiting (antagonizing) the effects of a naturally-occurring polypeptide. An IL-1 agonist can be a wild-type protein or derivative thereof having at least one bioactivity of the wild-type, e.g., receptor binding activity. An IL-1 agonist can also be a compound that upregulates expression of a gene or which increases at least one bioactivity of a protein. An IL-1 agonist can also be a compound which increases the interaction of a polypeptide with another molecule, e.g., a receptor. An IL-1 antagonist can be a compound which inhibits or decreases the interaction between a protein and another molecule, e.g., a receptor or an agent that blocks signal transduction or post-translation processing (e.g., IL-1 converting enzyme (ICE) inhibitor). Accordingly, a preferred antagonist is a compound which inhibits or decreases binding to a receptor and thereby blocks subsequent activation of the receptor. An IL-1 antagonist can also be a compound that downregulates expression of a gene or which reduces the amount of a protein present. The antagonist can be a dominant negative form of a polypeptide, e.g., a form of a polypeptide which is capable of interacting with a target peptide, e.g., a receptor, but which does not promote the activation of the receptor. The antagonist can also be a nucleic acid encoding a dominant negative form of a polypeptide, an antisense nucleic acid, or a ribozyme capable of interacting specifically with an RNA. Yet other antagonists are molecules which bind to a polypeptide and inhibit its action. Such molecules include peptides, e.g., forms of target peptides which do not have biological activity, and which inhibit binding to receptors. Thus, such peptides will bind to the active site of a protein and prevent it from interacting with target peptides. Yet other antagonists include antibodies that specifically interact with an epitope of a molecule, such that binding interferes with the biological function of the polypeptide. In yet another preferred embodiment, the antagonist is a small molecule, such as a molecule capable of inhibiting the interaction between a polypeptide and a target receptor. Alternatively, the small molecule can function as an antagonist by interacting with sites other than the receptor binding site.

Preferred therapeutics include lipid lowering drugs, anti-platelet agents, anti-inflammatory agents and antihypertensive agents.

"Cerebrovascular disease," as used herein, is a type of peripheral vascular disease (as defined below) where the peripheral vessel blocked is part of the cerebral circulation. The cerebral circulation includes the carotid and the vertebral arterial systems. This definition of cerebrovascular disease is intended specifically to include intracranial hemorrhage that does not occur as a manifestation of an arterial blockage. Blockage can occur suddenly, by mechanisms such as plaque rupture or embolization. Blockage can occur progressively, with narrowing of the artery via myointimal hyperplasia and plaque formation. Blockage can be complete or partial. Certain degrees and durations of blockage result in cerebral ischemia, a reduction of blood flow that lasts for several seconds to minutes. The prolongation of cerebral ischemia can result in cerebral infarction. Ischemia and infarction can be focal or widespread. Cerebral ischemia or infarction can result in the abrupt onset of a non-convulsive focal neurological defect, a clinical event termed a "stroke" or a "cerebrovascular accident (CVA)". Cerebrovascular disease has two broad categories of pathologies: thrombosis and embolism. Thrombotic strokes occur without warning symptoms in 80-90% of patients; between 10 and 20% of thrombotic strokes are heralded by transient ischemic attacks. A cerebrovascular disease can be associated with a fragile plaque disorder. The signs and symptoms of this type of cerebrovascular disease are those associated with fragile plaque, including stroke due to sudden arterial blockage with thrombus or embolus formation. A cerebrovascular disease can be associated with occlusive disorder. The signs and symptoms of this type of cerebrovascular disease relate to progressive blockage of blood flow with global or local cerebral ischemia. In this setting, neurological changes can be seen, including stroke.

A "clinical event" is an occurrence of clinically discernible signs of a disease or of clinically reportable symptoms of a disease. "Clinically discernible" indicates that the sign can be appreciated by a health care provider. "Clinically reportable" indicates that the symptom is the type of phenomenon that can be described to a health care provider. A clinical event may comprise clinically reportable symptoms even if the particular patient cannot himself or herself report them, as long as these are the types of phenomena that are generally capable of description by a patient to a health care provider.

A "coronary artery disease" ("CAD") refers to a vascular disorder relating to the blockage of arteries serving the heart. Blockage can occur suddenly, by mechanisms such as plaque rupture or embolization. Blockage can occur progressively, with narrowing of the artery via myointimal hyperplasia and plaque formation. Those clinical signs and symptoms resulting from the blockage of arteries serving the heart are manifestations of coronary artery disease. Manifestations of coronary artery disease include angina, ischemia, myocardial infarction, cardiomyopathy, congestive heart failure, arrhythmias and aneurysm formation. It is understood that fragile plaque disease in the coronary circulation is associated with arterial thrombosis or distal embolization that manifests itself as a myocardial infarction. It is understood that occlusive disease in the coronary circulation is associated with arterial stenosis accompanied by anginal symptoms, a condition commonly treated with pharmacological interventions and with angioplasty.

A "disease" is a disorder characterized by clinical events including clinical signs and clinical symptoms. The diseases discussed herein include cardiovascular disease, peripheral vascular disease, CAD, cerebrovascular disease, and those diseases in any anatomic location associated with fragile plaque disorder, with occlusive disorder or with restenosis.

A "disorder associated allele" or "an allele associated with a disorder" refers to an allele whose presence in a subject indicates that the subject has or is susceptible to developing a particular disorder. One type of disorder associated allele is a "cardiovascular disorder associated allele," the presence of which in a subject indicates that the subject has or is susceptible to developing a cardiovascular disorder. These include broadly within their scope alleles which are associated with "fragile plaque disorders," alleles associated with "occlusive disorders," and alleles associated with restenosis. Examples of alleles associated with "fragile plaque disorders" include allele 2 of the IL-1A +4825; allele 2 of the +3954 marker of IL-1B; and allele 1 of the +2018 marker of IL-1RN; and allele 1 of the (−511) marker of the IL-1B gene or an allele that is in linkage disequilibrium with one of the aforementioned alleles. Examples of alleles associated with "occlusive disorders" include allele 1 of the IL-1A +4825; allele 1 of the +3954 marker of IL-1B; and allele 2 of the +2018 marker of IL-1RN; and allele 2 of the (−511) marker of the IL-1B gene or an allele that is in linkage disequilibrium with one of the aforementioned alleles. Examples of alleles associated with restenosis include the combination of either allele 1 of the +4825 marker of IL-1A or allele 1 of the +3954 marker as combined with either allele 1 of the −511 marker of IL-1B or allele 1 of the +2018 marker of IL-1RN, or an allele that is in linkage disequilibrium with one of the aforementioned alleles. A "periodontal disorder associated allele" refers to an allele whose presence in a subject indicates that the subject has or is susceptible to developing a periodontal disorders.

The phrases "disruption of the gene" and "targeted disruption" or any similar phrase refers to the site specific interruption of a native DNA sequence so as to prevent expression of that gene in the cell as compared to the wild-type copy of the gene. The interruption may be caused by deletions, insertions or modifications to the gene, or any combination thereof.

As used herein, the terms "embolus," "embolism" or "embolization" refer to artery-to-artery embolism or embolization.

"Fragile plaque disorder" refers to that cardiovascular disorder characterized by the formation of fragile plaque as part of the arteriosclerotic process within an artery. The fragile plaque is prone to fracture, thrombosis or rupture. When the integrity of the plaque is altered, it can mechanically block the vessel locally or it can send fragments or associated clot downstream in the vessel to cause blockage more distally. If the plaque cracks, it can be a nidus for a local thrombus to form. Fragile plaque disorder is associated with allele pattern 1 at the IL-1 locus.

A "fragile plaque disorder therapeutic" refers to any agent or therapeutic regimen (including pharmaceuticals, nutraceuticals and surgical means) that prevents or postpones the development of or reduces the extent of an abnormality constitutive of a fragile plaque disorder in a subject. This term includes certain agents that operate by stabilizing fragile plaque, certain agents with anti-thrombotic or anti-platelet effect, and certain agents with antioxidant effect. Examples of fragile plaque disorder associated therapeutics include statin drugs, anti-inflammatory agents with anti-prostaglandin effect, anti-inflammatory agents and cytokine inhibitors directed against IL-1 and TNF-alpha such as Tenidap, matrix metalloproteanase (MMP) inhibitors including tetracycline and related agents and specific MMP inhibitors, and recombinant IL-1 receptor antagonists. Furthermore, this term includes those nutriceuticals that block IL-1, agents such as fish oils, omega-3 fatty acids, polyunsaturated fatty acids, and those nutriceuticals with antioxidant effect such as butylated hydroxyanisol (BHA).

The term "haplotype" as used herein is intended to refer to a set of alleles that are inherited together as a group (are in linkage disequilibrium) at statistically significant levels ($p_{corr}$<0.05). As used herein, the phrase "an IL-1 haplotype" refers to a haplotype in the IL-1 loci.

An "IL-1 agonist" as used herein refers to an agent that mimics, upregulates (potentiates or supplements) or otherwise increases an IL-1 bioactivity or a bioactivity of a gene in an IL-1 biological pathway. IL-1 agonists may act on any of a variety of different levels, including regulation of IL-1 gene expression at the promoter region, regulation of mRNA splicing mechanisms, stabilization of mRNA, phosphorylation of proteins for translation, conversion of proIL-1 to mature IL-1 and secretion of IL-1. Agonists that increase IL-1 synthesis include: lipopolysaccharides, IL-1B, cAMP inducing agents, NFκB activating agents, AP-1 activating agents, TNF-α, oxidized LDL, advanced glycosylation end products (AGE), sheer stress, hypoxia, hyperoxia, ischemia reperfusion injury, histamine, prostaglandin E 2 (PGE2), IL-2, IL-3, IL-12, granulocyte macrophage-colony stimulating factor (GM-CSF), monocyte colony stimulating factor (M-CSF), stem cell factor, platelet derived growth factor (PDGF), complement C5A, complement C5b9, fibrin degradation products, plasmin, thrombin, 9-hydroxyoctadecaenoic acid, 13-hydroxyoctadecaenoic acid, platelet activating factor (PAF), factor H, retinoic acid, uric acid, calcium pyrophosphate, polynucleosides, c-reactive protein, α-antitrypsin, tobacco antigen, collagen, β-1 integrins, LFA-3, anti-HLA-DR, anti-IgM, anti-CD3, phytohemagglutinin (CD2), sCD23, ultraviolet B radiation, gamma radiation, substance P, isoproterenol, methamphetamine and melatonin. Agonists that stabilize IL-1 mRNA include bacterial endotoxin and IL-1. Other agonists, that function by increasing the number of IL-1 type 1 receptors available, include IL-1, PKC activators, dexamethasone, IL-2, IL-4 and PGE2. Other preferred antagonists interfere or inhibit signal transduction factors activated by IL-1 or utilized in an IL-1 signal transduction pathway (e.g NFκB and AP-1, PI3 kinase, phospholipase A2, protein kinase C, JNK-1, 5-lipoxygenase, cyclooxygenase 2, tyrosine phosphorylation, iNOS pathway, Rac, Ras, TRAF). Still other agonists increase the bioactivity of genes whose expression is induced by IL-1, including: IL-1, IL-1Ra, TNF, IL-2, IL-3, IL-6, IL-12, GM-CSF, G-CSF, TGF-β, fibrinogen, urokinase plasminogen inhibitor, Type 1 and type 2 plasminogen activator inhibitor, p-selectin (CD62), fibrinogen receptor, CD-11/CD18, protease nexin-1, CD44, Matrix metalloproteinase-1 (MMP-1), MMP-3, Elastase, Collagenases, Tissue inhibitor of metalloproteinases-1 (TIMP-1), Collagen, Triglyceride increasing Apo CIII, Apolipoprotein, ICAM-1, ELAM-1, VCAM-1, L-selectin, Decorin, stem cell factor, Leukemia inhibiting factor, IFNα, β, γ, L-8, IL-2 receptor, IL-3 receptor, IL-5 receptor, c-kit receptor, GM-CSF receptor, Cyclooxygenase-2 (COX-2), Type 2 phospholipase A2, Inducible nitric oxide synthase (iNOS), Endothelin-1,3, Gamma glutamyl transferase, Mn superoxide dismutase, C-reactive protein, Fibrinogen, Serum amyloid A, Metallothioneins, Ceruloplasmin, Lysozyme, Xanthine dehydrogenase, Xanthine oxidase, Platelet derived growth factor A chain (PDGF), Melanoma growth stimulatory activity (gro-α, β, γ), Insulin-like growth factor-1 (IGF-1), Activin A, Pro-opiomelanocortiotropin, corticotropin releasing factor, B amyloid precursor, Basement membrane protein-40, Laminin B1 and B2, Constitutive heat shock protein p70, P42 mitogen, activating protein kinase, ornithine decarboxylase, heme oxygenase and G-protein α subunit).

An "IL-1 antagonist" as used herein refers to an agent that downregulates or otherwise decreases an IL-1 bioactivity. IL-1 antagonists may act on any of a variety of different levels, including regulation of IL-1 gene expression at the promoter region, regulation of mRNA splicing mechanisms, stabilization of mRNA, phosphorylation of proteins for translation, conversion of proIL-1 to mature IL-1 and secretion of IL-1. Antagonists of IL-1 production include: corticosteroids, lipoxygenase inhibitors, cyclooxygenase inhibitors, γ-interferon, IL-4, IL-10, IL-13, transforming growth factor β (TGF-β), ACE inhibitors, n-3 polyunsaturated fatty acids, antioxidants and lipid reducing agents. Antagonists that destabilize IL-1 mRNA include agents that promote deadenylation. Antagonists that inhibit or prevent phosphorylation of IL-1 proteins for translation include pyridinyl-imadazole compounds, such as tebufelone and compounds that inhibit microtubule formation (e.g. colchicine, vinblastine and vincristine). Antagonists that inhibit or prevent the conversion of proIL-1 to mature IL-1 include interleukin converting enzyme (ICE) inhibitors, such as ICE isoforms, ICE α, β, and γ isoform antibodies, CXrm-A, transcript X, endogenous tetrapeptide competitive substrate inhibitor, trypsin, elastase, chymotrypsin, chymase, and other nonspecific proteases. Antagonists that prevent or inhibit the secretion of IL-1 include agents that block anion transport. Antagonists that interfere with IL-1 receptor interactions, include: agents that inhibit glycosylation of the type I IL-1 receptor, antisense oligonucleotides against IL-1RI, antibodies to IL-1RI and antisense oligonucleotides against IL-1RacP. Other antagonists, that function by decreasing the number of IL-1 type 1 receptors available, include TGF-β, COX inhibitors, factors that increase IL-1 type II receptors, dexamethasone, PGE2, IL-1 and IL-4. Other preferred antagonists interfere or inhibit signal transduction factors activated by IL-1 or utilized in an IL-1 signal transduction pathway (e.g NFκB and AP-1, PI3 kinase, phospholipase A2, protein kinase C, JNK-1, 5-lipoxygenase, cyclooxygenase 2, tyrosine phosphorylation, iNOS pathway, Rac, Ras, TRAF). Still other antagonists interfere with the bioactivity of genes whose expression is induced by IL-1, including: IL-1, IL-1Ra, TNF, IL-2, IL-3, IL-6, IL-12, GM-CSF, G-CSF, TGF-β fibrinogen, urokinase plasminogen inhibitor, Type 1 and type 2 plasminogen activator inhibitor, p-selectin (CD62), fibrinogen receptor, CD-11/CD18, protease nexin-1, CD44, Matrix metalloproteinase-1 (MMP-1), MMP-3, Elastase, Collagenases, Tissue inhibitor of metalloproteinases-1 (TIMP-1), Collagen, Triglyceride increasing Apo CIII, Apolipoprotein, ICAM-1, ELAM-1, VCAM-1, L-selectin, Decorin, stem cell factor, Leukemia inhibiting factor, IFNα, β, γ, L-8, IL-2 receptor, IL-3 receptor, IL-5 receptor, c-kit receptor, GM-CSF receptor, Cyclooxygenase-2 (COX-2), Type 2 phospholipase A2, Inducible nitric oxide synthase (iNOS), Endothelin-1,3, Gamma glutamyl transferase, Mn superoxide dismutase, C-reactive protein, Fibrinogen, Serum amyloid A, Metallothioneins, Ceruloplasmin, Lysozyme, Xanthine dehydrogenase, Xanthine oxidase, Platelet derived growth factor A chain (PDGF), Melanoma growth stimulatory activity (gro-α, β, γ), Insulin-like growth factor-1 (IGF-1), Activin A, Pro-opiomelanocortiotropin, corticotropin releasing factor, B amyloid precursor, Basement membrane protein-40, Laminin B1 and B2, Constitutive heat shock protein p70, P42 mitogen, activating protein kinase, ornithine decarboxylase, heme oxygenase and G-protein α subunit). Other preferred antagonists include: hymenialdisine, herbamycines (e.g. herbamycin A), CK-103A and its derivatives (e.g. 4,6-dihydropyridazino[4,5-c]pyridazin-5

(1H)-one), CK-119, CK-122, iodomethacin, aflatoxin B1, leptin, heparin, bicyclic imidazoles (e.g SB203580), PD15306 HCl, podocarpic acid derivatives, M-20, Human [Gly2] Glucagon-like peptide-2, FR167653, Steroid derivatives, glucocorticoids, Quercetin, Theophylline, NO-synthetase inhibitors, RWJ 68354, Euclyptol (1.8-cineole), Magnosalin, N-Acetylcysteine, Alpha-Melatonin-Stimulating Hormone ($\alpha$-MSH), Triclosan (2,4,4'-trichloro-2'-hydroxydiphenyl ether), Prostaglandin E2 and 4-aminopyridine Ethacrynic acid and 4,4'-diisothiocyanatostilbene-2,2'-disulfonic acid (DIDS), Glucose, Lipophosphoglycan, aspirin, Catabolism-blocking agents, Diacerhein, Thiol-modulating agents, Zinc, Morphine, Leukotriene biosynthesis inhibitors (e.g. MK886), Platelet-activating factor receptor antagonists (e.g. WEB 2086), Amiodarone, Tranilast, S-methyl-L-thiocitrulline, Beta-adrenoreceptor agonists (e.g. Procaterol, Clenbuterol, Fenoterol, Terbutaline, Hyaluronic acid, anti-TNF-$\alpha$ antibodies, anti-IL-1$\alpha$ autoantibodies, IL-1 receptor antagonist, IL-1R-associated kinase, soluble TNF receptors and antiinflammatory cytokines (e.g IL-4, IL-13, IL-10, IL-6, TGF-$\beta$, angiotensin II, Soluble IL-1 type II receptor, Soluble IL-1 type I receptor, Tissue plasminogen activator, Zinc finger protein A20 IL-1 Peptides (e.g (Thr-Lys-Pro-Arg) (Tuftsin), (Ile-Thr-Gly-Ser-Glu) IL-1-alpha, Val-Thr-Lys-Phe-Tyr-Phe, Val-Thr-Asp-Phe-Tyr-Phe, Interferon alpha2b, Interferon beta, IL-1-beta analogues (e.g. IL-1-beta tripeptide: Lys-D-Pro-Thr), glycosylated IL-1-alpha, and IL-1ra peptides.

The terms "IL-1 gene cluster" and "IL-1 loci" as used herein include all the nucleic acid at or near the 2q13 region of chromosome 2, including at least the IL-1A, IL-1B and IL-1RN genes and any other linked sequences. (Nicklin et al., Genomics 19: 382-84, 1994). The terms "IL-1A", "IL-1B", and "IL-1RN" as used herein refer to the genes coding for IL-1$\alpha$, IL-1$\beta$, and IL-1 receptor antagonist, respectively. The gene accession number for IL-1A, IL-1B, and IL-1RN are X03833, X04500, and X64532, respectively.

"IL-1 functional mutation" refers to a mutation within the IL-1 gene cluster that results in an altered phenotype (i.e. affects the function of an IL-1 gene or protein). Examples include: IL-1A (+4845) allele 2, IL-1B (+3954) allele 2, IL-1B (−511) allele 1 and IL-1RN (+2018) allele 1.

"IL-1X (Z) allele Y" refers to a particular allelic form, designated Y, occurring at an IL-1 locus polymorphic site in gene X, wherein X is IL-1A, B, or RN or some other gene in the IL-1 gene loci, and positioned at or near nucleotide Z, wherein nucleotide Z is numbered relative to the major transcriptional start site, which is nucleotide +1, of the particular IL-1 gene X. As further used herein, the term "IL-1X allele (Z)" refers to all alleles of an IL-1 polymorphic site in gene X positioned at or near nucleotide Z. For example, the term "IL-1RN (+2018) allele" refers to alternative forms of the IL-1RN gene at marker +2018. "IL-1RN (+2018) allele 1" refers to a form of the IL-1RN gene which contains a cytosine (C) at position +2018 of the sense strand. Clay et al., Hum. Genet. 97:723-26, 1996. "IL-1RN (+2018) allele 2" refers to a form of the IL-1RN gene which contains a thymine (T) at position +2018 of the plus strand. When a subject has two identical IL-1RN alleles, the subject is said to be homozygous, or to have the homozygous state. When a subject has two different IL-1RN alleles, the subject is said to be heterozygous, or to have the heterozygous state. The term "IL-1RN (+2018) allele 2,2" refers to the homozygous IL-1RN (+2018) allele 2 state. Conversely, the term "IL-1RN (+2018) allele 1,1" refers to the homozygous IL-1RN (+2018) allele 1 state. The term "IL-1RN (+2018) allele 1,2" refers to the heterozygous allele 1 and 2 state.

"IL-1 related" as used herein is meant to include all genes related to the human IL-1 locus genes on human chromosome 2 (2 q 12-14). These include IL-1 genes of the human IL-1 gene cluster located at chromosome 2 (2 q 13-14) which include: the IL-1A gene which encodes interleukin-1$\alpha$, the IL-1B gene which encodes interleukin-1$\beta$, and the IL-1RN (or IL-1ra) gene which encodes the interleukin-1 receptor antagonist. Furthermore these IL-1 related genes include the type I and type II human IL-1 receptor genes located on human chromosome 2 (2q12) and their mouse homologs located on mouse chromosome 1 at position 19.5 cM. Interleukin-1$\alpha$, interleukin-1$\beta$, and interleukin-1RN are related in so much as they all bind to IL-1 type I receptors, however only interleukin-1$\alpha$ and interleukin-1$\beta$ are agonist ligands which activate IL-1 type I receptors, while interleukin-1RN is a naturally occurring antagonist ligand. Where the term "IL-1" is used in reference to a gene product or polypeptide, it is meant to refer to all gene products encoded by the interleukin-1 locus on human chromosome 2 (2q 12-14) and their corresponding homologs from other species or functional variants thereof. The term IL-1 thus includes secreted polypeptides which promote an inflammatory response, such as IL-1$\alpha$ and IL-1$\beta$, as well as a secreted polypeptide which antagonize inflammatory responses, such as IL-1 receptor antagonist and the IL-1 type II (decoy) receptor.

An "IL-1 receptor" or "IL-1R" refers to various cell membrane bound protein receptors capable of binding to and/or transducing a signal from IL-1 locus-encoded ligand. The term applies to any of the proteins which are capable of binding interleukin-1 (IL-1) molecules and, in their native configuration as mammalian plasma membrane proteins, presumably play a role in transducing the signal provided by IL-1 to a cell. As used herein, the term includes analogs of native proteins with IL-1-binding or signal transducing activity. Examples include the human and murine IL-1 receptors described in U.S. Pat. No. 4,968,607. The term "IL-1 nucleic acid" refers to a nucleic acid encoding an IL-1 protein.

An "IL-1 polypeptide" and "IL-1 protein" are intended to encompass polypeptides comprising the amino acid sequence encoded by the IL-1 genomic DNA sequences for IL-1$\alpha$, IL-1$\beta$ and IL-1RN, or fragments thereof, and homologs thereof and include agonist and antagonist polypeptides.

"In-stent stenosis" refers to the progressive occlusion within a stent that has been placed during angioplasty. In-stent stenosis is a form of restenosis that takes place within an arterial stent.

"Increased risk" refers to a statistically higher frequency of occurrence of the disease or disorder in an individual in comparison to the frequency of occurrence of the disease or disorder in a population. A factor identified to be associated with increased risk is termed a "risk factor." Carrying a particular polymorphic allele is a risk factor for a particular cardiovascular disease, and is associated with an increased risk of the particular disease.

The term "interact" as used herein is meant to include detectable relationships or associations (e.g. biochemical interactions) between molecules, such as interactions between protein-protein, protein-nucleic acid, nucleic acid-nucleic acid and protein-small molecule or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject IL-1 polypeptides preferably includes no more than 10 kilobases (kb) of nucleic acid sequence which naturally immediately flanks the IL-1 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

A "knock-in" transgenic animal refers to an animal that has had a modified gene introduced into its genome and the modified gene can be of exogenous or endogenous origin.

A "knock-out" transgenic animal refers to an animal in which there is partial or complete suppression of the expression of an endogenous gene (e.g, based on deletion of at least a portion of the gene, replacement of at least a portion of the gene with a second sequence, introduction of stop codons, the mutation of bases encoding critical amino acids, or the removal of an intron junction, etc.).

A "knock-out construct" refers to a nucleic acid sequence that can be used to decrease or suppress expression of a protein encoded by endogenous DNA sequences in a cell. In a simple example, the knock-out construct is comprised of a gene, such as the IL-1RN gene, with a deletion in a critical portion of the gene so that active protein cannot be expressed therefrom. Alternatively, a number of termination codons can be added to the native gene to cause early termination of the protein or an intron junction can be inactivated. In a typical knock-out construct, some portion of the gene is replaced with a selectable marker (such as the neo gene) so that the gene can be represented as follows: IL-1RN 5'/neo/IL-1RN 3', where IL-1RN5' and IL-1RN 3', refer to genomic or cDNA sequences which are, respectively, upstream and downstream relative to a portion of the IL-1RN gene and where neo refers to a neomycin resistance gene. In another knock-out construct, a second selectable marker is added in a flanking position so that the gene can be represented as: IL-1RN/neo/IL-1RN/TK, where TK is a thymidine kinase gene which can be added to either the IL-1RN5' or the IL-1RN3' sequence of the preceding construct and which further can be selected against (i.e. is a negative selectable marker) in appropriate media. This two-marker construct allows the selection of homologous recombination events, which removes the flanking TK marker, from non-homologous recombination events which typically retain the TK sequences. The gene deletion and/or replacement can be from the exons, introns, especially intron junctions, and/or the regulatory regions such as promoters.

"Linkage disequilibrium" refers to co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in "linkage disequilibrium". The cause of linkage disequilibrium is often unclear. It can be due to selection for certain allele combinations or to recent admixture of genetically heterogeneous populations. In addition, in the case of markers that are very tightly linked to a disease gene, an association of an allele (or group of linked alleles) with the disease gene is expected if the disease mutation occurred in the recent past, so that sufficient time has not elapsed for equilibrium to be achieved through recombination events in the specific chromosomal region. When referring to allelic patterns that are comprised of more than one allele, a first allelic pattern is in linkage disequilibrium with a second allelic pattern if all the alleles that comprise the first allelic pattern are in linkage disequilibrium with at least one of the alleles of the second allelic pattern. An example of linkage disequilibrium is that which occurs between the alleles at the IL-1RN (+2018) and IL-1RN (VNTR) polymorphic sites. The two alleles at IL-1RN (+2018) are 100% in linkage disequilibrium with the two most frequent alleles of IL-1RN (VNTR), which are allele 1 and allele 2.

The term "marker" refers to a sequence in the genome that is known to vary among individuals. For example, the IL-1RN gene has a marker that consists of a variable number of tandem repeats (VNTR).

"Modulate" refers to the ability of a substance to regulate bioactivity. When applied to an IL-1 bioactivity, an agonist or antagonist can modulate bioactivity for example by agonizing or antagonizing an IL-1 synthesis, receptor interaction, or IL-1 mediated signal transduction mechanism.

A "mutated gene" or "mutation" or "functional mutation" refers to an allelic form of a gene, which is capable of altering the phenotype of a subject having the mutated gene relative to a subject which does not have the mutated gene. The altered phenotype caused by a mutation can be corrected or compensated for by certain agents. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant.

A "non-human animal" of the invention includes mammals such as rodents, non-human primates, sheep, dogs, cows, goats, etc. amphibians, such as members of the *Xenopus* genus, and transgenic avians (e.g. chickens, birds, etc.). The term "chimeric animal" is used herein to refer to animals in which the recombinant gene is found, or in which the recombinant gene is expressed in some but not all cells of the animal. The term "tissue-specific chimeric animal" indicates that one of the recombinant IL-1 genes is present and/or expressed or disrupted in some tissues but not others. The term "non-human mammal" refers to any member of the class Mammalia, except for humans.

As used herein, the term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs (e.g. peptide nucleic acids) and as applicable to the embodiment being described, single (sense or antisense) and double-stranded polynucleotides.

"Occlusive disorder" refers to that cardiovascular disorder characterized by the progressive thickening of an arterial wall, associated with the presence of an atherosclerotic intimal lesion within an artery. Occlusive disorder leads to progressive blockage of the artery. With sufficient progression, the occlusive disorder can reduce flow in the artery to the point that clinical signs and symptoms are produced in the tissues perfused by the artery. These clinical events relate to ischemia of the perfused tissues. When severe, ischemia is accompanied by tissue death, called infarction or gangrene. Occlusive disorder is associated with the allele pattern 2s at the IL-1 locus.

An "occlusive disorder therapeutic" refers to any agent or therapeutic regimen (including pharmaceuticals, nutraceuticals and surgical means) that prevents or postpones the development of or reduces the extent of an abnormality constitutive of an occlusive disorder in a subject. Examples of occlusive disorder therapeutics include those agents that are anti-oxidants, those that lower serum lipids, those that block the action of oxidized lipids and other agents that influence lipid metabolism or otherwise have lipid-active effects.

A "peripheral vascular disease" ("PVD") is a cardiovascular disease resulting from the blockage of the peripheral (i.e., non-coronary) arteries. Blockage can occur suddenly, by mechanisms such as plaque rupture or embolization, as occurs in fragile plaque disease. Blockage can occur progressively, with narrowing of the artery via myointimal hyperplasia and plaque formation, as in occlusive disease. Blockage can be complete or partial. Those clinical signs and symptoms resulting from the blockage of peripheral arteries are manifestations of peripheral vascular disease. Manifestations of peripheral vascular diseases include, inter alia, claudication, ischemia, intestinal angina, vascular-based renal insufficiency, transient ischemic attacks, aneurysm formation, peripheral embolization and stroke. Ischemic cerebrovascular disease is a type of peripheral vascular disease.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A specific genetic sequence at a polymorphic region of a gene is an allele. A polymorphic region can be a single nucleotide, the identity of which differs in different alleles. A polymorphic region can also be several nucleotides long.

The term "propensity to disease," also "predisposition" or "susceptibility" to disease or any similar phrase, means that certain alleles are hereby discovered to be associated with or predictive of a subject's incidence of developing a particular disease (herein, a cardiovascular disease). The alleles are thus over-represented in frequency in individuals with disease as compared to healthy individuals. Thus, these alleles can be used to predict disease even in pre-symptomatic or pre-diseased individuals. These alleles are understood to relate to the disorder underlying the disease.

The term "restenosis" refers to any preocclusive lesion that develops following a reconstructive procedure in a diseased blood vessel. The term is not only applied to the recurrence of a pre-existing stenosis, but also to previously normal vessels such as vein grafts that become partially occluded following vascular bypass. Restenosis refers to any luminal narrowing that occurs following a therapeutic intervention directed to an artery. Injuries resulting in restenosis can therefore include trauma to an atherosclerotic lesion (as seen with angioplasty), a resection of a lesion (as seen with endarterectomy), an external trauma (e.g., a cross-clamping injury), or a surgical anastomosis. Restenosis can occur as the result of any time of vascular reconstruction, whether in the coronary vasculature or in the periphery (Colburn and Moore (1998) Myointimal Hyperplasia pp. 690-709 in Vascular Surgery: A Comprehensive Review (Philadelphia: Saunders, 1998)). For example, studies have reported symptomatic restenosis rates of 30-50% following coronary angioplasties (see Berk and Harris (1995) Adv. Intern. Med. 40:455-501). After carotid endarterectomies, as a further example, 20% of patients studied had a luminal narrowing greater than 50% (Clagett et al. (1986) J. Vasc. Surg. 3:10-23). Yet another example of restenosis is seen in infrainguinal vascular bypasses, where 40-60% of prosthetic grafts and 20-40% of the vein grafts are occluded at three years (Dalman and Taylor (1990) Ann. Vasc. Surg. 3:109-312, Szilagyi et al. (1973) Ann. Surg. 178:232-246). Different degrees of symptomatology accompany preocclusive lesions in different anatomical locations, due to a combination of factors including the different calibers of the vessels involved, the extent of residual disease and local hemodynamics. In-stent stenosis is a type of restenosis.

A "restenosis disorder therapeutic" refers to any agent or therapeutic regimen (including pharmaceuticals, nutraceuticals and surgical means) that prevents or postpones the development of or reduces the extent of an abnormality constitutive of a restenosis disorder in a patient. Restenosis is understood to comprise three phases. The first phase is characterized by an inflammatory response involving the recruitment of leukocytes to the site of injury and by the formation of thrombus during the first forty-eight hours. The endothelium is activated with the expression of adhesion molecules ICAM-1, E-selectin, P-selectin and VCAM-1. At the same time, macrophages and fibroblasts begin to migrate into the injury site by means of upregulation of integrins. The second phase is characterized by the proliferation of smooth muscle cells in the vessel wall media and the migration of these cells into the intima where they migrate. Growth factors and cytokines that regulate the proliferation and migration of smooth muscle cells are released from the platelets, leukocytes and smooth muscle cells. The last phase includes the secretory phase of extracellular matrix from smooth muscle cells. A restenosis disorder therapeutics may act to affect any of these processes in modulating the course of restenosis. Restenosis disorder therapeutics may include those agents that influence the processes of NO synthesis, such as troglitazone and tranilast. Restenosis disorder therapeutics include physical interventions such as radiation therapies that influence the progression of restenosis or of in-stent restenosis. Restenosis disorder therapeutics include stent modification techniques such as seeding stents with genetically modified endothelial cells, coating stents with heparin or related agents, providing drug-loaded polymer stents, sconstructing polymer-coated stents eluting platelet glycoprotein receptor antibodies or other stent modifications. Restenosis disorder therapeutics include genetic engineering techniques, for example, those that involve transfer of therapeutic genes or and those that involve incorporation of plasmid DNA in hydrogel coated medical devices. Restenosis disorder therapeutics also include surgical manipulations or parts of surgical treatment plans intended to minimize the incidence of restenosis or to avoid it. Restenosis disorders are understood to occur in all native arteries subjected to endovascular manipulation and in autogenous veins used as vascular grafts. Intimal hyperplasia of either the proximal or the distal anastomosis or of the vein graft itself continues to be the leading cause of late failures of infrainguinal vascular reconstructions, for example. In prosthetic graft reconstructions, such problems are extremely unusual. Diagnosing a propensity for an occlusive disorder might guide the surgeon in selecting the type of graft material to be used for a vascular reconstruction, or might influence the choice of pharmacological agents to be used as adjuncts to the procedure.

A "risk factor" is a factor identified to be associated with an increased risk. A risk factor for a cardiovascular disorder or a cardiovascular disease is any factor identified to be associated with an increased risk of developing those conditions or of worsening those conditions. A risk factor can also be associated with an increased risk of an adverse clinical event or an adverse clinical outcome in a patient with a cardiovascular disorder. Risk factors for cardiovascular disease include smoking, adverse lipid profiles, elevated lipids or cholesterol, diabetes, hypertension, hypercoagulable states, elevated homocysteine levels, and lack of exercise. Carrying a particular polymorphic allele is a risk factor for a particular cardiovascular disorder, and is associated with an increased risk of the particular disorder.

"Small molecule" as used herein, is meant to refer to a composition, which has a molecular weight of less than about 5 kD and most preferably less than about 4 kD. Small molecules can be nucleic acids, peptides, peptidomimetics, carbohydrates, lipids or other organic or inorganic molecules.

As used herein, the term "specifically hybridizes" or "specifically detects" refers to the ability of a nucleic acid molecule to hybridize to at least approximately 6 consecutive nucleotides of a sample nucleic acid.

"Stenosis," as understood herein refers to a narrowing of an artery as seen in occlusive disorder or in restenosis. Stenosis can be accompanied by those symptoms reflecting a decrease in blood flow past the narrowed arterial segment, in which case the disorder giving rise to the stenosis is termed a disease (i.e., occlusive disease or restenosis disease). Stenosis can exist asymptomatically in a vessel, to be detected only by a diagnostic intervention such as an angiography or a vascular lab study.

"Transcriptional regulatory sequence" is a generic term used throughout the specification to refer to DNA sequences, such as initiation signals, enhancers, and promoters, which induce or control transcription of protein coding sequences with which they are operably linked.

As used herein, the term "transgene" means a nucleic acid sequence (encoding, e.g., one of the IL-1 polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of an IL-1 polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques. The term is intended to include all progeny generations. Thus, the founder animal and all F1, F2, F3, and so on, progeny thereof are included.

The term "treating" as used herein is intended to encompass curing as well as ameliorating at least one symptom of a disease or at least one abnormality associated with a disorder. Treating a cardiovascular disorder can take place by administering a cardiovascular disorder therapeutic. Treating a cardiovascular disorder can also take place by modifying risk factors that are related to the cardiovascular disorder.

A "treatment plan" refers to at least one intervention undertaken to modify the effect of a risk factor upon a patient. A treatment plan for a cardiovascular disorder or disease can address those risk factors that pertain to cardiovascular disorders or diseases. A treatment plan can include an intervention that focuses on changing patient behavior, such as stopping smoking. A treatment plan can include an intervention whereby a therapeutic agent is administered to a patient. As examples, cholesterol levels can be lowered with proper medication, and diabetes can be controlled with insulin. Nicotine addiction can be treated by withdrawal medications. A treatment plan can include an intervention that is diagnostic. The presence of the risk factor of hypertension, for example, can give rise to a diagnostic intervention whereby the etiology of the hypertension is determined. After the reason for the hypertension is identified, further treatments may be administered.

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

4.2 General

The kits and methods of the present invention rely at least in part upon the novel finding that there is an association of patterns of alleles at four polymorphic loci in the IL-1 gene cluster with cardiovascular disorders. These patterns are referred to herein patterns 1, 2 and 3. Pattern 1 comprises an allelic pattern including allele 2 of IL-1A (+4845) or IL-1B (+3954) and allele 1 of IL-1B (−511) or IL-1RN (+2018), or an allele that is in linkage disequilibrium with one of the aforementioned allele. In a preferred embodiment, this allelic pattern permits the diagnosis of fragile plaque disorder. Pattern 2 comprises an allelic pattern including allele 2 of IL-1B (−511) or IL-1RN (+2018) and allele 1 of IL-1A (+4845) or IL-1B (+3954), or an allele that is in linkage disequilibrium with one of the aforementioned alleles. In a preferred embodiment, this allelic pattern permits the diagnosis of fragile plaque disorder. Pattern 3 comprises an allelic pattern including allele 1 of IL-1A (+4845) or allele 1 of IL-1B (+3954), and allele 1 of IL-1B (−511) or allele 1 of IL-1RN (+2018), or an allele that is in linkage disequilibrium with one of the aforementioned alleles. In a preferred embodiment, this allelic pattern permits the diagnosis of a restenosis disorder. In one aspect, the present invention provides novel methods and kits for determining whether a subject has a cardiovascular disorder. In one aspect, the invention discloses a method and a kit for determining whether a subject has a fragile plaque disorder. In one aspect, the invention discloses a method and a kit for determining whether a subject has an occlusive disorder. In one aspect, the invention discloses a method and a kit for determining whether a subject has a restenosis disorder.

Figure 2:
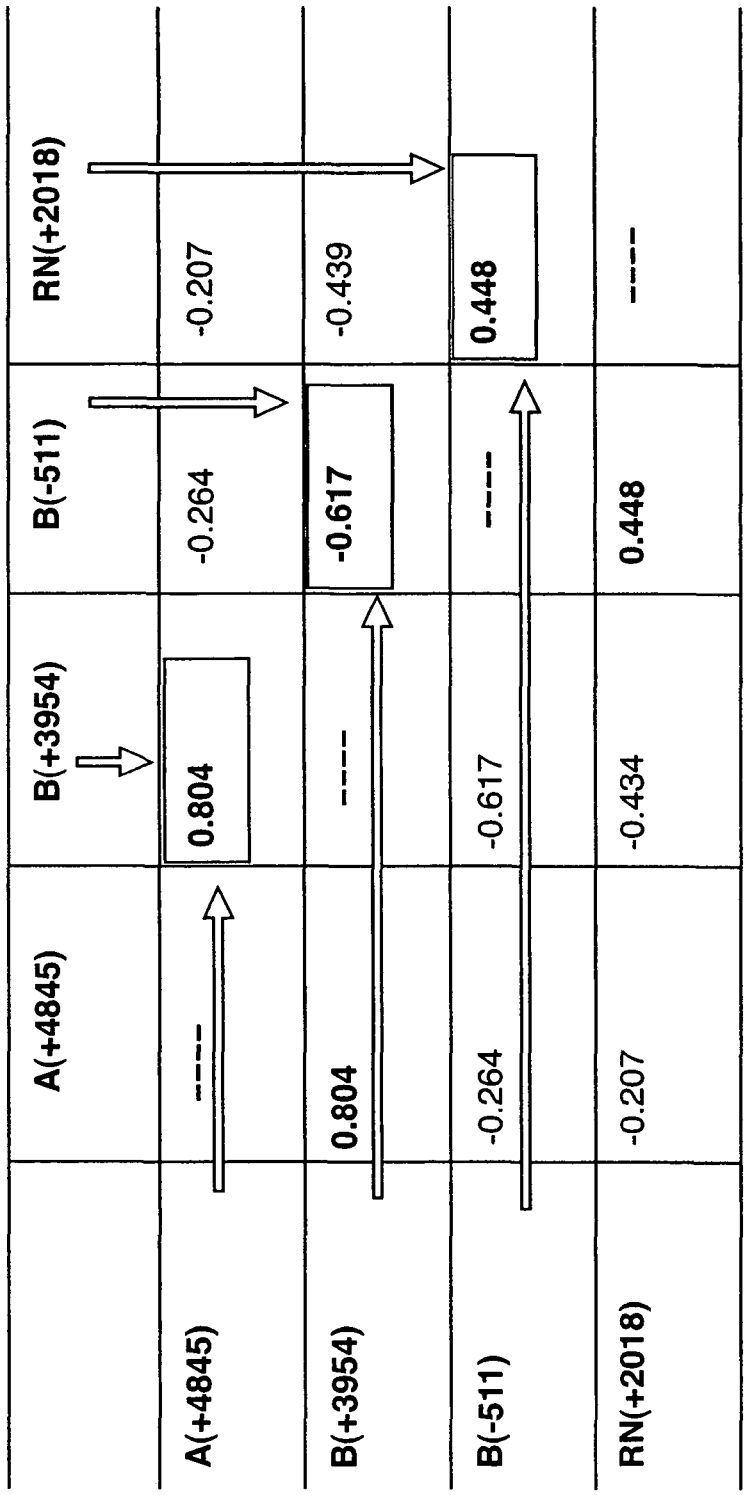
FIG. 2 shows a table of disequilibrium values within the IL-1 gene cluster.
Figure 3:
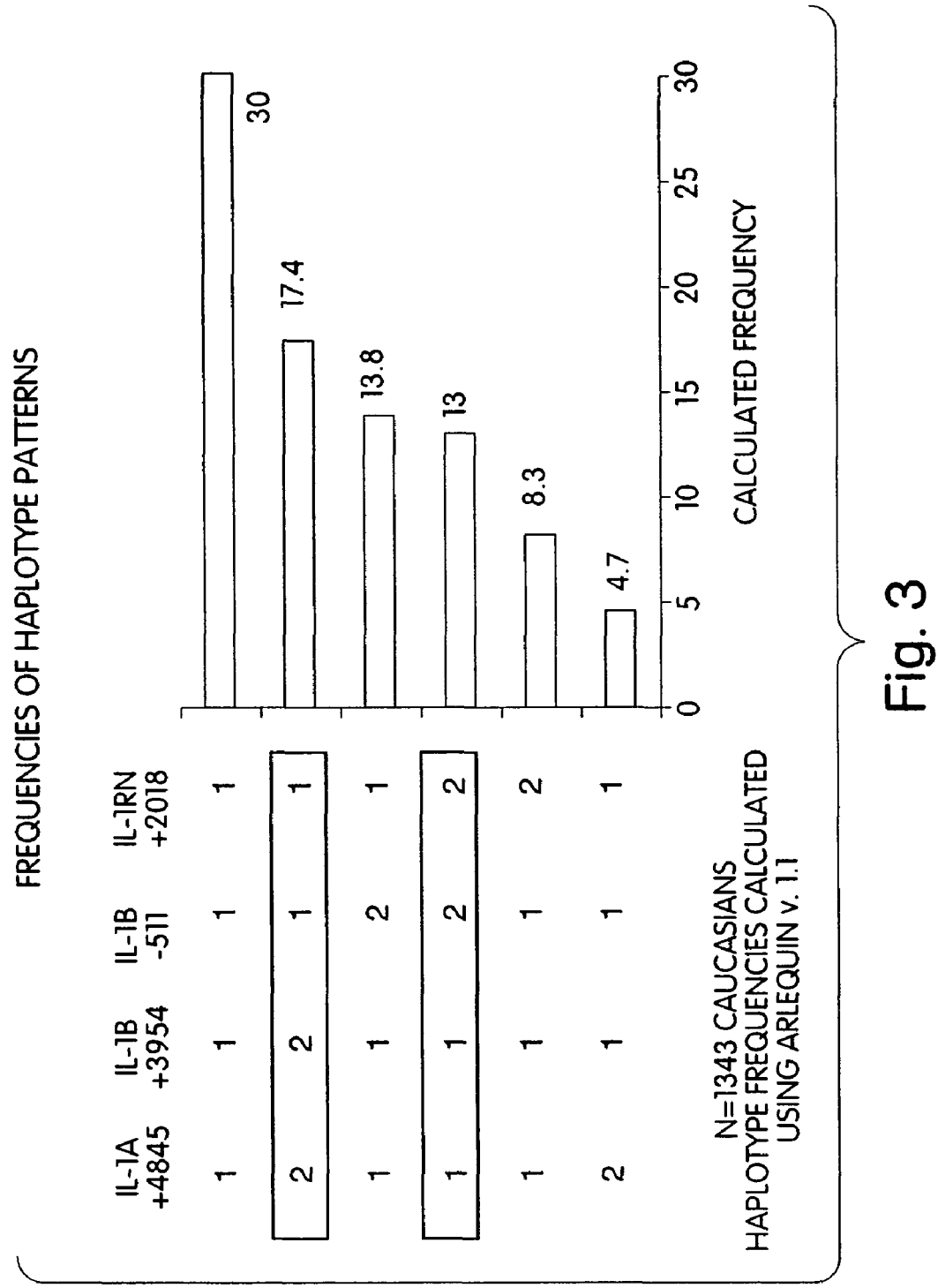
FIG. 3 presents a bar graph showing frequencies of haplotype patterns.

Genes for IL-1α, IL-1β and IL-1RN are located in a cluster on chromosome 2, as shown in FIG. 1. Certain genes at the IL-1 locus are understood to be in linkage disequilibrium, as shown in FIG. 2. Furthermore, as FIG. 3 illustrates, patterns of haplotypes can be identified, and their frequencies in populations can be ascertained. The three haplotype patterns, patterns 1, 2 and 3, may be defined by four polymorphic loci in the IL-1 gene cluster as shown in Table 1.

TABLE 1

| Haplotypes | IL-1A (+4845) | IL-1B (+3954) | IL-1B (−511) | IL-1RN (+2018) |
|---|---|---|---|---|
| Pattern 1 | Allele 2 | Allele 2 | Allele 1 | Allele 1 |
| Pattern 2 | Allele 1 | Allele 1 | Allele 2 | Allele 2 |
| Pattern 3 | Allele 1 | Allele 1 | Allele 1 | Allele 1 |

Haplotype pattern 1 is associated with fragile plaque disorders. Haplotype pattern 2 is associated with occlusive disorders. Haplotype pattern 3 is associated with restenosis disorders. As discussed above, because these alleles are in linkage disequilibrium with other alleles, the detection of such other linked alleles can also indicate that the subject has or is predisposed to the development of a cardiovascular disorder.

Atherosclerotic plaque that is prone to rupture (fragile plaque, as seen in fragile plaque disorders) has certain structural, cellular, and molecular features. Rupture of the fibrous cap overlaying a vulnerable plaque is the most common cause of coronary thrombosis. Typically fragile plaque has a large lipid core and a thin fibrous cap that is often infiltrated by inflammatory cells. The nature of the lipid forming the core is also of significance; for instance, lipid in the form of cholesterol ester softens the plaque and crystalline cholesterol may have the opposite effect. Furthermore, it is seen that an inflammatory cell infiltrate is a marker of plaque vulnerability. Several factors such as oxidized lipoproteins, infectious agents, or autoantigens, such as heat shock proteins may incite a chronic inflammatory response in an atherosclerotic plaque. Influx of activated macrophages and T lymphocytes into the plaque follows, with subsequent influx of cytokines and matrix-degrading proteins, leading to the weakening of the connective tissue framework of the plaque. Matrix metalloproteinases and certain cytokines are important factors in the pathogenesis of plaque vulnerability. Following the diagnosis of a fragile plaque disorder, therapeutics can be devised to address features of the fragile plaque like the abovementioned.

Figure 4:
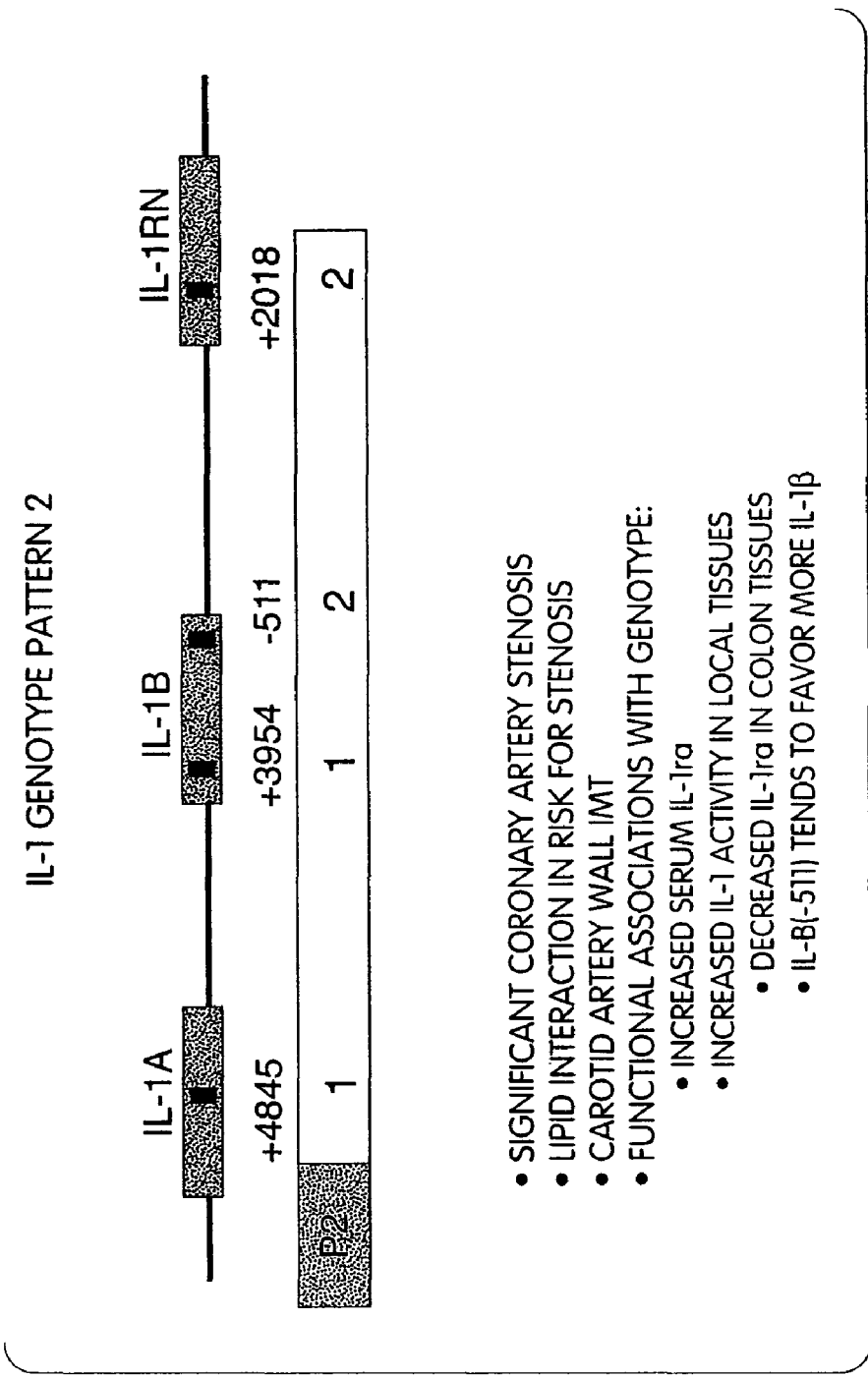
FIG. 4 presents a schematic depiction of the alleles in IL-1 Genotype Pattern 2 and certain of their clinical correlations.

In one embodiment, the present invention discloses the association between significant coronary artery stenosis, increased carotid artery wall intimal-medial thickness and the IL-1 genotype pattern 2. The presence of Pattern 2 can be measured to determine a risk factor for the development of CAD. This pattern, and its pathophysiological correlates, is illustrated in FIG. 4. A clinical trial, whose findings are synopsized on FIG. 5, was conducted to determine the association between a genetic marker and the presence of symptomatic coronary artery stenosis. The results of this clinical trial are depicted in FIG. 6, where about 75% of those patients homozygous for allele 2 at an IL-1RN locus were determined to have significant coronary artery stenosis.

Figure 7:
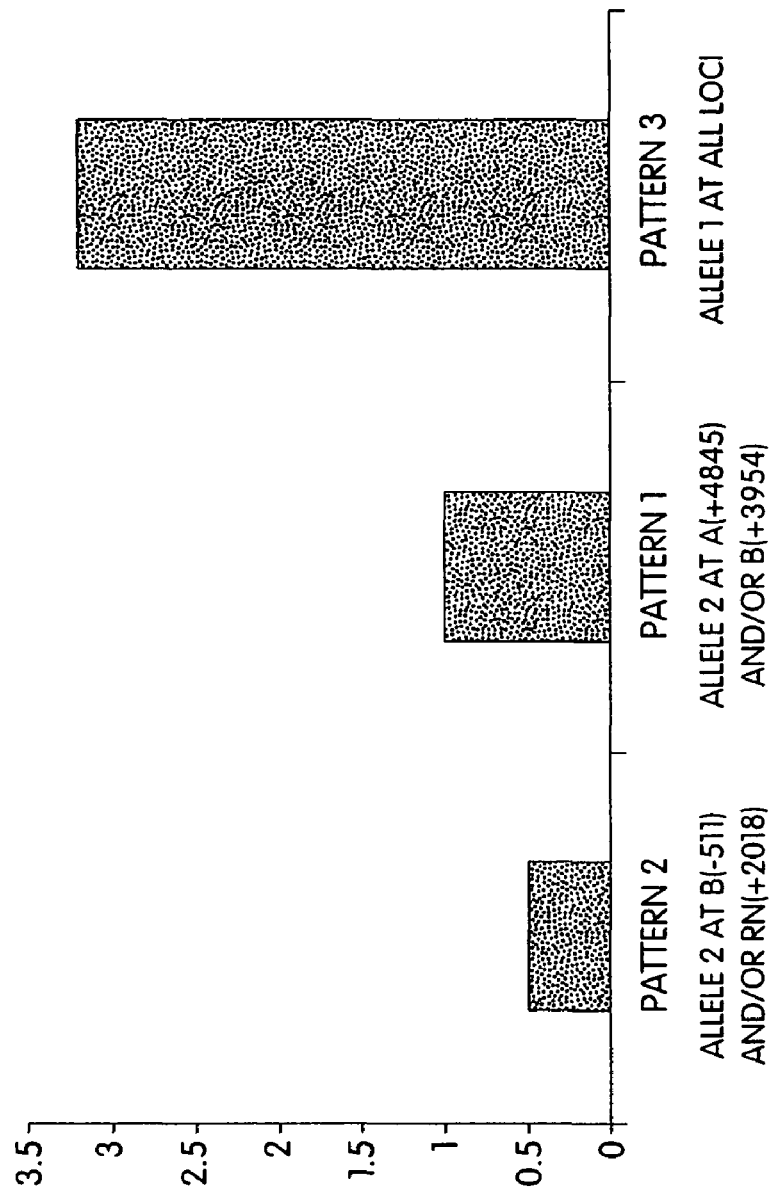
FIG. 7 presents a bar graph showing associations between IL-1 genotype patterns and restenosis.
Figure 8:
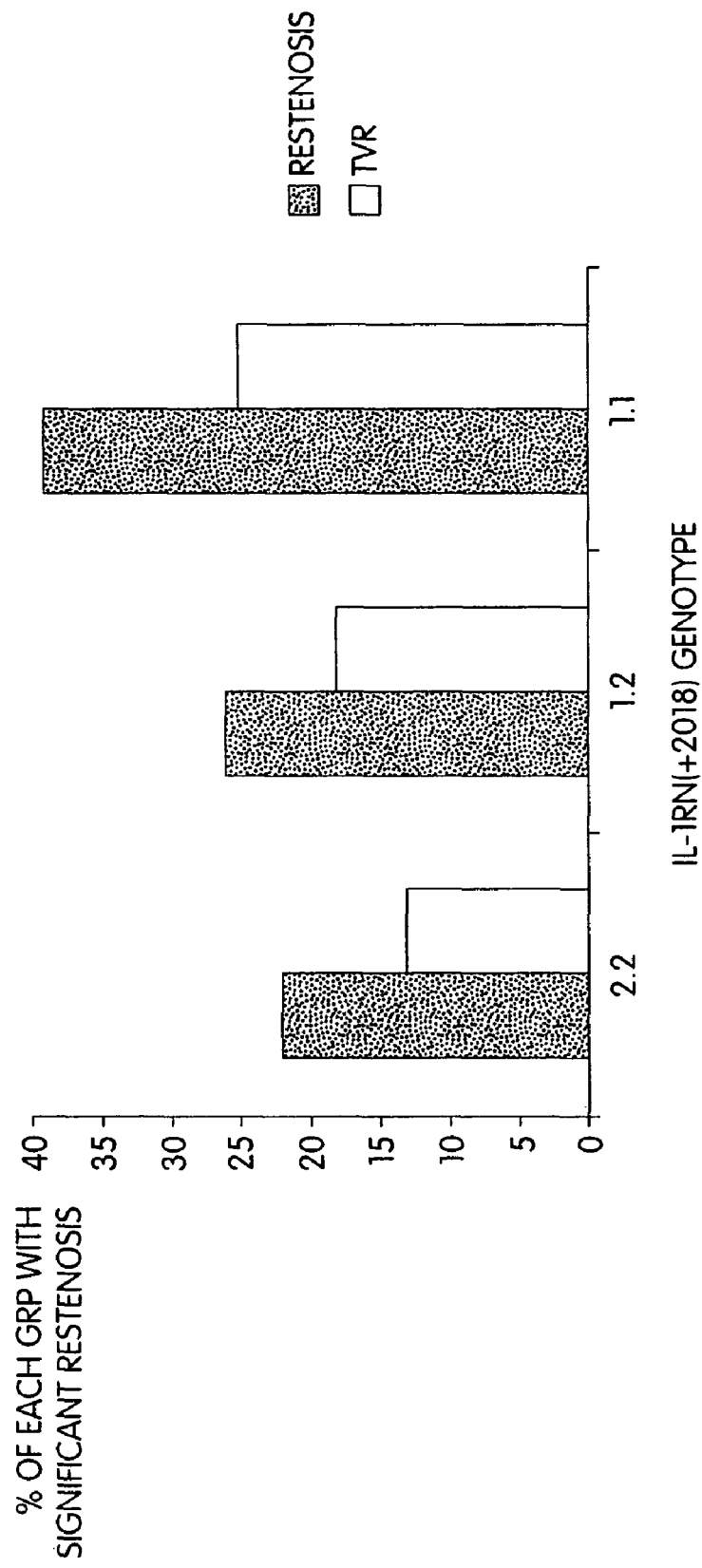
FIG. 8 presents a bar graph showing associations between homozygous and heterozygous allelic patterns at IL-1RN (+2018) locus and restenosis and target vessel revascularization (TVR).

In one embodiment, the present invention discloses the relation between restenosis and the pattern 3 genotype at the IL-1 locus. As shown in FIG. 7, a study shows that the pattern 3 genotype is associated with about a three-fold increase in the risk for restenosis, while the risk is 0.5 for the pattern 2 genotype and 1.0 for the pattern 1 genotype. FIG. 8, depicting data from the same study, shows that about 40% of those subjects homozygous for allele 1 at IL1RN (+2018) have significant restenosis, and 25% have required target vessel revascularization.

It is understood that there may be a relation between the effects of certain risk factors on a patient afflicted with one of the abovementioned cardiovascular disorders and the development of the related disease, and there may be a relation between the effects of risk factors and the progression of the related disease. Diagnosis of the underlying haplotype pattern can guide the clinician in making recommendations or in designing interventions to decrease the impact of the risk factors on the particular disorder or disease.

Figure 9:
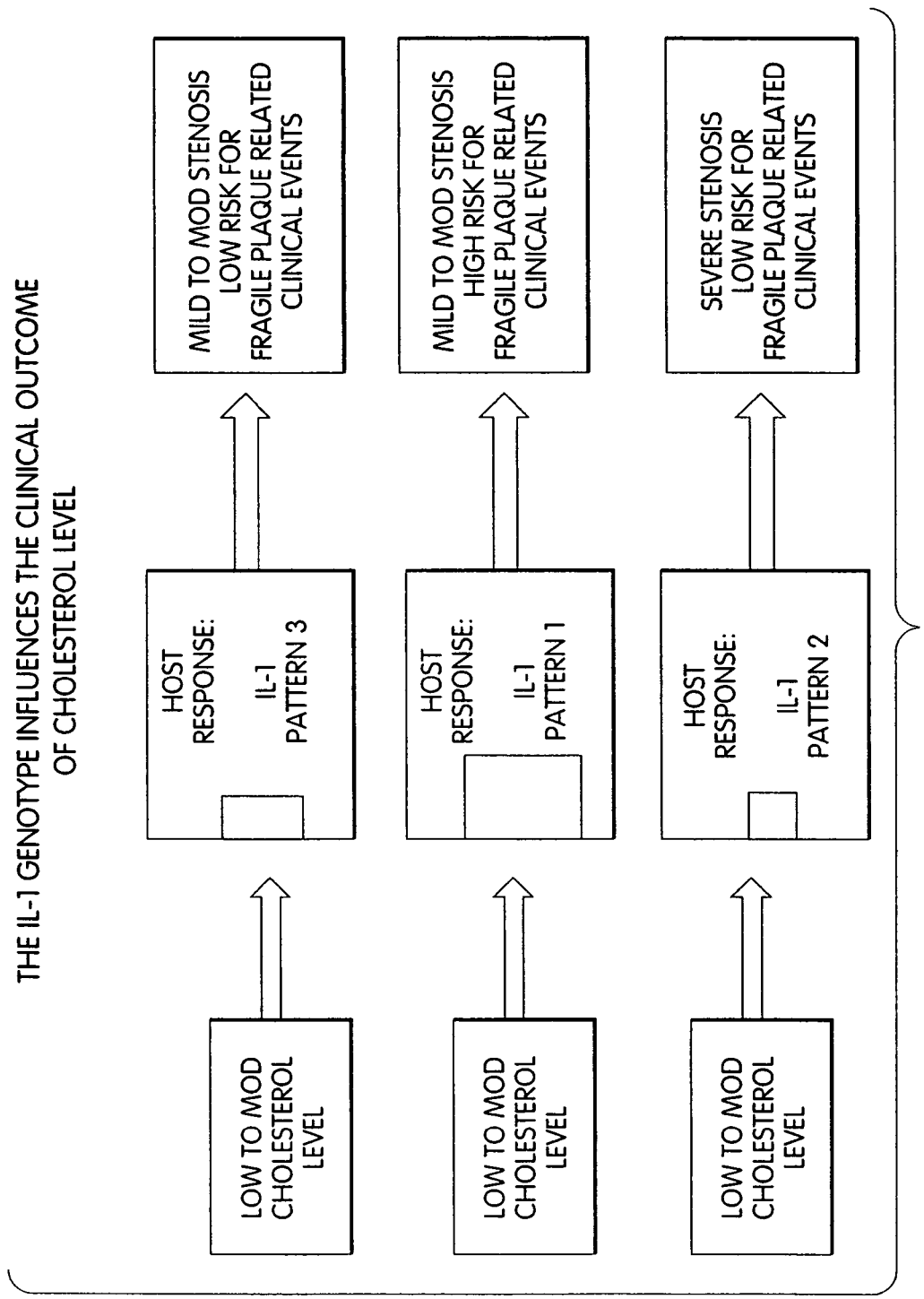
FIG. 9 presents a schematic flow chart of the relations between cholesterol levels, IL-1 patterns and clinical events.
Figure 10:
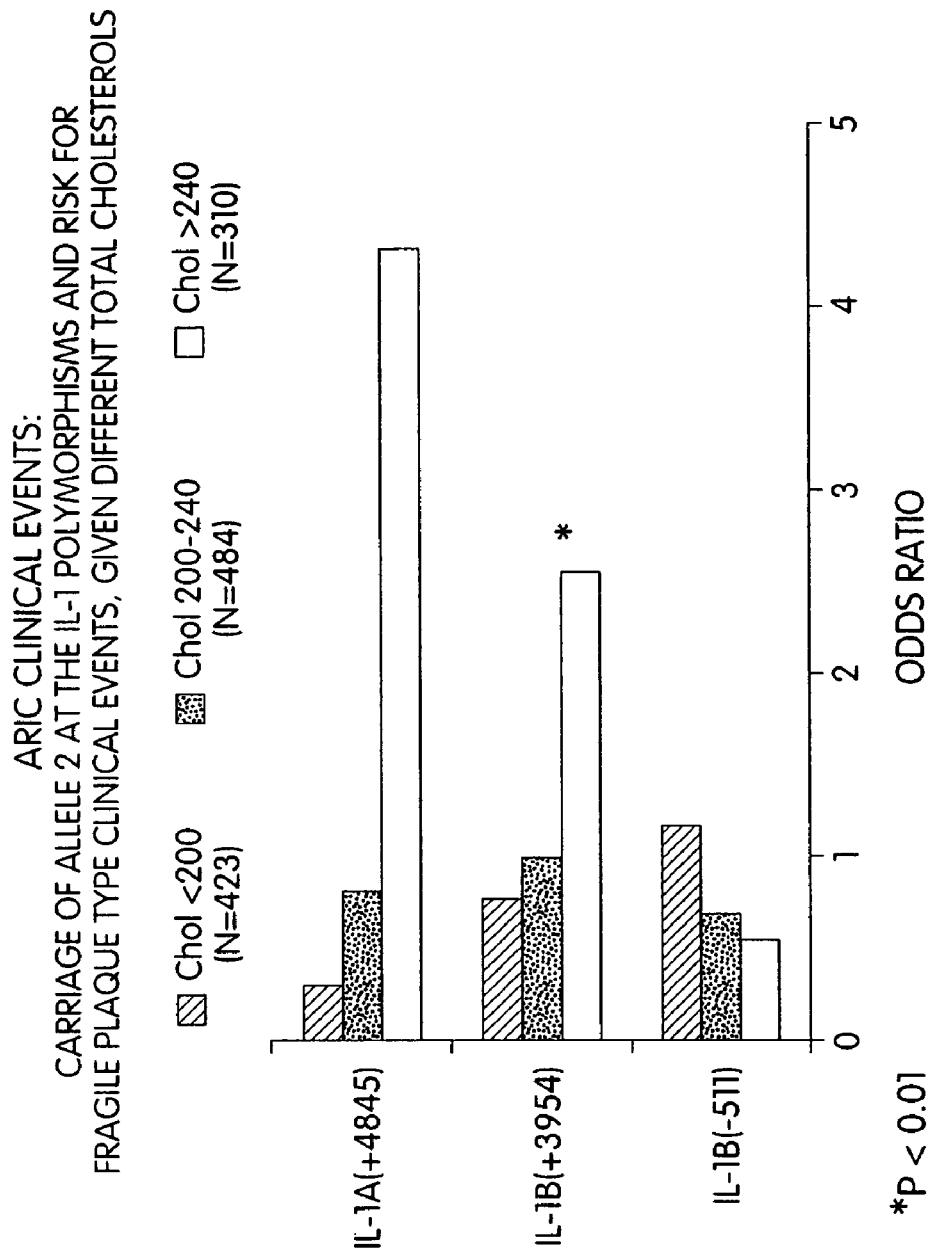
FIG. 10 presents a bar graph showing relationship between IL-1 polymorphisms and risk for fragile plaque type clinical events with different total cholesterol levels.
Figure 11:
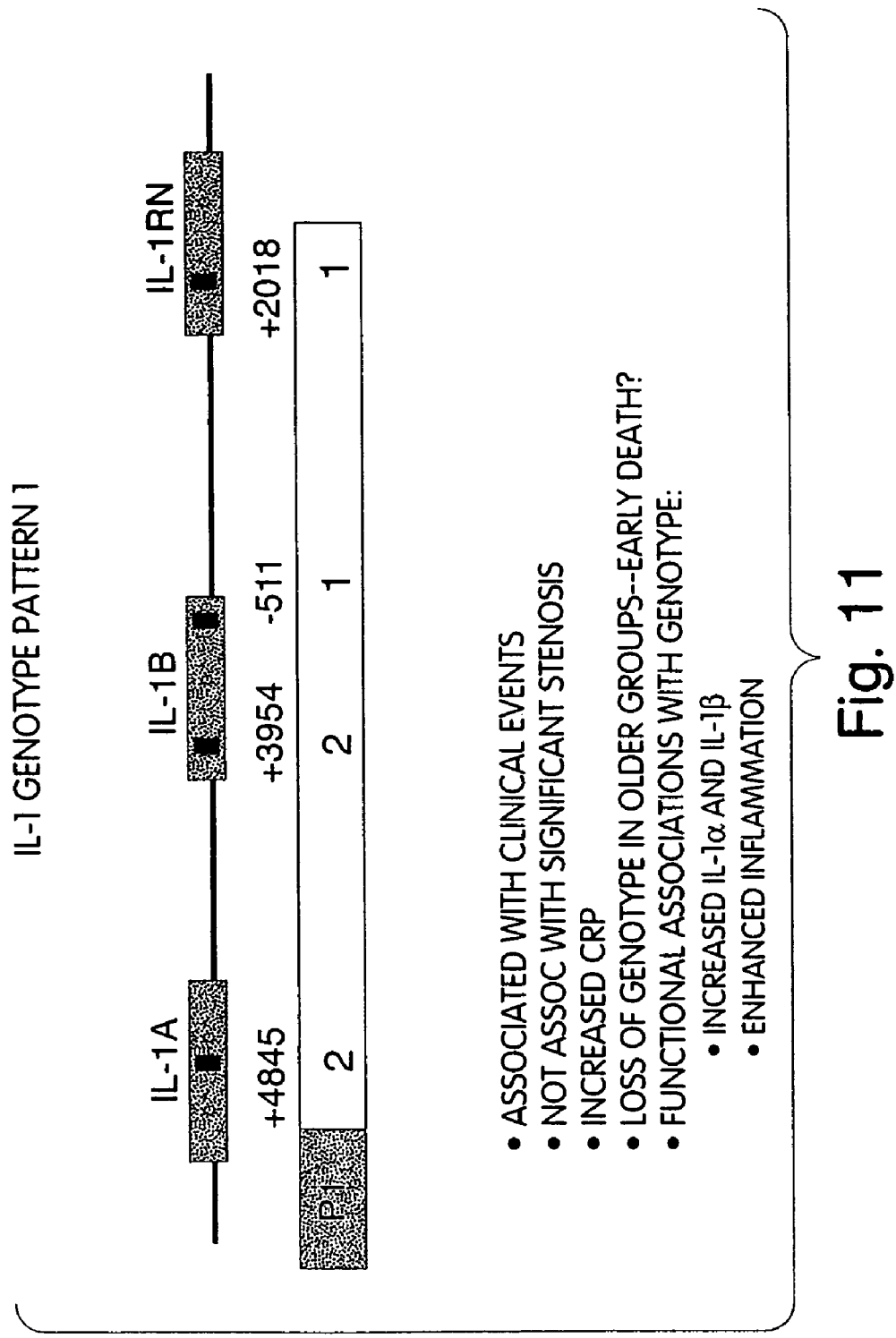
FIG. 11 presents a schematic depiction of the alleles in IL-1 Genotype Pattern 1 and certain of their clinical correlations.

For example, the IL-1 genotype pattern in a patient can be related to the effect of total cholesterol levels on cardiovascular disorders and diseases. The presence of a certain serum cholesterol level in the presence of a certain IL-1 genotype pattern is associated with a statistically determinable risk for coronary occlusive disease and fragile plaque disease. These associations are illustrated schematically in FIG. 9. FIG. 10 summarizes some of the data supporting the associations. The data indicate that the presence of Pattern 1, even in the presence of low serum cholesterol, is a strong predictor of the risk for fragile plaque type events. Fragile plaque type events are also observed in patients with Pattern 2, although there is a strong correlation with the serum cholesterol level. General associations of the IL-1 genotype pattern 2 are summarized schematically in FIG. 11.

Figure 12:
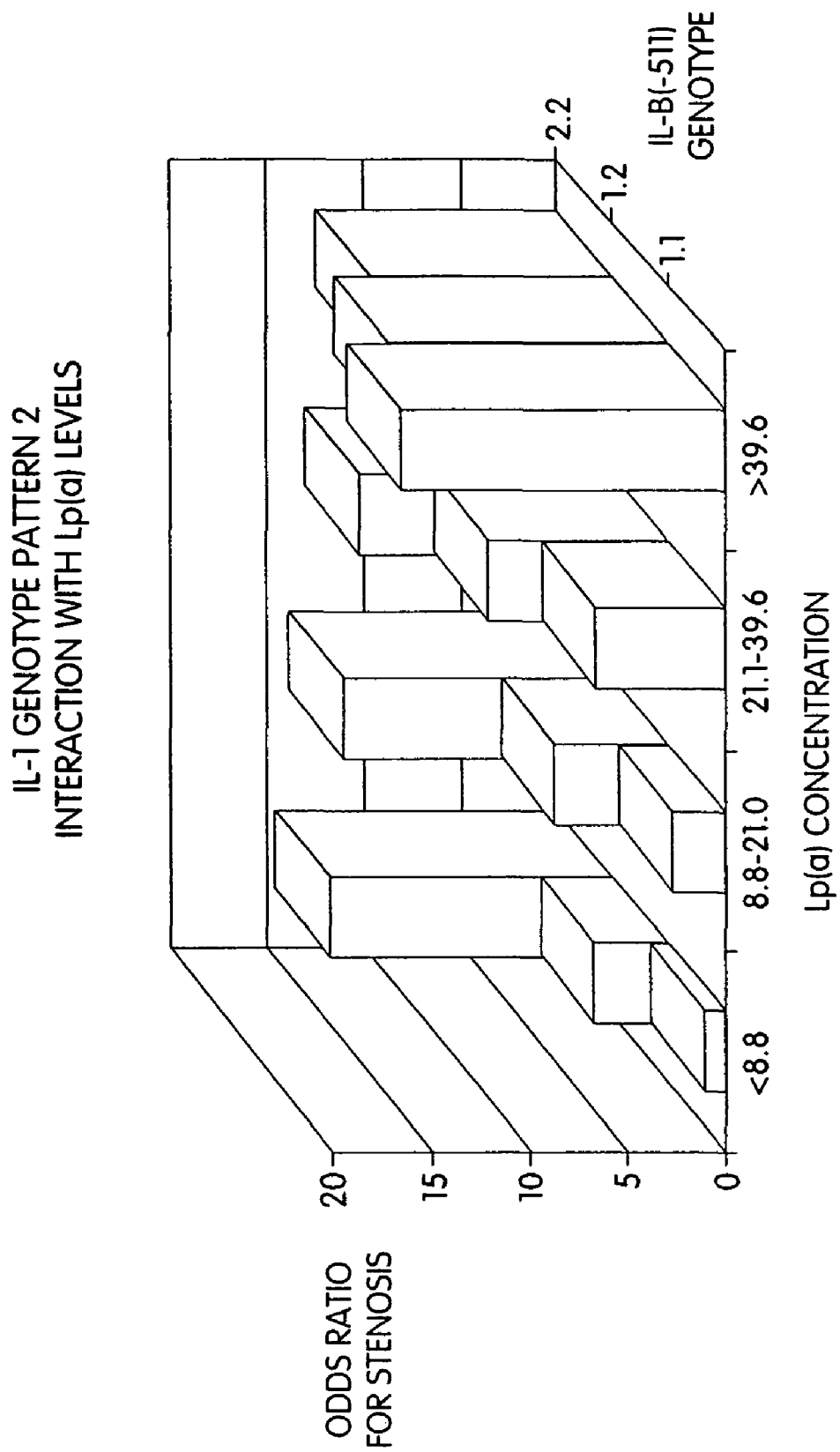
FIG. 12 shows a bar graph relating IL-1 genotype pattern 2 with Lp(a) levels.
Figure 13:
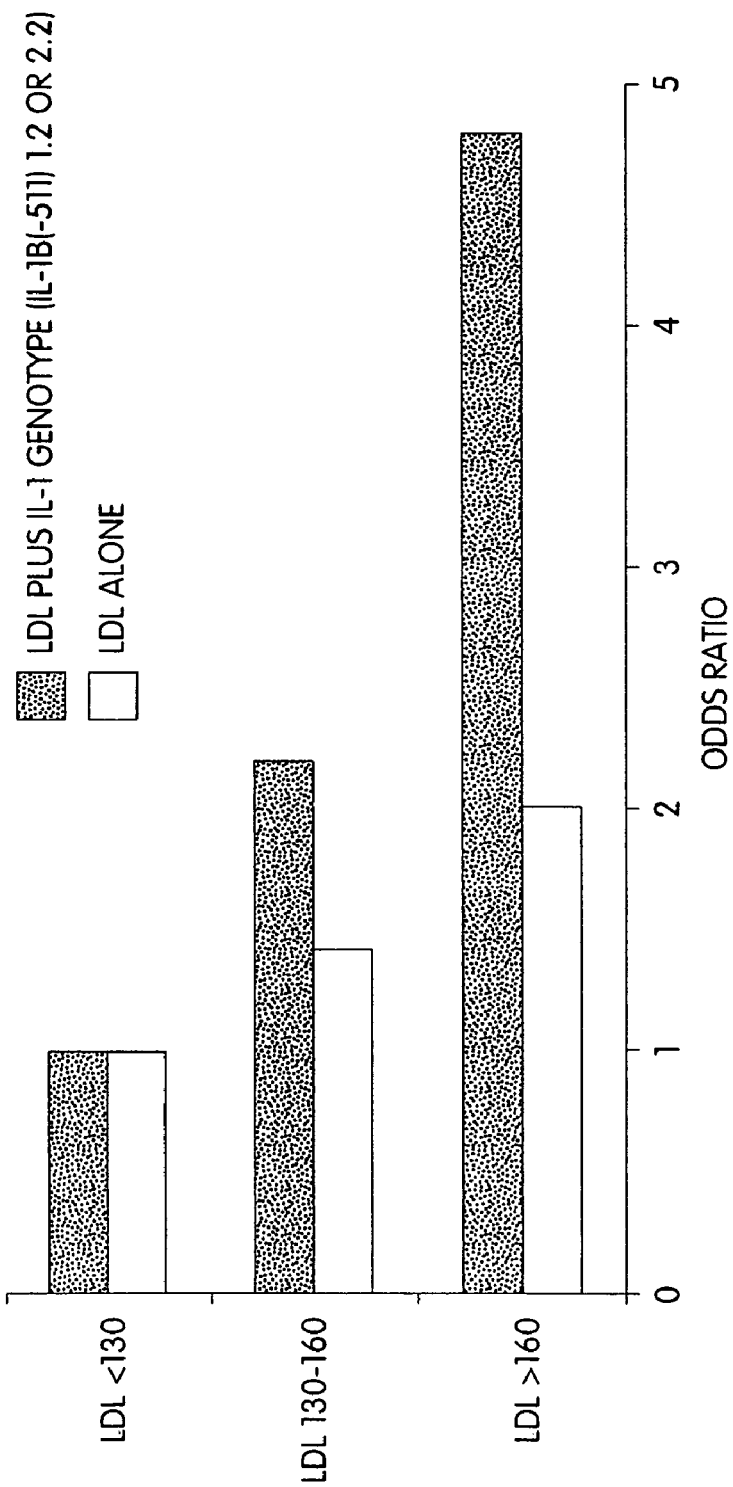
FIG. 13 shows a bar graph relating IL-1 genotype pattern 2 with LDL levels.

Using the methods and kits of the present invention, the Il-1 genotype pattern may be related to the Lp(a) level in a subject to determine an odds ratio for occlusive CAD. It is understood that cholesterol is transported in body fluids in the form of lipoprotein particles. The protein component of these aggregates have specific cell-targeting capabilities. Each lipoprotein particle is classified by density and contains 1) a major species of lipids that is the core, and 2) a specific apolipoprotein that is the shell of the particle. LDL, for example, has a cholesterol core with an apolipoprotein B-100 shell. Lipoprotein (a) [Lp(a)] is a lipoprotein that contains LDL and a protein chain that mimics plasminogen. Lp(a) appears to have atherogenic and prothrombotic effects that interfere with plasminogen and tPA binding to fibrin and stimulate plasminogen activator inhibitor (PAI) synthesis. Studies have shown a relationship between Lp(a) and coronary artery disease (CAD). A determination of the Il-2 genotype pattern versus the concentration of Lp(a) shows the relationship between symptomatic coronary artery stenosis and Lp(a) levels in Pattern 2 patients, a relationship illustrated in FIG. 12. Those patients homozygous for IL-1B (−511) allele 2 have a greatly increased risk for symptomatic stenosis, despite low Lp(a) levels. FIG. 13 shows the relation between elevated LDL and the risk for coronary artery occlusion, indicating the interrelation between Pattern 2 and elevated serum lipid levels.

Figure 14:
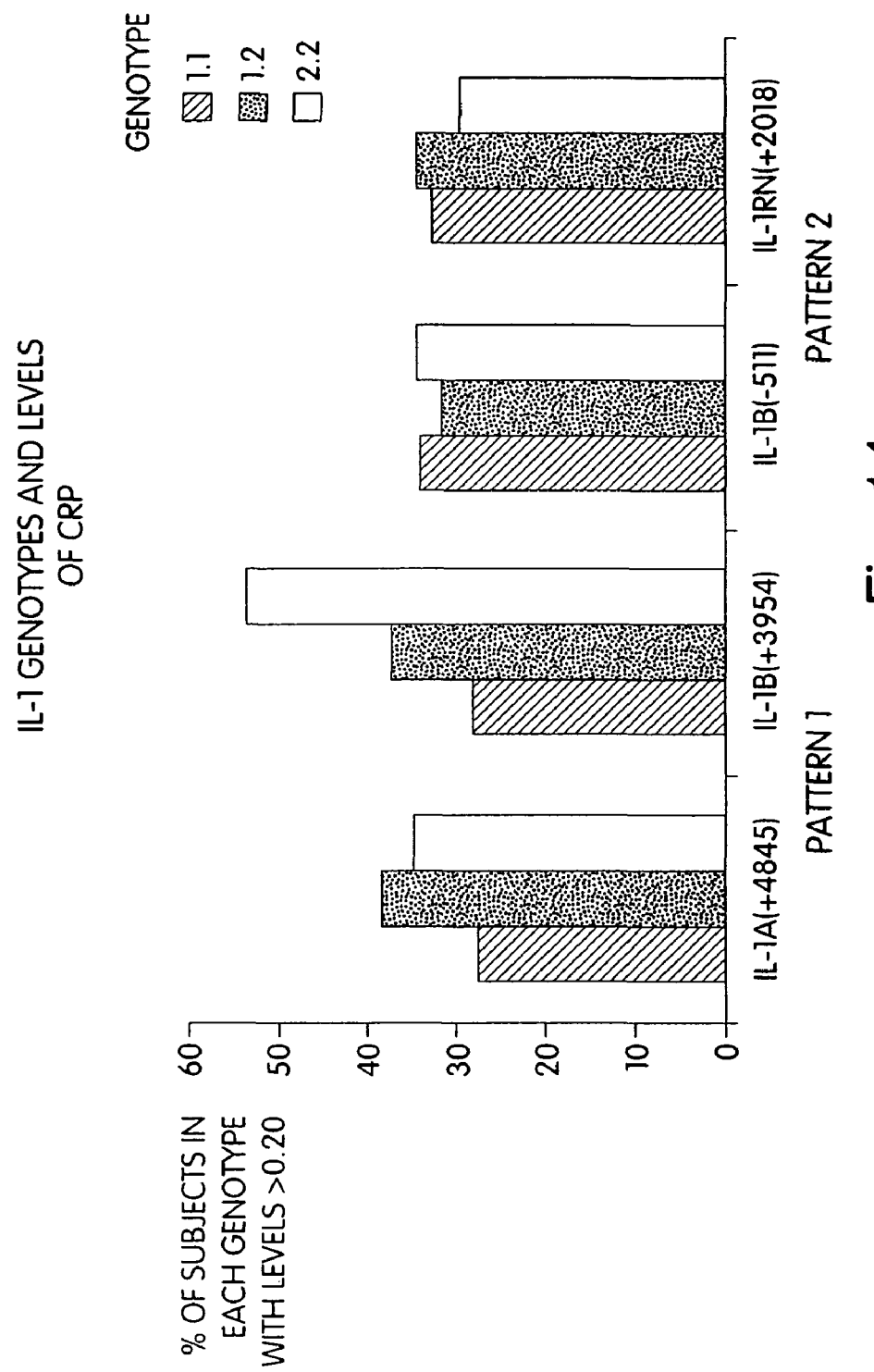
FIG. 14 shows a bar graph illustrating relationships between IL-1 genotypes and levels of C-reactive protein.

The methods and kits of the present invention may be used to relate the level of C-reactive protein (CRP) to the IL-1 genotype pattern. Over 50% of those pattern 1 subjects who were homozygous for allele 2 at IL-1B (+3954) were found to have a CRP greater than 0.20, while those pattern 2 subjects homozygous for allele 1 at IL-1B (+3954) had a CRP greater than 0.20 only about 28% of the time. These data are illustrated in FIG. 14.

4.3 Predictive Medicine

4.3.1. Polymorphisms Associated with Cardio-Vascular Disorders

The present invention is based at least in part, on the identification of alleles that are associated (to a statistically significant extent) with the development of a cardiovascular disorder in subjects. Therefore, detection of these alleles, alone or in conjunction with another means in a subject indicate that the subject has or is predisposed to the development of a cardiovascular disorder. For example, as shown in the following examples, IL-1 polymorphic alleles which are associated with a propensity for developing a coronary artery disorder or other vascular disorders caused by vascular occlusion include allele 2 of IL-1B (−511), allele 2 of IL-1RN (VNTR), allele 2 of IL-1RN (+2018), allele 1 of IL-1A (+4845) or allele 1 of IL-1B (+3954) or an allele that is in linkage disequilibrium with one of the aforementioned alleles.

The present invention also discloses IL-1 polymorphic alleles which are associated with a propensity or a greater risk for cardiovascular diseases caused due to the rupture of fragile plaques. These include allele 2 of IL-1A (+4845), allele 2 of IL-1B (+3954), allele 1 of IL-1B (−511), and allele 1 of IL-1RN (+2018) or an allele that is in linkage disequilibrium with one of the aforementioned alleles. This pattern is also associated with an increased risk for developing severe adult periodontitis.

For example, allele 2 of IL-1B (−511) and allele 2 of IL-1RN (VNTR) are in linkage disequilibrium with one another and with a number of other IL-1 polymorphisms which define the IL-1 (44112332) haplotype (Cox, et al. (1998) Am. J. Hum. Genet. 62: 1180-88). Specifically, the 44112332 haplotype comprises the following genotype:

---
allele 4 of the 222/223 marker of IL-1A
allele 4 of the gz5/gz6 marker of IL-1A
allele 1 of the −889 marker of IL-1A
allele 1 of the +3954 marker of IL-1B
allele 2 of the −511 marker of IL-1B
allele 3 of the gaat.p33330 marker
allele 3 of the Y31 marker
allele 2 of the VNTR marker of IL-1RN
---

Thus, in alternative embodiments of the present invention, genotyping analysis at the 222/223 marker of IL-1A, the gz5/gz6 marker of IL-1A, the −889 marker of IL-1A, the +3954 marker of IL-1B, the gaat.p33330 marker of the IL-1B/IL-1RN intergenic region, or the Y31 marker of the IL-1B/IL-1RN intergenic region is determined, and the presence of allele 4 of the 222/223 marker of IL-1A, allele 4 of the gz5/gz6 marker of IL-1A, allele 1 of the −889 marker of IL-1A, allele 1 of the +3954 marker of IL-1B, allele 3 of the gaat.p33330 marker, or allele 3 of the Y31 marker is indicative of an increased likelihood of developing a cardiovascular disorder, particularly disorders caused by occlusion of the arteries. In certain embodiments, diagnosing a propensity for an occlusive disease can lead to modification of lifestyle factors associated with increased incidence of occlusive clinical events, or can result in the introduction of therapeutic modalities to reduce the risk of occlusive symptoms or signs. In other embodiments, diagnosing a propensity for an occlusive disease can alert the clinician to explanations for otherwise difficult-to-diagnose diseases such as intestinal angina, renovascular hypertension and others, situations where arterial stenosis may be responsible for the symptoms and signs.

In addition, allele 2 of the IL-1RN (+2018) polymorphism (Clay et al. (1996) Hum Genet 97: 723-26), also referred to as exon 2 (8006) (GenBank:X64532 at 8006) is known to be in linkage disequilibrium with allele 2 of the IL-1RN (VNTR) polymorphic locus, which in turn is a part of the 44112332 human haplotype. Thus, allele 2 of the IL-1RN (+2018) locus (i.e. C at +2018), is an allelic variant associated with the 44112332 haplotype and therefore provides an alternative target for prognostic genotyping analysis to determine an individual's likelihood of developing a vascular disorder. Similarly, three other polymorphisms in an IL-1RN alternative exon (Exon 1ic, which produces an intracellular form of the gene product) are also in linkage disequilibrium with allele 2 of IL-1RN (VNTR) (Clay et al. (1996) Hum Genet 97: 723-26). These include: the IL-1RN exon 1ic (1812) polymorphism (GenBank:X77090 at 1812); the IL-1RN exon 1ic (1868) polymorphism (GenBank:X77090 at 1868); and the IL-1RN exon 1ic (1887) polymorphism (GenBank:X77090 at 1887). Furthermore yet another polymorphism in the promoter for the alternatively spliced intracellular form of the gene, the Pic (1731) polymorphism (GenBank:X77090 at 1731), is also in linkage disequilibrium with allele 2 of the IL-1RN (VNTR) polymorphic locus (Clay et al. (1996) Hum Genet 97: 723-26). The corresponding sequence alterations for each of these IL-1RN polymorphic loci is shown below.

| Allele # | Exon 2 (+2018 of IL-1RN) | Exon 1ic −1 (1812 of GB: X77090) | Exon 1ic −2 (1868 of GB: X77090 | Exon 1ic −3 (1887 of GB: X77090) | Pic (1731 of GB: X77090) |
|---|---|---|---|---|---|
| 1 | T | G | A | G | G |
| 2 | C | A | G | C | A |

For each of these polymorphic loci, the allele 2 sequence variant has been determined to be in linkage disequilibrium with allele 2 of the IL-1RN (VNTR) locus (Clay et al. (1996) Hum Genet 97: 723-26).

Similarly, the 33221461, which is associated with an increased risk for developing fragile plaque diseases comprises the following genotype:

---
allele 3 of the 222/223 marker of IL-1A
allele 3 of the gz5/gz6 marker of IL-1A
allele 2 of the −889 marker of IL-1A
allele 2 of the +3954 marker of IL-1B
allele 1 of the −511 marker of IL-1B
allele 4 of the gaat.p33330 marker
allele 6 of the Y31 marker
allele 1 of +2018 of IL-1RN
allele 2 of +4845 of IL-1A
allele 1 of the VNTR marker of IL-1RN
---

In alternative embodiments of the invention, genotyping analysis at the −889 marker of IL-1A, the gaat.p33330 marker of the IL-1B/IL-1RN intergenic region, the Y31 marker of the IL-1B/IL-1RN intergenic region is determined, and the presence of allele 1 of the −899 marker of the IL-1A, allele 4 of the gaat.p3330 marker, or allele 6 of the Y31 marker is indicative of cardio-vascular disorders, particularly of an increased risk for fragile plaque disorders. These disorders are understood to lead to clinical events via thrombosis and embolization. Often the clinical event is unheralded by previous signs of ischemia. Chronic ischemia, as disclosed herein, is associated with occlusive cardiovascular disease rather than with fragile plaque disease. Early detection for the propensity for a catastrophic clinical event would be a significant addition to the current diagnostic armamentarium. A fragile plaque clinical event in the cerebrovascular circulation can cause a stroke or CVA by blocking cerebral vessels and causing acute ischemia that can lead to irreversible brain infarction. A fragile plaque clinical event in the myocardial circulation can cause a myocardial infarction by blocking coronary vessels and causing acute ischemia that can lead to irreversible myocardial damage. A fragile plaque clinical event in the non-cerebral peripheral vasculature can lead to sudden onset of ischemia leading to gangrene and tissue loss. Since these fragile plaque clinical events may ensue without prior warning, the identification of the genotype associated with increased risk can lead to increased clinical monitoring in these at-risk subjects, with earlier and more extensive diagnostic or therapeutic interventions. In another embodiment these are also indicative of increased risk for developing severe adult periodontitis. In yet another embodiment, the presence of severe adult periodontitis is indicative of an increased risk for fragile plaque disease.

In addition to the allelic patterns described above, as described herein, one of skill in the art can readily identify other alleles (including polymorphisms and mutations) that are in linkage disequilibrium with an allele associated with a cardio-vascular disorder. For example, a nucleic acid sample from a first group of subjects without a cardio vascular disorder can be collected, as well as DNA from a second group of subjects with a cardio vascular disorder. The nucleic acid sample can then be compared to identify those alleles that are over-represented in the second group as compared with the first group, wherein such alleles are presumably associated with a cardio vascular disorder. Alternatively, alleles that are in linkage disequilibrium with a cardiovascular disorder associated allele can be identified, for example, by genotyping a large population and performing statistical analysis to determine which alleles appear more commonly together than expected. Preferably the group is chosen to be comprised of genetically related individuals. Genetically related individuals include individuals from the same race, the same ethnic group, or even the same family. As the degree of genetic relatedness between a control group and a test group increases, so does the predictive value of polymorphic alleles which are ever more distantly linked to a disease-causing allele. This is because less evolutionary time has passed to allow polymorphisms which are linked along a chromosome in a founder population to redistribute through genetic cross-over events. Thus race-specific, ethnic-specific, and even family-specific diagnostic genotyping assays can be developed to allow for the detection of disease alleles which arose at ever more recent times in human evolution, e.g., after divergence of the major human races, after the separation of human populations into distinct ethnic groups, and even within the recent history of a particular family line.

Linkage disequilibrium between two polymorphic markers or between one polymorphic marker and a disease-causing mutation is a meta-stable state. Absent selective pressure or the sporadic linked reoccurrence of the underlying mutational events, the polymorphisms will eventually become disassociated by chromosomal recombination events and will thereby reach linkage equilibrium through the course of human evolution. Thus, the likelihood of finding a polymorphic allele in linkage disequilibrium with a disease or condition may increase with changes in at least two factors: decreasing physical distance between the polymorphic marker and the disease-causing mutation, and decreasing number of meiotic generations available for the dissociation of the linked pair. Consideration of the latter factor suggests that, the more closely related two individuals are, the more likely they will share a common parental chromosome or chromosomal region containing the linked polymorphisms and the less likely that this linked pair will have become unlinked through meiotic cross-over events occurring each generation. As a result, the more closely related two individuals are, the more likely it is that widely spaced polymorphisms may be co-inherited. Thus, for individuals related by common race, ethnicity or family, the reliability of ever more distantly spaced polymorphic loci can be relied upon as an indicator of inheritance of a linked disease-causing mutation.

The oligonucleotides present in one embodiment of a kit according to the present invention may be used for amplification of the region of interest or for direct allele specific oligonucleotide (ASO) hybridization to the markers in question. Thus, the oligonucleotides may either flank the marker of interest (as required for PCR amplification) or directly overlap the marker (as in ASO hybridization). Examples of appropriate primers for use in the above described detection methods, include:

```
                                          (SEQ ID NO. 1)
        5'-CTCAGCAACACTCCTAT-3';

(SEQ ID NO. 2)
        5'-TCCTGGTCTGCAGGTAA-3';
``` which can be used to amplify and type the human IL-1RN (VNTR) polymorphic locus;

```
                                          (SEQ ID NO. 3)
    5'-CTA TCT GAG GAA CAA CCA ACT AGT AGC-3';

(SEQ ID NO. 4)
    5'-TAG GAC ATT GCA CCT AGG GTT TGT-3';
``` which can be used to amplify and type the human IL-1RN (+2018) polymorphic locus;

```
                                          (SEQ ID No: 5)
        5' TGGCATTGATCTGGTTCATC 3';

(SEQ ID No: 6)
        5' GTTTAGGAATCTTCCCACTT 3';
``` which can be used to amplify and type the human IL-1B (−511) polymorphic locus;

```
                                          (SEQ ID NO: 7)
    5' CTC AGG TGT CCT CGA AGA AAT CAA A 3';

(SEQ ID NO: 8)
    5' GCT TTT TTG CTG TGA GTC CCG 3'
``` which can be used to amplify and type the human IL-1B (+3954) polymorphic locus; and

```
                                              (SEQ ID NO: 9)
    5' ATG GTT TTA GAA ATC ATC AAG CCT AGG GCA 3'

(SEQ ID NO: 10)
    3' AAT GAA AGG AGG GGA GGA TGA CAG AAA TGT 3'
``` which can be used to amplify and type the human IL-1A (+4845) polymorphic locus.

Appropriate probes may be designed to hybridize to a specific gene of the IL-1 locus, such as IL-1A, IL-1B or IL-1RN or a related gene. Alternatively, these probes may incorporate other regions of the relevant genomic locus, including intergenic sequences. Indeed the IL-1 region of human chromosome 2 spans some 400,000 base pairs and, assuming an average of one single nucleotide polymorphism every 1,000 base pairs, includes some 400 SNPs loci alone. Yet other polymorphisms available for use with the immediate invention are obtainable from various public sources. For example, the human genome database collects intragenic SNPs, is searchable by sequence and currently contains approximately 2,700 entries. Also available is a human polymorphism database maintained by the Massachusetts Institute of Technology (MIT SNP database). From such sources SNPs as well as other human polymorphisms may be found.

For example, examination of the IL-1 region of the human genome in any one of these databases reveals that the IL-1 locus genes are flanked by a centromere proximal polymorphic marker designated microsatellite marker AFM220ze3 at 127.4 cM (centiMorgans) (see GenBank Acc. No. Z17008) and a distal polymorphic marker designated microsatellite anchor marker AFMO87xa1 at 127.9 cM (see GenBank Acc. No. Z16545). These human polymorphic loci are both CA dinucleotide repeat microsatellite polymorphisms, and, as such, show a high degree of heterozygosity in human populations. For example, one allele of AFM220ze3 generates a 211 bp PCR amplification product with a 5' primer of the sequence TGTACCTAAGCCCACCCTTTAGAGC (SEQ ID No. 14) and a 3' primer of the sequence TGGCCTCCAGAAACCTCCAA (SEQ ID No. 15). Furthermore, one allele of AFMO87xa1 generates a 177 bp PCR amplification product with a 5' primer of the sequence GCTGATATTCTGGTGGGAAA (SEQ ID No. 16) and a 3' primer of the sequence GGCAAGAGCAAAACTCTGTC (SEQ ID No. 17). Equivalent primers corresponding to unique sequences occurring 5' and 3' to these human chromosome 2 CA dinucleotide repeat polymorphisms will be apparent to one of skill in the art. Reasonable equivalent primers include those which hybridize within about 1 kb of the designated primer, and which further are anywhere from about 17 bp to about 27 bp in length. A general guideline for designing primers for amplification of unique human chromosomal genomic sequences is that they possess a melting temperature of at least about 50° C., wherein an approximate melting temperature can be estimated using the formula $T_{melt}=[2\times(\# \text{ of A or T})+4\times(\# \text{ of G or C})]$.

A number of other human polymorphic loci occur between these two CA dinucleotide repeat polymorphisms and provide additional targets for determination of a cardio-vascular disorder prognostic allele in a family or other group of genetically related individuals. For example, the National Center for Biotechnology Information web site lists a number of polymorphism markers in the region of the IL-1 locus and provides guidance in designing appropriate primers for amplification and analysis of these markers.

Accordingly, the nucleotide segments of the invention may be used for their ability to selectively form duplex molecules with complementary stretches of human chromosome 2 q 12-13 or cDNAs from that region or to provide primers for amplification of DNA or cDNA from this region. The design of appropriate probes for this purpose requires consideration of a number of factors. For example, fragments having a length of between 10, 15, or 18 nucleotides to about 20, or to about 30 nucleotides, will find particular utility. Longer sequences, e.g., 40, 50, 80, 90, 100, even up to full length, are even more preferred for certain embodiments. Lengths of oligonucleotides of at least about 18 to 20 nucleotides are well accepted by those of skill in the art as sufficient to allow sufficiently specific hybridization so as to be useful as a molecular probe. Furthermore, depending on the application envisioned, one will desire to employ varying conditions of hybridization to achieve varying degrees of selectivity of probe towards target sequence. For applications requiring high selectivity, one will typically desire to employ relatively stringent conditions to form the hybrids. For example, relatively low salt and/or high temperature conditions, such as provided by 0.02 M-0.15M NaCl at temperatures of about 50° C. to about 70° C. Such selective conditions may tolerate little, if any, mismatch between the probe and the template or target strand.

Other alleles or other indicia of a vascular disorder can be detected or monitored in a subject in conjunction with detection of the alleles described above, for example, identifying vessel wall thickness (e.g. as measured by ultrasound), or whether the subject smokes, drinks, is overweight, is under stress, has elevated cholesterol or low cholesterol has elevated Lp(a), or exercises.

4.3.2 Detection of Alleles

Many methods are available for detecting specific alleles at human polymorphic loci. The preferred method for detecting a specific polymorphic allele will depend, in part, upon the molecular nature of the polymorphism. For example, the various allelic forms of the polymorphic locus may differ by a single base-pair of the DNA. Such single nucleotide polymorphisms (or SNPs) are major contributors to genetic variation, comprising some 80% of all known polymorphisms, and their density in the human genome is estimated to be on average 1 per 1,000 base pairs. SNPs are most frequently biallelic-occurring in only two different forms (although up to four different forms of an SNP, corresponding to the four different nucleotide bases occurring in DNA, are theoretically possible). Nevertheless, SNPs are mutationally more stable than other polymorphisms, making them suitable for association studies in which linkage disequilibrium between markers and an unknown variant is used to map disease-causing mutations. In addition, because SNPs typically have only two alleles, they can be genotyped by a simple plus/minus assay rather than a length measurement, making them more amenable to automation.

A variety of methods are available for detecting the presence of a particular single nucleotide polymorphic allele in an individual. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

Several methods have been developed to facilitate analysis of single nucleotide polymorphisms. In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46-59 (1993)).

For mutations that produce premature termination of protein translation, the protein truncation test (PTT) offers an efficient diagnostic approach (Roest, et. al., (1993) *Hum. Mol. Genet.* 2:1719-21; van der Luijt, et. al., (1994) *Genomics* 20:1-4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

Any cell type or tissue may be utilized to obtain nucleic acid samples for use in the diagnostics described herein. In a preferred embodiment, the DNA sample is obtained from a bodily fluid, e.g, blood, obtained by known techniques (e.g. venipuncture) or saliva. Alternatively, nucleic acid tests can be performed on dry samples (e.g. hair or skin). When using RNA or protein, the cells or tissues that may be utilized must express an IL-1 gene.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

A preferred detection method is allele specific hybridization using probes overlapping a region of at least one allele of an IL-1 proinflammatory haplotype and having about 5, 10, 20, 25, or 30 nucleotides around the mutation or polymorphic region. In a preferred embodiment of the invention, several probes capable of hybridizing specifically to other allelic variants involved in a cardio-vascular disorder are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

These techniques may also comprise the step of amplifying the nucleic acid before analysis. Amplification techniques are known to those of skill in the art and include, but are not limited to cloning, polymerase chain reaction (PCR), polymerase chain reaction of specific alleles (ASA), ligase chain reaction (LCR), nested polymerase chain reaction, self sustained sequence replication (Guatelli, J. C. et al., 1990, Proc. Natl. Acad. Sci. USA 87:1874-1878), transcriptional amplification system (Kwoh, D. Y. et al., 1989, Proc. Natl. Acad. Sci. USA 86:1173-1177), and Q-Beta Replicase (Lizardi, P. M. et al., 1988, Bio/Technology 6:1197).

Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize 5' and 3' to at least one allele of an IL-1 proinflammatory haplotype under conditions such that hybridization and amplification of the allele occurs, and (iv) detecting the amplification product. These detection schemes are especially useful for the detection of nucleic acid molecules if such molecules are present in very low numbers.

In a preferred embodiment of the subject assay, the allele of an IL-1 proinflammatory haplotype is identified by alterations in restriction enzyme cleavage patterns. For example, sample and control DNA is isolated, amplified (optionally), digested with one or more restriction endonucleases, and fragment length sizes are determined by gel electrophoresis.

In yet another embodiment, any of a variety of sequencing reactions known in the art can be used to directly sequence the allele. Exemplary sequencing reactions include those based on techniques developed by Maxim and Gilbert ((1977) Proc. Natl. Acad Sci USA 74:560) or Sanger (Sanger et al (1977) Proc. Nat. Acad. Sci USA 74:5463). It is also contemplated that any of a variety of automated sequencing procedures may be utilized when performing the subject assays (see, for example Biotechniques (1995) 19:448), including sequencing by mass spectrometry (see, for example PCT publication WO 94/16101; Cohen et al. (1996) Adv Chromatogr 36:127-162; and Griffin et al. (1993) Appl Biochem Biotechnol 38:147-159). It will be evident to one of skill in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers, et al. (1985) Science 230:1242). In general, the art technique of "mismatch cleavage" starts by providing heteroduplexes formed by hybridizing (labeled) RNA or DNA containing the wild-type allele with the sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) Proc. Natl. Acad Sci USA 85:4397; and Saleeba et al (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on an allele of an IL-1 locus haplotype is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify an IL-1 locus allele. For example, single strand conformation polymorphism (SSCP) may be used to detect differences in electrophoretic mobility between mutant and wild type nucleic acids (Orita et al. (1989) Proc Natl. Acad. Sci USA 86:2766, see also Cotton (1993) Mutat Res 285:125-144; and Hayashi (1992) Genet Anal Tech Appl 9:73-79). Single-stranded DNA fragments of sample and control IL-1 locus alleles are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of alleles in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265: 12753).

Examples of other techniques for detecting alleles include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) Nature 324:163); Saiki et al (1989) Proc. Natl. Acad. Sci USA 86:6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al (1989) Nucleic Acids Res. 17:2437-2448) or at the extreme 3' end of one primer where, under appropriate conditions, mismatch can prevent, or reduce polymerase extension (Prossner (1993) Tibtech 11:238. In addition it may be desirable to introduce a novel restriction site in the region of the mutation to create cleavage-based detection (Gasparini et al (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren, U. et al. ((1988) Science 241:1077-1080). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. USA 87:8923-27). In this method, PCR is used to achieve the exponential amplification of target DNA, which is then detected using OLA.

Several techniques based on this OLA method have been developed and can be used to detect alleles of an IL-1 locus haplotype. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) Nucleic Acids Res 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

Another embodiment of the invention is directed to kits for detecting a predisposition for developing a cardiovascular disorder, either due to the occlusion of an artery or due to the formation of fragile plaque, or due to the formation of restenosis. This kit may contain one or more oligonucleotides, including 5' and 3' oligonucleotides that hybridize 5' and 3' to at least one allele of an IL-1 locus haplotype. PCR amplification oligonucleotides should hybridize between 25 and 2500 base pairs apart, preferably between about 100 and about 500 bases apart, in order to produce a PCR product of convenient size for subsequent analysis.

Particularly preferred primers for use in the diagnostic method of the invention include SEQ ID Nos. 1-10.

The design of additional oligonucleotides for use in the amplification and detection of IL-1 polymorphic alleles by the method of the invention is facilitated by the availability of both updated sequence information from human chromosome 2q13—which contains the human IL-1 locus, and updated human polymorphism information available for this locus. Suitable primers for the detection of a human polymorphism in these genes can be readily designed using this sequence information and standard techniques known in the art for the design and optimization of primers sequences. Optimal design of such primer sequences can be achieved, for example, by the use of commercially available primer selection programs such as Primer 2.1, Primer 3 or GeneFisher (See also, Nicklin M. H. J., Weith A. Duff G. W., "A Physical Map of the Region Encompassing the Human Interleukin-1.alpha., interleukin-1.beta., and Interleukin-1 Receptor Antagonist Genes" Genomics 19: 382 (1995); Nothwang H. G., et al. "Molecular Cloning of the Interleukin-1 gene Cluster: Construction of an Integrated YAC/PAC Contig and a partial transcriptional Map in the Region of Chromosome 2q13" Genomics 41: 370 (1997); Clark, et al. (1986) Nucl. Acids. Res., 14:7897-7914 [published erratum appears in Nucleic Acids Res., 15:868 (1987) and the Genome Database (GDB) project.

For use in a kit, oligonucleotides may be any of a variety of natural and/or synthetic compositions such as synthetic oligonucleotides, restriction fragments, cDNAs, synthetic peptide nucleic acids (PNAs), and the like. The assay kit and method may also employ labeled oligonucleotides to allow ease of identification in the assays. Examples of labels which may be employed include radio-labels, enzymes, fluorescent compounds, streptavidin, avidin, biotin, magnetic moieties, metal binding moieties, antigen or antibody moieties, and the like.

The kit may, optionally, also include DNA sampling means. DNA sampling means are well known to one of skill in the art and can include, but not be limited to substrates, such as filter papers, the AmpliCard™ (University of Sheffield, Sheffield, England S 10 2JF; Tarlow, J W, et al., *J. of Invest. Dermatol.* 103:387-389 (1994)) and the like; DNA purification reagents such as Nucleon™ kits, lysis buffers, proteinase solutions and the like; PCR reagents, such as 10× reaction buffers, thermostable polymerase, dNTPs, and the like; and allele detection means such as the HinfI restriction enzyme, allele specific oligonucleotides, degenerate oligonucleotide primers for nested PCR from dried blood.

4.3.3. Pharmacogenomics

Knowledge of the particular alleles associated with a susceptibility to developing a cardiovascular disorder, alone or in conjunction with information on other genetic defects contributing to a cardiovascular disorder allows a customization of the prevention or treatment in accordance with the individual's genetic profile, the goal of "pharmacogenomics".

One approach to the prevention and treatment of a cardiovascular disease relates to the identification of risk factors for the particular disease.

For example, subjects having an allele 2 of any of the following markers: IL-1A +4845 or IL-1B (+3954), or allele 1 of the following markers: IL-1B (−511) or IL-1RN (+2018) or any nucleic acid sequence in linkage disequilibrium with any of these alleles may have or be predisposed to developing a cardiovascular disorder characterized by the formation of fragile plaque, may be predisposed to an increased risk of myocardial infarction, stroke, acute peripheral vascular blockage, and aneurysm formation in the mid-size to large arteries. These patients are also predisposed to developing severe adult periodontitis.

Another approach to the treatment of cardiovascular diseases relates to interfering with the progression of the underlying disorder, ameliorating the symptoms and signs of the disease, or protecting a target tissue so that the presence of a cardiovascular disorder affecting the circulation of the tissue does not result in the development of clinical symptoms and signs related to that target tissue.

As an example, certain drugs have a stabilizing effect on atherosclerotic plaques or other beneficial effects on the sequelae of fragile plaque disease. As examples, β-adrenergic receptor blockers reduce recurrence of myocardial infarction, angiotensin-converting enzyme inhibitors reduce the incidence of myocardial infarction, certain antibiotics and antioxidants also have been shown to be effective in stabilizing plaques. Drugs that have the capability of lowering lipids, such as 3-hydroxy-3methylglutaryl-coenzyme A reductase inhibitors (statins) are also important. Based on the disclosure of the pattern 1 IL-1 genotype disclosed herein, these patients may respond better to therapeutics which are aimed at plaque stabilization rather than revascularization or other invasive techniques.

At the cellular level, lowering of serum cholesterol leads to a decrease in inflammatory cells within the atherosclerotic plaques. At the molecular level, lipid lowering has been shown to decrease metalloproteinase activity in these plaques.

In one embodiment techniques such as gene therapy may be used to stabilize vulnerable plaque, for example, this could include over-expression of tissue inhibitors of matrix metalloproteinases and anti-sense methods to block proinflammatory molecules.

On the other hand, subjects having an allele 1 of any of the following markers: IL-1A +4845 or IL-1B (+3954), or allele 2 of the following markers: IL-1B (−511) or IL-1RN (+2018) may respond better to particular methods such as revascularization, or those methods that alter the progression of intimal-medial arterial thickening.

Yet another approach to the management of cardiovascular disorders and diseases comprises the management of conditions increasing risk for cardio-vascular disorders.

Factors associated with the progression of atherosclerosis include Diabetes Mellitus, high blood pressure, Hypercholesterolemia, High lipoprotein-a, Obesity, and Smoking. Of these, the factors amenable to pharmacological intervention include: i) diabetes, ii) hypertension, and iii) dyslipidemias. Examples of lipid lowering drugs include: Anion exchange resins such as cholestyramine, colestipol; HMG CoA reductase inhibitors or (statins) such as simvastatin, pracastatin, cerivastatin, fluvastatin, atorvastatin, lovastatin; Fibrates such as fenofibrate, bezafibrate, gemfibrozil, clofibrate, ciprofibrate; Nicotinic acid and analogues: acipimox, nicofuranose; Probucol which increases non-receptor mediated LDL clearance and decreases LDL oxidation; Fish oils such as maxepa, Omacor; and Cholesterol absorption inhibitors such as pamaqueside, tiqueside.

Accordingly, therapeutics that address the particular molecular basis of the disease in the subject may be developed based upon such genotype analysis. Thus, comparison of an individual's IL-1 profile to the population profile for a cardiovascular disorder, permits the selection or design of drugs or other therapeutic regimens that are expected to be safe and efficacious for a particular patient or patient population (i.e., a group of patients having the same genetic alteration).

In addition, the ability to target populations expected to show the highest clinical benefit, based on genetic profile can enable: 1) the repositioning of drugs already marketed for prevention or treatment of cardiovascular disorder; 2) the rescue of drug candidates whose clinical development has been discontinued as a result of safety or efficacy limitations, which are patient subgroup-specific; and 3) an accelerated and less costly development for candidate therapeutics and more optimal drug labeling (e.g. since measuring the effect of various doses of an agent on a vascular disorder causative mutation is useful for optimizing effective dose).

The treatment of an individual with a particular therapeutic can be monitored by determining protein (e.g. IL-1α, IL-1β, or IL-1Ra), mRNA and/or transcriptional level. Depending on the level detected, the therapeutic regimen can then be maintained or adjusted (increased or decreased in dose). In a preferred embodiment, the effectiveness of treating a subject with an agent comprises the steps of: (i) obtaining a preadministration sample from a subject prior to administration of the agent; (ii) detecting the level or amount of a protein, mRNA or genomic DNA in the preadministration sample; (iii) obtaining one or more post-administration samples from the subject; (iv) detecting the level of expression or activity of the protein, mRNA or genomic DNA in the post-administration sample; (v) comparing the level of expression or activity of the protein, mRNA or genomic DNA in the preadministration sample with the corresponding protein, mRNA or genomic DNA in the postadministration sample, respectively; and (vi) altering the administration of the agent to the subject accordingly.

Cells of a subject may also be obtained before and after administration of a therapeutic to detect the level of expression of genes other than an IL-1 gene to verify that the therapeutic does not increase or decrease the expression of genes which could be deleterious. This can be done, e.g., by using the method of transcriptional profiling. Thus, mRNA from cells exposed in vivo to a therapeutic and mRNA from the same type of cells that were not exposed to the therapeutic could be reverse transcribed and hybridized to a chip containing DNA from numerous genes, to thereby compare the expression of genes in cells treated and not treated with the therapeutic.

4.4 Therapeutics for Cardio Vascular Disorders and Diseases

Modulators of IL-1 (e.g. IL-1α, IL-1β or IL-1 receptor antagonist) or a protein encoded by a gene that is in linkage disequilibrium with an IL-1 gene can comprise any type of compound, including a protein, peptide, peptidomimetic, small molecule, or nucleic acid. Preferred agonists include nucleic acids (e.g. encoding an IL-1 protein or a gene that is up- or down-regulated by an IL-1 protein), proteins (e.g. IL-1 proteins or a protein that is up- or down-regulated thereby) or a small molecule (e.g. that regulates expression or binding of an IL-1 protein). Preferred antagonists, which can be identified, for example, using the assays described herein, include nucleic acids (e.g. single (antisense) or double stranded (triplex) DNA or PNA and ribozymes), protein (e.g. antibodies) and small molecules that act to suppress or inhibit IL-1 transcription and/or protein activity.

4.4.1. Effective Dose

Toxicity and therapeutic efficacy of such compounds can be determined by standard pharmaceutical procedures in cell cultures or experimental animals, e.g., for determining The $LD_{50}$ (the dose lethal to 50% of the population) and the $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissues in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.4.2. Formulation and Use

Compositions for use in accordance with the present invention may be formulated in a conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.5 Assays to Identify Therapeutics for Cardiovascular Disorders and Diseases Based on the identification of mutations that cause or contribute to the development of a vascular disorder, the invention further features cell-based or cell free assays, e.g., for identifying vascular disorder therapeutics. In one embodiment, a cell expressing an IL-1 receptor, or a receptor for a protein that is encoded by a gene which is in linkage disequilibrium with an IL-1 gene, on the outer surface of its cellular membrane is incubated in the presence of a test compound alone or in the presence of a test compound and another protein and the interaction between the test compound and the receptor or between the protein (preferably a tagged protein) and the receptor is detected, e.g., by using a microphysiometer (McConnell et al. (1992) Science 257:1906). An interaction between the receptor and either the test compound or the protein is detected by the microphysiometer as a change in the acidification of the medium. This assay system thus provides a means of identifying molecular antagonists which, for example, function by interfering with protein-receptor interactions, as well as molecular agonist which, for example, function by activating a receptor.

Cellular or cell-free assays can also be used to identify compounds which modulate expression of an IL-1 gene or a gene in linkage disequilibrium therewith, modulate translation of an mRNA, or which modulate the stability of an mRNA or protein. Accordingly, in one embodiment, a cell which is capable of producing an IL-1, or other protein is incubated with a test compound and the amount of protein produced in the cell medium is measured and compared to that produced from a cell which has not been contacted with the test compound. The specificity of the compound vis a vis the protein can be confirmed by various control analysis, e.g., measuring the expression of one or more control genes. In particular, this assay can be used to determine the efficacy of antisense, ribozyme and triplex compounds.

Cell-free assays can also be used to identify compounds which are capable of interacting with a protein, to thereby modify the activity of the protein. Such a compound can, e.g., modify the structure of a protein thereby effecting its ability to bind to a receptor. In a preferred embodiment, cell-free assays for identifying such compounds consist essentially in a reaction mixture containing a protein and a test compound or a library of test compounds in the presence or absence of a binding partner. A test compound can be, e.g., a derivative of a binding partner, e.g., a biologically inactive target peptide, or a small molecule.

Accordingly, one exemplary screening assay of the present invention includes the steps of contacting a protein or functional fragment thereof with a test compound or library of test compounds and detecting the formation of complexes. For detection purposes, the molecule can be labeled with a specific marker and the test compound or library of test compounds labeled with a different marker. Interaction of a test compound with a protein or fragment thereof can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the protein or functional fragment thereof is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) an IL-1 or other protein, (ii) an appropriate receptor, and (iii) a test compound; and (b) detecting interaction of the protein and receptor. A statistically significant change (potentiation or inhibition) in the interaction of the protein and receptor in the presence of the test compound, relative to the interaction in the absence of the test compound, indicates a potential antagonist (inhibitor). The compounds of this assay can be contacted simultaneously. Alternatively, a protein can first be contacted with a test compound for an appropriate amount of time, following which the receptor is added to the reaction mixture. The efficacy of the compound can be assessed by generating dose response curves from data obtained using various concentrations of the test compound. Moreover, a control assay can also be performed to provide a baseline for comparison.

Complex formation between a protein and receptor may be detected by a variety of techniques. Modulation of the formation of complexes can be quantitated using, for example, detectably labeled proteins such as radiolabeled, fluorescently labeled, or enzymatically labeled proteins or receptors, by immunoassay, or by chromatographic detection.

Typically, it will be desirable to immobilize either the protein or the receptor to facilitate separation of complexes from uncomplexed forms of one or both of the proteins, as well as to accommodate automation of the assay. Binding of protein and receptor can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the receptor, e.g. an $^{35}$S-labeled receptor, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of protein or receptor found in the bead fraction quantitated from the gel using standard electrophoretic techniques such as described in the appended examples. Other techniques for immobilizing proteins on matrices are also available for use in the subject assay. For instance, either protein or receptor can be immobilized utilizing conjugation of biotin and streptavidin. Transgenic animals can also be made to identify agonists and antagonists or to confirm the safety and efficacy of a candidate therapeutic. Transgenic animals of the invention can include non-human animals containing a cardiovascular disorder causative mutation under the control of an appropriate endogenous promoter or under the control of a heterologous promoter.

The transgenic animals can also be animals containing a transgene, such as reporter gene, under the control of an appropriate promoter or fragment thereof. These animals are useful, e.g., for identifying drugs that modulate production of an IL-1 protein, such as by modulating gene expression. Methods for obtaining transgenic non-human animals are well known in the art. In preferred embodiments, the expression of the cardiovascular disorder causative mutation is restricted to specific subsets of cells, tissues or developmental stages utilizing, for example, cis-acting sequences that control expression in the desired pattern. In the present invention, such mosaic expression of a protein can be essential for many forms of lineage analysis and can additionally provide a means to assess the effects of, for example, expression level which might grossly alter development in small patches of tissue within an otherwise normal embryo. Toward this end, tissue-specific regulatory sequences and conditional regulatory sequences can be used to control expression of the mutation in certain spatial patterns. Moreover, temporal patterns of expression can be provided by, for example, conditional recombination systems or prokaryotic transcriptional regulatory sequences. Genetic techniques, which allow for the expression of a mutation can be regulated via site-specific genetic manipulation in vivo, are known to those skilled in the art.

The transgenic animals of the present invention all include within a plurality of their cells a cardiovascular disorder causative mutation transgene of the present invention, which transgene alters the phenotype of the "host cell". In an illustrative embodiment, either the cre/loxP recombinase system of bacteriophage P1 (Lakso et al. (1992) *PNAS* 89:6232-6236; Orban et al. (1992) *PNAS* 89:6861-6865) or the FLP recombinase system of *Saccharomyces cerevisiae* (O'Gorman et al. (1991) *Science* 251:1351-1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509-1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation of expression of the causative mutation transgene can be regulated via control of recombinase expression.

Use of the cre/loxP recombinase system to regulate expression of a causative mutation transgene requires the construction of a transgenic animal containing transgenes encoding both the Cre recombinase and the subject protein. Animals containing both the Cre recombinase and the cardio-vascular disorder causative mutation transgene can be provided through the construction of "double" transgenic animals. A convenient method for providing such animals is to mate two transgenic animals each containing a transgene.

Similar conditional transgenes can be provided using prokaryotic promoter sequences which require prokaryotic proteins to be simultaneously expressed in order to facilitate expression of the transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the transactivating protein, e.g. a recombinase or a prokaryotic protein, is delivered to the tissue and caused to be expressed, such as in a cell-type specific manner. By this method, the transgene could remain silent into adulthood until "turned on" by the introduction of the transactivator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with H-$2^b$, H-$2^d$ or H-$2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for microinjection. In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA will be incorporated into the host gene before the first cleavage (Brinster et al. (1985) *PNAS* 82:4438-4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote. Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1-7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000-20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. Further, in such embodiments the sequence will be attached to a transcriptional control element, e.g., a promoter, which preferably allows the expression of the transgene product in a specific type of cell.

Retroviral infection can also be used to introduce the transgene into a non-human animal. The developing non-human embryo can be cultured in vitro to the blastocyst stage. During this time, the blastomeres can be targets for retroviral infection (Jaenich, R. (1976) *PNAS* 73:1260-1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927-6931; Van der Putten et al. (1985) *PNAS* 82:6148-6152). Transfection is easily and efficiently obtained by culturing the blastomeres on a monolayer of virus-producing cells (Van der Putten, supra; Stewart et al. (1987) *EMBO J.* 6:383-388). Alternatively, infection can be performed at a later stage. Virus or virus-producing cells can be injected into the blastocoele (Jahner et al. (1982) *Nature* 298:623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154-156; Bradley et al. (1984) *Nature* 309:255-258; Gossler et al. (1986) *PNAS* 83: 9065-9069; and Robertson et al. (1986) *Nature* 322:445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468-1474.

The present invention is further illustrated by the following examples which should not be construed as limiting in any way. The contents of all cited references (including literature references, issued patents, published patent applications as cited throughout this application) are hereby expressly incorporated by reference. The practice of the present invention will employ, unless otherwise indicated, conventional techniques that are within the skill of the art. Such techniques are explained fully in the literature. See, for example, Molecular Cloning A Laboratory Manual, (2nd ed., Sambrook, Fritsch and Maniatis, eds., Cold Spring Harbor Laboratory Press: 1989); DNA Cloning, Volumes I and II (D. N. Glover ed., 1985); Oligonucleotide Synthesis (M. J. Gait ed., 1984); U.S. Pat. No. 4,683,195; U.S. Pat. No. 4,683,202; and Nucleic Acid Hybridization (B. D. Hames & S. J. Higgins eds., 1984).

5. EXAMPLES

Example 1

Markers for Single Vessel Coronary Artery Disease

The objective of this study was to determine if patients with an early form of coronary artery atherosclerosis, i.e., single vessel coronary artery disease, were more likely to have specific alleles in the following genes: IL-1A (−889 marker), IL-1B (−511 and +3954 markers), IL-1RN (VNTR marker) or TNFα (−308 marker). Multiple vessel disease generally represents a later stage of the disease that may involve many factors which could complicate data interpretation. Therefore, patients who presented with a complaint of chest pain were evaluated by a cardiologist, and those with angiographic evidence of significant atherosclerosis in more than one coronary artery were excluded from analysis.

Patient Cohorts: Angiography from either the femoral or brachial artery was performed using conventional techniques. Of the patients examined, eighty-five (85) had no obvious luminal irregularities by angiography and were classified as controls having angiographically normal coronary arteries. A patient was classified as having single vessel disease if one of three epicardial coronary vessels containing an epicardial stenosis causing 50% reduction in luminal diameter, as assessed by eye. Fifty-eight (58) patients were found to have single vessel coronary artery disease. Patients with multiple vessel disease were excluded. Both control and single vessel disease groups had comparable mean ages, 57.6±10.4 years and 56.4±9.4 years; respectively. The male to female ratio in the control group was 1:1.7 and 2.6:1 in the diseased group.

General Methods: Reactions and manipulations involving nucleic acid techniques, unless stated otherwise, were performed as generally described in Sambrook, et al., *Molecular Cloning: A Laboratory Manual*, Cold Spring Harbor Laboratory Press (1989). Polymerase chain reaction (PCR) was carried out generally as described in *PCR Protocols: A Guide to Methods and Applications*, Academic Press, San Diego, Calif. (1990). Genotyping methodology was as generally described in U.S. Pat. Nos. 4,666,828; 4,683,202; 4,801,531; 5,192,659; and 5,272,057 and McDowell, et al., *Arthritis & Rheumatism*, 38(2):221-8 (1995).

DNA Preparation: DNA was extracted from whole blood using a modification of the salt-out method (Nucleon II™, Scotlab, UK).

Genotyping IL-1RN: Alleles associated with the IL-1RN gene were previously described by Tarlow, et al., *Human Genetics*, 91:403-4 (1993). Enzymes used in PCR were from Promega (UK) and thermocyclers were either MJ Research DNA Engine or Biometra. The following primers were produced in an ABI DNA synthesizer:

5'CTCAGCAACACTCCTAT 3' (SEQ ID No. 1)
5' TCCTGGTCTGCAGGTAA 3' (SEQ ID No. 2)

PCR amplification was performed with a final magnesium concentration of 1.75 mM and a cycling protocol of 1 cycle at 96° C. for 1 minute; 30 cycles of [94° C. for 1 minute, 60° C. for 1 minute, and 70° C. for 1 minute]; and 1 cycle at 70° C. for 2 minutes. Following PCR the different alleles were electrophoresed on 2% agarose gel stained with ethidium bromide and visualized and identified under uv light. Negative controls without DNA were performed in each experiment.

Intron 2 of the IL-1RN gene contains a variable number tandem repeat (VNTR) region that gives rise to five (5) alleles as follows:

Allele 1 contains four repeats and displays a 412 bp PCR product;
Allele 2 contains two repeats and displays a 240 bp PCR product;
Allele 3 contains three repeats and displays a 326 bp PCR product;
Allele 4 contains five repeats and displays a 498 bp PCR product; and
Allele 5 contains six repeats and displays a 584 bp PCR product.

Genotyping IL-1B (−511)

The −511 marker of IL-1B was described by diGiovine, *Hum. Molec. Genet.*, 1(6):450 (1992). The single base variation (C/T) marker at IL-1B base −511 was identified on the basis of an AvaI site on allele 1(C), and a Bsu36I site on allele 2(T). PCR was performed with 1 cycle at 95° C. for 2 minutes, 35 cycles at [95° C. for 1 minute, 53° C. for 1 minute, and 74° C. for 1 minute] and 1 cycle at 74° C. for 4 minutes. Analysis of the PCR products was by restriction enzyme digestion with AvaI and Bsu36I at 37° C. for 8 hours followed by size analysis with 8% PAGE. The following primers were produced in an ABI DNA synthesizer (Clark, et al., *Nucl. Acids. Res.*, 14:7897-7914 (1986) [published erratum appears in *Nucleic Acids Res.*, 15(2):868 (1987)]; GENBANK X04500):

```
5' TGGCATTGATCTGGTTCATC 3'  (-702/-682)    (SEQ ID No: 5)

5' GTTTAGGAATCTTCCCACTT 3'  (-417/-397)    (SEQ ID No: 6)
```

Results: There was no significant difference between the control and diseased patients in the frequency of different alleles in the genes for IL-1A (−889 marker), IL-1B (+3954 marker) or TNFα (−308 marker). However, allele 2 of the VNTR marker in the IL-1RN gene was significantly over-represented in the single vessel disease patients, 41% versus 22% in controls. It is estimated that individuals with at least one copy of allele 2 are 2.44 times as likely to have single vessel coronary artery disease than those who are negative for allele 2 (odds Ratio=2.44, p=0.003, 95% confidence interval=1.35-4.43).

In addition, individuals who had two copies, i.e., were homozygous for allele 2 in IL-1RN, were 5.36 times as likely to have single vessel coronary artery disease than those who were negative for allele 2 (odds Ratio=5.36, p=0.005, 95% confidence interval=1.6-17.97).

Carriage of one copy of allele 2 of the −511 marker of the IL-1B gene was increased in single vessel coronary disease to 52% compared with 38% in controls. It is estimated that individuals with at least one copy of allele 2 are 1.74 times as likely to have single vessel disease than those who are negative for allele 2 (Odds Ratio=1.74, p=0.1, 95% confidence interval=0.86-3.52).

These findings indicate that allele 2 of the IL-1RN gene is a marker for susceptibility to the development of coronary artery occlusive disease, manifested as single-vessel stenosis. This allele is associated with an increased risk of coronary artery disease of 2.4 to 5.4 times, depending on whether there in one copy (heterozygous) or two copies (homozygous) of the disease-associated allele. The influence of this allele on risk for coronary artery disease is shown in Table 1 relative to other common risk factors.

Additionally, an allele for the IL-1B gene was discovered to be associated with single vessel coronary artery disease. This allele is associated with an increased risk of coronary artery disease of 1.74 times.

TABLE 1

| Risk Factor | Increased Risk for Coronary Artery Disease |
|---|---|
| Smoking (1 pack/day) | 2.5 |
| Sedentary lifestyle | 1.9 |
| Severe obesity (women) | 3.3 |
| Hypertension | 2.1 |
| High cholesterol (>240) | 2.4 |
| IL-1RN (VNTR) allele 2 - heterozygous | 2.4 |
| IL-1RN (VNTR) allele 2 - homozygous | 5.4 |
| IL-1B (−511) allele 2 | 1.74-1.92 |

Example 2

Markers for Multiple Vessel Coronary Artery Disease

The objective of this study was to determine if patients with a later or more diffuse form of coronary artery atherosclerosis, i.e., multiple vessel coronary artery disease, were more likely to have specific alleles in the genes of the IL-1 gene cluster or TNFα.

Patient Cohorts: Patient cohorts were determined as in Example 1, except that a patient was classified as having multiple vessel disease if more than one epicardial coronary vessel contained an epicardial stenosis causing >50% reduction in luminal diameter, as assessed by eye. Of the patients examined, 86 were classified as controls having angiographically normal coronary arteries and 315 patients were found to have multiple vessel coronary artery disease. Both controls and single vessel disease groups had comparable mean ages, 57.6±10.4 years and 60.8±1.13 years respectively. The male to female ratio in the control group was 1:1:7 and 3.7:1 in the diseased group.

General Methods: Reactions and Methods were as in Example 1.

Results: There was no significant difference between the control and diseased patients in the frequency of different alleles in the genes for IL-1A (−889 marker), IL-1B (+3954 marker), and IL-1RN (VNTR marker). However, carriage of one copy of the Bsu36I allele (allele 2) of the −511 marker of the IL-1B gene was increased in the multiple vessel disease patients, 54% versus 38% in controls. It is estimated that individuals with at least one copy of allele 2 of the −511 marker are 1.92 times as likely to have multiple vessel coronary artery disease than those who are negative for allele 2 (Odds Ratio+1.92, p=0.009, 95% confidence interval=1.17-3.16). There appears to be no dose effect, in this population at least, for the −511 marker.

In summary, an allele for the IL-1B gene was discovered to be associated with multiple vessel coronary artery disease. This allele is associated with an increased risk of coronary artery disease of 1.92 times.

Single vessel and multiple vessel coronary artery disease each appear to be linked with different genes of the IL-1 gene cluster. This may arise as a true biological distinction, where IL-1 RA modulates IL-1β effects in such a way as to produce the single vessel phenotype. Alternatively, it may be that both genes are, in fact, associated with coronary artery disease as a whole and that the associations observed here result from the way this particular population exhibited coronary artery disease. With either interpretation, a strong association between IL-1 biology and coronary artery disease has been established.

Example 3

Association of Interleukin-1 Gene Variants and Carotid Arterial Wall Thickness

The association between carotid intimal medial wall thickness (IMT) and four basic biallelic markers (IL-1A (+4845), IL-1B (+3954), IL-1RN (+2018)) in the interleukin-1 (IL-1) gene cluster on chromosome 2 was investigated among participants in the Atherosclerosis Risk in Communities (ARIC) Study, a cohort of 15,792 men and women 45-64 years of age selected from four U.S. communities. Far wall thickness was measured by B-mode ultrasound and analyzed using a cut-point for elevated average IMT ($\geq 1$ mm) chosen a priori to identify individuals at greatest risk of cardiovascular disease. After excluding those with a history of cardiovascular disease, a stratified random sample of 252 African Americans and 924 Caucasians was genotyped. Among African Americans, carriers of the less common allele (allele 2) of IL-1RN (+2018) were more likely than non-carriers to have average IMT $\geq 1$ mm (16% vs 5% p=0.04) in a basic model adjusting for age, gender and study center. Among Caucasians, the adjusted proportion of individuals with elevated IMT was also higher in those carrying IL-1RN (+2018) allele 2 (9% vs.

6%), but this difference was not statistically significant (p=0.10). There were no associations between the IL-1A (+4845), IL-1B (+3954) or IL-1B (−511) variants and carotid IMT in either ethnic group.

Example 4

IL-1 Genotypes Associated with Plaque Formation and Increased Plaque Fragility

Polymorphisms in the gene for IL-1 receptor antagonist and the linked IL-1B (−511) gene are strongly associated with the presence of large (>50% occlusion of the vessel) plaques in the coronary arteries and early atherosclerotic changes in the carotid artery wall (ARIC data). These data suggest that the genetic polymorphism pattern that involves IL-1RN (+2018) allele 2 and/or IL-1B (−511) allele 2 is predictive of large, occluding plaques.

Certain IL-1 genotypes are associated with increased risk for clinical events such as thrombosis and embolism. We propose that allele 2 in either or both of the loci IL-1A (+4845) and IL-1B (+3954) would be expected to increase the inflammatory response and therefore increase plaque fragility and risk for clinical events such as thrombosis and embolism. This risk may be greatest in individuals with low levels of cholesterol, since higher levels would be expected to activate the maximal inflammatory response even in IL-1 wild-types (e.g. IL-1A (+4845)=1.1 and IL-1B (+3954)=1.1).

We propose that the genotypes associated with larger occlusive plaques, i.e. IL-1RN (+2018) allele 2 or IL-1B (−511) allele 2, would be predictive of lower risk for plaque fragility.

Out of approximately 15,000 healthy individuals followed longitudinally for clinical events (ARIC), 370 thrombotic or embolic events were documented. A group of approximately 900 randomized stratified controls were selected for comparison.

Allele 2 at IL-1A (+4845) and IL-1B (+3954) Influence Fragile Plaque-Related Clinical Events:

For cases with LDL <130 (n=535)
IL-1A (+4845) genotype 2.2: Odds ratio (OR+95% CI) for clinical event=3.03 (0.96-9.1); p=0.059
For cases with Total Cholesterol <200 (n=425)
IL-1A (+4845) genotype 2.2: OR=6.25 (1.69-20.00); p=0.006
IL-1B (+3954) genotype 1.2 or 2.2: OR=2.58 (1.25-5.31); p=0.010

Allele 2 at IL-1RN (+2018) is Inversely Related to Fragile Plaque-Related Clinical Events, Thereby Suggesting a Stabilization of Atherosclerotic Plaque:

For all cases (n=1214)
IL-1RN (+2018) genotype 1.2 or 2.2: OR=0.65 (0.43-0.96); p=0.031
For LDL >160 (n=343)
IL-1RN (+2018) genotype 1.2 or 2.2: OR=0.33 (0.14-0.73); p=0.058
For Total Cholesterol >240 (n=307)
IL-1RN (+2018) genotype 1.2 or 2.2: OR=0.28 (0.11-0.68); p=0.054

Example 5

The IL-1 Composite Genotype that is Consistent with Haplotype Pattern 1 is Associated with Periodontitis and the IL-1 Genotype that is Consistent with Haplotype Pattern 2 is Associated with Occlusive Cardiovascular Disease The association between periodontitis, cardiovascular disease and four basic biallelic markers (IL-1A (+4845), IL-1B (+3954), IL-1B (−511), and IL-1RN (+2018)) in the interleukin-1 (IL-1) gene cluster on chromosome 2 was investigated.

Two haplotype patterns may be defined by four polymorphic loci in the IL-1 gene cluster as shown in Table 2 (IL-1A (+4845), IL-1B (+3954), IL-1B (−511), IL-1RN (+2018)). One pattern includes allele 2 at both the IL-1A (+4845) and at the IL-1B (+3954) loci. The other pattern includes allele 2 at both the IL-1B (−511), and at the IL-1RN (+2018) loci.

TABLE 2

| Haplotypes | IL-1A (+4845) | IL-1B (+3954) | IL-1B (−511) | IL-1RN (+2018) |
|---|---|---|---|---|
| Pattern 1 | Allele 2 | Allele 2 | Allele 1 | Allele 1 |
| Pattern 2 | Allele 1 | Allele 1 | Allele 2 | Allele 2 |

The haplotype pattern indicates that when allele 2 is found at one locus, it is highly likely that it will be found at other loci. Previous data (Cox et al. (1998) Am. J. Hum. Genet. 62:1180-1188) indicate that when allele 2 is found at the IL-1A (+4845) locus allele 2 will also be present at the IL-1B (+3954) locus approximately 80% of the time. Haplotype patterns are relevant only for a single copy of a chromosome. Since there are two copies of chromosome 2 and standard genotyping procedures are unable to identify on which chromosome copy a specific allele is found, special statistical programs are used to infer haplotype patterns from the genotype pattern that is determined.

The distribution of these genetic patterns was evaluated in a new population that was part of a study of atherosclerosis (Pankow et al. (1999) The ARIC study. European Atherosclerosis Society Annual Meeting, Abstract, #646). In this population (N=1,368), IL-1A (+4845) genotype 2.2 was found in 10.2% of the subjects. However, in the subjects with genotype IL-1B (+3954)=2.2 (N=95), the IL-1A (+4845) genotype 2.2 was found in 71.6% of the subjects. This indicates that allele 2 at IL-1A (+4845) is inherited together with allele 2 at IL-1B (3954) at a much higher rate than one would expect given the distribution of each of these markers in the population. Similar data exists for allele 2 at the 2 loci that are characteristic of Pattern 2. In addition, when genotype Pattern 1 is found it is highly unlikely that allele 2 will be present at either of the loci that are characteristic of the other pattern.

The two genotype patterns are also associated with specific differences in the functional biology of interleukin-1. For example, peripheral monocytes from individuals with one or two copies of allele 2 at IL-1B (+3954) produced 2 to 4 times as much IL-1β when stimulated with LPS as monocytes from individuals who have the genotype pattern IL-1B (+3954) =1.1 (DiGiovini, F S et al. (1995) Cytokine, 7:606). Similar data have recently been reported for peripheral blood polymorphonuclear leukocytes isolated from individuals with severe periodontitis (Gore, E A et al. (1998) J. Clin. Periodontol., 25:781). In addition gingival crevice fluid (GCF) from subjects with the composite genotypes indicative of Pattern 1 have 2 to 3 times higher levels of IL-1β than GCF from individuals who are negative for those genotypes (Engelbretson, S P et al. (1999) J. Periodontol., in press). There are also data indicating that for Pattern 2, allele 2 at IL-1RN +2018 is associated with decreased levels of IL-1 receptor antagonist protein. Thus, Pattern 1 genotypes appear to be associated with increased IL-1 agonists, and Pattern 2 appears to be associated with decreased levels of IL-1 receptor antagonist.

The composite IL-1 genotypes that are consistent with Pattern 1 are associated with increased susceptibility to severe adult periodontitis (Kornman, K S et al. (1997), supra;

Gore, E A et al. (1998), supra; McGuire, M K et al. (1999) J. Periodontol., in press; McDevitt, M J et al. (1999) J. Periodontol., in press). One aspect of the IL-1 genotype influence on periodontitis appears to be an enhancement of the subgingival levels of specific bacterial complexes that include accepted periodontal pathogens (Socransky, S S et al. (1999) IADR Annual Meeting, Abstract#3600). Pattern 1 genotypes were not, however, associated with increased risk for occlusive cardiovascular disease. In data from the Atherosclerosis Risk in Communities (ARIC) study that was presented by Pankow and co-workers (see Pankow et al., supra), individuals with ultrasound measurements of carotid wall intima-medial thickness (IMT) that were indicative of occlusive cardiovascular disorders were compared to a stratified random control population for IL-1 gene polymorphisms. Neither IL-1A (+4845) or IL-1B (+3954) showed any association with risk for high IMT.

Genotypes that are characteristic of pattern 2 have recently been associated with increased susceptibility to occlusive coronary artery disease, but not increased risk for periodontitis. In a report on coronary artery disease, patients with angiographic evidence of coronary stenoses were significantly more likely to be carriers of allele 2 at either the IL-1RN (+2018) locus or the IL-1B (−511) locus (see Francis et al., supra). Both loci are characteristic of the haplotype Pattern 2. In the ARIC study, as discussed above, carriage of IL-1RN (+2018) allele 2 in African-Americans with high IMT measurements was significantly higher than ethnically matched controls. In Caucasians with high IMT measurements the carriage of one copy of allele 2 at IL-1RN (+2018) was significantly greater than in controls, however individuals homozygous at this locus were not different from controls. It should be noted that the prevalence of individuals homozygous for allele 2 at IL-1RN (+2018) in Caucasians in the study was substantially lower than that observed in other populations.

When individuals with periodontitis and gingival health were evaluated for genotype patterns consistent with Pattern 1 and Pattern 2, individuals with severe adult periodontitis were found to have a predominance of genotypes consistent with Pattern 1, whereas individuals with a healthy periodontal condition had genotype patterns that were dominated by neither Pattern 1 nor Pattern 2. It appears therefore that IL-1 genotypes consistent with the haplotype Pattern 1 are associated with severe periodontitis and plaque fragility disorders and not occlusive cardiovascular diseases whereas IL-1 genotypes consistent with the haplotype Pattern 2 are associated with occlusive cardiovascular diseases but not periodontitis or plaque fragility. One mechanism may be that IL-1 genotype Pattern 1 directly influences plaque fragility; another mechanism may be that Pattern 1 influences periodontitis directly, which may lead to indirect influences on cardiovascular disease through the periodontal microorganisms found as part of the oral chronic inflammatory process. Another mechanism may be that IL-1 genotype Pattern 2 directly influences cardiovascular occlusive disorders but has no influence on periodontitis. It is thus likely that IL-1 genetic polymorphisms can influence both cardiovascular disease and severe periodontitis, by a common underlying mechanism that directly alters the immunoinflammatory responses in both diseases in an identical fashion and by an indirect mechanism that enhances the oral bacterial load and then influences cardiovascular disease. The IL-1 genotypes that are consistent with haplotype Pattern 1 may influence the association between periodontidis and cardiovascular disease in one segment of the population by amplifying both the immuno-inflammatory response and the subgingival bacterial load.

Example 5

The Mayo Clinic Study

Study design. Patients 18 to 75 years of age undergoing clinically-indicated coronary angiography at Mayo Clinic, Rochester, Minn. were considered for this study. Patients were ineligible for inclusion if they had diabetes mellitus requiring therapy, a smoking history >50 pack years, prior or planned organ transplantation, pregnancy, prior percutaneous or surgical coronary revascularization, active bleeding or hemoglobin less than 8 g/dL, receipt of a blood transfusion within 30 days, hemodynamic instability, infection with human immunodeficiency virus, renal failure requiring dialysis, and a history of radiation therapy to the chest. The 504 patients represent >90% of patients eligible for this study who underwent coronary angiography during this period.

Angiographic analysis. Coronary angiograms were analyzed with hand-held calipers or visual analysis and divided into those revealing normal coronaries (smooth arteries with either no stenosis or with stenosis $\leq$10%), mild disease (coronary arteries with a reduction in luminal diameter between 10% and 50%), single vessel disease ($\geq$50% in a single coronary artery or its major branches), two vessel coronary artery disease ($\geq$50% lumenal diameter stenosis in two coronary arteries) and three vessel disease ($\geq$50% lumenal diameter stenosis in three coronary arteries). Angiograms were analyzed blinded to patients' risk factors and genetic analyses.

Laboratory analyses. Apolipoprotein $A_1$, apolipoprotein B, Lp (a) and fibrinogen assays were performed on the COBAS MIRA system. Normal ranges for these assays are apolipoprotein A1, 115-190 mg/dL; apolipoprotein B, 70-160 mg/dL; and Lp (a), 2.5-7.0 mg/dL; a normal range of fibrinogen is not reported. Total plasma homocysteine was measured.

Definitions. A family history of coronary disease was considered to be present if a first degree relative of the patient that did not smoke or have diabetes mellitus developed coronary disease when $\leq$55 years of age. Hyperlipidemia was defined as a total cholesterol $\geq$250 mg/dL or an LDL $\geq$150 mg/dL, or ongoing treatment with lipid-lowering agents in patients in whom pre-treatment lipid values were unknown. Angina and heart failure were classified according to the Canadian Heart Association and New York State classification schemes, respectively.

Statistical methods. Values are expressed as percentages and as means±one standard deviation. For odds ratios, 95% confidence intervals are presented in parentheses.

In preliminary analyses to determine correlates of coronary disease, chi-square tests and one-way ANOVAs were first performed to test the association of various traditional and emerging risk factors, as well as allelic variants among the IL-1 cluster genes, among patients with no disease, mild disease, one-vessel disease, two-vessel disease, and three-vessel disease. Coronary artery disease was then reclassified to compare patients with no disease or mild disease to patients with one-, two-, or three-vessel stenosis. Patients with some blockage but with coronary stenosis <50% were considered to have mild coronary disease and were grouped with those patients with no blockage (no disease), while patients with stenosis $\geq$50% in one, two, or three coronary arteries were grouped together for further analysis since these patients were considered to have a significant degree of coronary artery stenosis. The exact test for trends was used to test for trends in the proportion of patients with the polymorphisms.

Logistic regression models were fitted for the various risk factors according to quartiles and tertiles with the odds ratios reported for increasing quartile and tertile levels given. To analyze further the association of allelic variants of the IL-1 cluster genes with coronary artery disease, multiple logistic regression models were fitted with statistically significant confounders included in each model. All traditional and emerging risk factors were considered for inclusion in the model, and the model was fitted in a stepwise fashion to obtain the best fitting model where all factors included in the model were statistically significant. In addition, potential effect modifiers were considered for inclusion in the model. The response for the multiple logistic regression models was the presence or absence of significant coronary artery stenosis defined above.

In addition to analyzing all subjects included in the study, further statistical analyses were performed on subjects ≦£60 years of age and subjects >60 years of age separately. The analysis by age was considered to be appropriate since age has been shown to be a strong risk factor for coronary artery disease, and because genetic influences in multifactorial diseases are believed to be most evident in early onset cases. In addition, since epistasis may determine that genetic influences have different outcomes on males and females, subset analyses by gender was also considered to be important and males and females treated separately in some of the analyses.

Example 6

The Munich Study

Methods

Patients

The study included 1850 consecutive Caucasian patients with symptomatic coronary artery disease who underwent coronary stent implantation at Deutsches Herzzentrum München and 1. Medizinische Klinik rechts der Isar der Technischen Universität München. All patients were scheduled for angiographic follow-up at 6 months. All patients participating in this study gave written informed consent for the intervention, follow-up angiography, and genotype determination. The study protocol conformed to the Declaration of Helsinki and was approved by the institutional ethics committee.

TABLE 1

Baseline clinical characteristics.

| | IL-1RN 1/2 or 2/2 (n = 896) | IL-1RN 1/1 (n = 954) | P |
|---|---|---|---|
| Age - yr | 63.4 ± 10.0 | 62.6 ± 10.0 | 0.11 |
| Women - % | 22.4 | 19.9 | 0.19 |
| Arterial hypertension - % | 67.2 | 68.9 | 0.44 |
| Diabetes - % | 22.7 | 19.4 | 0.08 |
| Current or former smoker - % | 38.7 | 41.2 | 0.28 |
| Elevated total cholesterol - % | 42.5 | 43.1 | 0.81 |
| Acute myocardial infarction - % | 20.3 | 20.2 | 0.97 |
| Unstable angina - % | 27.9 | 27.8 | 0.95 |
| Prior bypass surgery - % | 10.6 | 11.5 | 0.53 |
| Reduced left ventricular function - % | 31.3 | 27.7 | 0.09 |
| Number of diseased coronary vessels | | | 0.39 |
| 1 vessel - % | 29.2 | 27.3 | |
| 2 vessels - % | 32.9 | 31.9 | |
| 3 vessels - % | 37.8 | 40.9 | |
| Periprocedural abciximab therapy - % | 19.8 | 19.6 | 0.93 |

Data are proportions or meanSD

The protocol of stent placement and poststenting therapy is familiar to practitioners in the arts. Most of the stents were implanted hand-mounted on conventional angioplasty balloons. Postprocedural therapy consisted of aspirin (100 mg twice daily, indefinitely) and ticlopidine (250 mg twice daily for 4 weeks). Patients with suboptimal results due to residual thrombus or dissection with flow impairment after stent implantation received additional therapy with abciximab given as bolus injection during stent insertion procedure and as a 12-hours continuous infusion thereafter. The decision to give abciximab was taken at the operator's discretion.

Determination of the IL-1RN Genotype

Genomic DNA was extracted from 200 ml of peripheral blood leukocytes with the QIAamp Blood Kit (Qiagen, Hilden, Germany) and the High Pure PCR Template Preparation Kit (Boehringer Mannheim, Mannheim, Germany).

IL-1RN genotyping was performed with the ABI Prism Sequence Detection System (PE Applied Biosystems, Weiterstadt, Germany). The use of allele-specific fluorogenic probes in the 5' nuclease reaction combines DNA amplification and genotype determination into a single assay 33. IL-1RN (+2018), a single base pair polymorphism in exon 2, was the polymorphism typed for this study 26. The nucleotide sequences of primers and probes were as follows: forward primer 5' GGG ATG TTA ACC AGA AGA CCT TCT ATC T 3' (SEQ ID NO. 11), reverse primer 5' CAA CCA CTC ACC TTC TAA ATT GAC ATT 3' (SEQ ID NO. 12), allele 1 probe 5' AAC AAC CAA CTA GTT GCT GGA TAC TTG CAA 3' (SEQ ID NO. 13), allele 2 probe 5' ACA ACC AAC TAG TTG CCG GAT ACT TGC 3' (SEQ ID NO. 18). The probes for allele 1 were labeled with the fluorescent dye 6-carboxy-fluorescein (FAM) and for allele 2 with the fluorescent dye tetrachloro-6-carboxy-fluorescein (TET) at the 5' end. Both probes were labeled with the quencher 6-carboxy-tetramethyl-rhodamine (TAMRA) at their 3' ends. The thermocycling protocol consisted of 40 cycles of denaturation at 95 C. for 15 seconds and annealing/extension at 64 C. for 1 minute. Genotype validation was performed by repeating the determination in 20% of the patients using a duplicate DNA sample with a novel subject code unrelated to the original subject code. There was a 100% matching between the 2 results.

Angiographic Assessment

Coronary lesions were classified according to the modified American College of Cardiology/American Heart Association grading system. Left ventricular function was assessed qualitatively on the basis of biplane angiograms using a 7 segment division; the diagnosis of reduced left ventricular function was established in the presence of at least two hypokinetic segments in the contrast angiogram. Quantitative computer-assisted angiographic analysis was performed off-line on angiograms obtained just before stenting, immediately after stenting, and at follow up using the automated edge-detection system CMS (Medis Medical Imaging Systems, Nuenen, The Netherlands). Operators were unaware of the patient's IL-1RN genotype. Identical projections of the target lesion were used for all assessed angiograms. Minimal lumen diameter, interpolated reference diameter, diameter stenosis, lesion length and diameter of the maximally inflated balloon were the angiographic parameters obtained with this analysis system. Acute lumen gain was calculated as the difference between minimal lumen diameter at the end of intervention and minimal lumen diameter before the intervention. Late lumen loss was calculated as the difference between minimal lumen diameter at the end of intervention and minimal lumen diameter at the time of follow-up angiography. Loss index was calculated as the ratio between late lumen loss and acute lumen gain.

Definitions and Study Endpoints

Primary endpoint of the study was restenosis. Two measures of restenosis were assessed: the incidence of angiographic restenosis defined as a diameter stenosis of 50% at 6-month follow-up angiography, and the need for target vessel revascularization (PTCA or aortocoronary bypass surgery [CABG]) due to symptoms or signs of ischemia in the presence of angiographic restenosis at the stented site over 1 year after the intervention. Other major adverse events evaluated were: death from any cause and myocardial infarction. All deaths were considered due to cardiac causes unless an autopsy established a noncardiac cause. The diagnosis of acute myocardial infarction was based on the criteria applied in the EPISTENT trial (new pathological Q waves or a value of creatine kinase [CK] or its MB isoenzyme at least 3 times the upper limit) 35. CK was determined systematically over the 48 hours following stenting procedure. Clinical events were monitored throughout the 1-year follow-up period. The assessment was made on the basis of the information provided by hospital readmission records, referring physician or phone interview with the patient. For all those patients who revealed cardiac symptoms during the interview, at least one clinical and electrocardiographic check-up was performed at the outpatient clinic or by the referring physician.

Statistical Analysis

Discrete variables are expressed as counts or percentages and compared with Chi-square or Fisher's exact test, as appropriate. Continuous variables are expressed as mean SD and compared by means of the unpaired, two-sided t-test or analysis of variance for more than 2 groups. Risk analysis was performed calculating the odds ratio and the 95% confidence interval. The main analysis consisted in comparing combined heterozygous and homozygous carriers of the IL-11RN*2 allele with homozygous carriers of the IL-11RN*1 allele. Moreover, the association between IL-1RN genotype and restenosis was assessed in a multivariate logistic regression model including also those clinical and lesion-related characteristics for which the comparison between carriers and noncarriers of the IL-1RN*2 allele showed a P-value 0.30. In this multivariate model, we tested for the possible interaction between IL-1RN genotype and age. Since the relative contribution of genetic factors to multifactorial processes such as restenosis may decrease with the age, we carried out an additional analysis for a prespecified subgroup of patients <60 years. Successively, we used test for trend for assessing gene dose effect, i.e. a stepwise increasing phenotypic response with the presence of 0, 1 or 2 putative alleles. Statistical significance was accepted for P-values 0.05.

Results

Patients Characteristics

The observed IL-1RN genotypes in the study population were 1/1 in 954 (51.6%), 1/2 in 742 (40.1%) and 2/2 in 154 (8.3%). Thus, allele 2 frequency was 0.28. The observed distribution complied with Hardy-Weinberg equilibrium. Main baseline characteristics of the patients are listed in Table 1 and compared between carriers and noncarriers of the IL-1RN*2 allele. There was a trend to a higher frequency of diabetes and reduced left ventricular function among carriers of the IL-1RN*2 allele. The other characteristics were evenly distributed between the 2 groups. The angiographic and procedural characteristics at the time of intervention are listed in Table 2 and show no significant differences between carriers and noncarriers of the IL-1RN*2 allele.

TABLE 2

Lesion and procedural characteristics at the time of intervention.

| | IL-1RN 1/2 or 2/2 (n = 896) | IL-1RN 1/1 (n = 954) | P |
|---|---|---|---|
| Target coronary vessels | | 0.89 | |
| Left main - % | 1.3 | 1.6 | |
| LAD - % | 40.1 | 39.3 | |
| LCx - % | 19.9 | 20.0 | |
| RCA - % | 32.6 | 31.9 | |
| Venous bypass graft - % | 6.1 | 7.2 | |
| Complex lesions - % | 75.2 | 74.1 | 0.58 |
| Restenotic lesions - % | 25.3 | 23.3 | 0.30 |
| Before stenting | | | |
| Reference diameter, mm | 3.02 ± 0.53 | 3.05 ± 0.54 | 0.29 |
| Diameter stenosis - % | 79.1 ± 14.9 | 78.7 ± 15.7 | 0.57 |
| Lesion length - mm | 12.1 ± 6.9 | 12.1 ± 6.6 | 0.98 |
| Procedural data | | | |
| Measured balloon diameter - mm | 3.2 ± 0.5 | 3.2 ± 5 | 0.45 |
| Maximal balloon pressure - atm | 13.9 ± 3.3 | 13.8 ± 3.2 | 0.20 |
| Stented segment length - mm | 20.0 ± 14.3 | 20.3 ± 13.6 | 0.70 |
| Immediately after stenting | | | |
| Diameter stenosis - % | 5.2 ± 9.1 | 5.4 ± 7.6 | 0.47 |

Data are proportions or meanSD
LAD indicates left anterior descending coronary artery;
LCx, left circumflex coronary artery;
RCA, right coronary artery;
complex lesions were defined as ACC/AHA lesion types B2 and C, according to the American College of Cardiology/American Heart Association grading system.

IL-1ra Polymorphism, Mortality and Myocardial Infarction after Stenting

Table 3 shows the adverse clinical events observed within the first 30 days after coronary stenting in carriers and non-carriers of the IL-1RN*2 allele. There was no association between the presence of the IL-1RN*2 allele and death, myocardial infarction or target vessel revascularization, showing no significant influence of the polymorphism in the IL-1ra gene in the risk for early thrombotic events after coronary stenting.

TABLE 3

Incidence of adverse events recorded during the early 30 days

| | IL-1RN 1/2 or 2/2 (n = 896) | IL-1RN 1/1 (n = 954) | P |
|---|---|---|---|
| Death - % | 0.9 | 0.9 | 0.91 |
| Nonfatal myocardial infarction - % | 3.3 | 2.6 | 0.52 |
| Q-wave - % | 1.1 | 0.7 | 0.39 |
| non-Q-wave - % | 2.2 | 1.9 | 0.60 |
| Target vessel revascularization - % | 3.0 | 2.3 | 0.34 |

One-year follow-up indicated also that there is no correlation between the presence of the IL-1RN*2 allele and mortality or incidence of myocardial infarction after the intervention. During the 1-year period, mortality rate was 2.8% in the combined group of IL-1RN 1/2 and IL-1RN 2/2 patients and 2.2% in IL-1 1/1 patients (P=0.42), yielding an odds ratio of 1.28 (95% confidence interval, 0.71-2.29). The incidence of nonfatal myocardial infarction was 3.5% in IL-1RN*2 allele carriers and 3.9% in homozygous carriers of the IL-1RN*1 allele (P=0.54), and the respective odds ratio was 0.86 (0.53-1.4).

IL-1ra Polymorphism and Restenosis after Stenting

Control angiography was performed in 84% of the patients after a median of 188 days (interquartile range, 171-205 days). The proportion of patients with control angiography was similar in the 2 groups defined by the presence or absence of the IL-1RN*2 allele. Table 4 lists the results of the quantitative assessment of 6-month angiograms.

TABLE 4

Results at follow-up angiography.

| | IL-1RN 1/2 or 2/2 (n = 758) | IL-1RN 1/1 (n = 798) | P |
|---|---|---|---|
| Late lumen loss - mm | 1.160.82 | 1.240.86 | 0.07 |
| Loss index | 0.530.38 | 0.590.45 | 0.009 |
| Diameter stenosis - % | 41.826.2 | 45.228.7 | 0.015 |
| Restenosis rate - % | 30.2 | 35.6 | 0.024 |

Data are proportions or meanSD

Of note, loss index which reflects the hyperplastic response after stenting was significantly lower in patients who carried the IL-1RN*2 allele. The incidence of angiographic restenosis was also significantly lower in carriers of the IL-1RN*2 allele, with 30.2% vs. 35.6% in patients of the IL-1RN 1/1 genotype. Thus, the presence of the IL-1RN*2 allele was associated with a 22% decrease in restenosis rate (odds ratio, 0.78 [0.63-0.97]). Clinical restenosis expressed as the need for target vessel revascularization was also significantly lower, with 17.7% in IL-1RN*2 allele carriers vs. 22.7% in homozygous patients for the IL-1RN*1 allele (P=0.026), yielding an odds ratio of 0.73 (0.58-0.92).

Age, gender, the presence or absence of diabetes, smoking habit, reduced left ventricular function and restenotic lesions, vessel size (all variables differing in univariate analysis by a P-value 0.30) were entered into the multivariate model for angiographic restenosis along with the presence or absence of the IL-1RN*2 allele. Older age (P=0.005), the presence of diabetes (P<0.001), restenotic lesion (P<0.001) and small vessel size (P<0.001) were independently correlated with an increased risk of restenosis. On the opposite, the presence of the IL-1RN*2 allele was independently (P<0.001) correlated with a decreased risk for restenosis with an adjusted odds ratio of 0.81 (0.71-0.92). In addition, there was a significant interaction between the presence of the IL-1RN*2 allele and age (P=0.009) as reflected by a progressively stronger protective effect of this allele in younger patients.

The results of the analysis in the prespecified subgroup of patients <60 years (n=696) are presented in Table 5. During the 1-year follow-up period, 17.1% of the IL-1RN*2 allele carriers and 24.9% of the homozygous IL-1RN*1 allele carriers needed target vessel revascularization (P=0.013). Thus, the presence of the IL-1RN*2 allele was associated with a 37% reduction (odds ratio: 0.63 [0.43-0.91]) of the need of ischemia-driven reinterventions. Quantitative angiographic data obtained for the control study at 6 months (performed in 590 or 85% of patients <60 years) are displayed in Table 5.

TABLE 5

Results at follow-up angiography in patients <60 years.

| | IL-1RN 1/2 or 2/2 (n = 273) | IL-1RN 1/1 (n = 317) | P |
|---|---|---|---|
| Late lumen loss - mm | 1.080.77 | 1.270.93 | 0.008 |
| Loss index | 0.490.35 | 0.590.48 | 0.003 |
| Diameter stenosis - % | 39.324.1 | 46.730.5 | 0.001 |
| Restenosis rate - % | 25.6 | 38.5 | <0.001 |

Data are proportions or meanSD

The incidence of angiographic restenosis was 25.6% in the combined group of IL-1RN 1/2 and IL-1RN 2/2 patients and 38.5% among IL-1RN 1/1 patients (P<0.001), which corresponds to a 45% reduction (odds ratio: 0.55 [0.39-0.78]). The incidence of restenosis decreased progressively with heterozygosity and homozygosity for the IL-1RN*2 allele. The rate of angiographic restenosis was 38.5% in IL-1RN 1/1 patients, 26.3% in IL-1RN 1/2 patients and 22.4% in IL-1RN 2/2 patients (P=0.001, test for trend). The target vessel revascularization rate was 24.9% in IL-1RN 1/1 patients, 17.9% in IL-1RN 1/2 patients and 13.2% in IL-1RN 2/2 patients (P=0.01, test for trend).

Example 7

Association of Composite IL-1 Genotypes with Predisposition to Cardiovascular Disease A study was performed that correlated IL-1 composite genotypes with the expression of inflammatory mediators and the risk for adverse cardiac events. Identified are composite genotypes and their relationship to risk of increased or, conversely, decreased, predisposition to cardiovascular disease. Also identified are the genotype prevalences in the ethnic populations. The IL-1 gene cluster composite genotypes are useful to differentiate an individual's expression of inflammatory factors in the presence of environmental challenges, such as LDL ("bad") cholesterol, thereby assisting healthy individuals by identifying a genetic risk for heart disease and allowing the making of personalized health decisions (such as nutrition and lifestyle) to preserve heart health.

Data were obtained from clinical studies that evaluated the association between IL-1 gene cluster genetic variations and biochemical or clinical outcomes, and the data support the impact of IL-1 genetic variations on biological/molecular mechanisms, disease/clinical outcome associations, and responses to anti-inflammatory supplementation as measured by biomarker changes or disease risk.

Table 7-1 provides the predominant IL-1 haplotypes in Caucasian and Asian (here, Korean) populations.

The data provided in Table 7-2 demonstrate that individuals with one of three different composite genotype patterns will be classified as IL-1 genotype "positive" for over-expression of inflammation and increased risk of CVD, while individuals with one of two different composite genotype patterns will be classified as IL-1 genotype "negative" for over-expression of inflammation and decreased risk of CVD.

Table 7-3 provides the prevalence of the risk patterns shown in Table 7-2 by ethnicity.

TABLE 7-1

Predominant IL-1 Haplotypes

| | | Gene | | | | |
|---|---|---|---|---|---|---|
| Hap- | IL-A | IL-1B | | | Caucasian | Korean Fre- |
| lo- | | SNP Locus | | | | |
| type | +4845 | +3954 | +3877 | −511 | −1464 | Frequency | quency |
| 1 | 1 | 1 | 2 | 1 | 1 | 31.1 | 39.6 |
| 2 | 1 | 1 | 1 | 2 | 2 | 21.7 | 23.6 |
| 3 | 2 | 2 | 1 | 1 | 1 | 16.5 | 3.3 |
| 4 | 1 | 1 | 2 | 2 | 2 | 1.4 | 15.8 |
| 5 | 1 | 1 | 1 | 1 | 1 | 12.7 | 4.8 |
| 6 | 1 | 1 | 1 | 2 | 1 | 4.1 | 4.1 |
| 7 | 2 | 1 | 1 | 2 | 1 | 2.4 | 1.5 |
| 8 | 2 | 1 | 1 | 2 | 1 | 1.6 | 2.4 |
| 9 | 2 | 1 | 2 | 1 | 1 | 2.6 | 0.5 |
| 10 | 1 | 2 | 1 | 1 | 1 | 2.3 | 0 |
| 11 | 1 | 1 | 2 | 2 | 1 | 0 | 2.8 |
| 12 | 2 | 2 | 1 | 2 | 2 | 1.8 | 0 |
| 13 | 2 | 1 | 1 | 1 | 1 | 0.6 | 0.7 |
| | | | | | | 98.80% | 99.10% |

TABLE 7-2

IL-1 Composite Genotypes that are Associated with
increased or decreased CVD Risk:

| | Gene | | | | | |
|---|---|---|---|---|---|---|
| | IL-A | IL-1B | | | Test | |
| | SNP Locus | | | | | |
| | +4845 | +3954 | +3877 | −511 | Result | Additional information |

Risk Patterns

| | +4845 | +3954 | +3877 | −511 | Result | Additional information |
|---|---|---|---|---|---|---|
| 1a | 2* | 2* | 1.1 | 1.1 | Positive | Increased risk for CVD and first heart attack |
|  | 1.1 | 1.1 | 1.1 | 1.1 | Positive | at younger age in combination with increased expression of IL-1β and CRP biomarkers. |
| 1b | 1.1 | 2* | 2* | 1.1 | Positive | Increased risk for CVD and first heart attack |
|  | 2* | 1.1 | 2* | 1.1 | Positive | at younger age in combination with |
|  | 1.1 | 1.1 | 2* | 1.1 | Positive | increased expression of IL-1β biomarker. |
| 1c | 2* | 2* | 1.1 | 1.2 | Positive | Increased risk for CVD and first heart attack |
|  | 2* | 1.1 | 1.1 | 1.2 | Positive | at younger age in combination with |
|  | 1.1 | 2* | 1.1 | 1.2 | Positive | increased expression of CRP biomarker. |
|  | 1.1 | 1.1 | 1.1 | 1.2 | Positive Negative | |

Non-Risk Patterns

| | +4845 | +3954 | +3877 | −511 | Result | Additional information |
|---|---|---|---|---|---|---|
| 1c' | 2* | 1.1 | 2* | 1.2 | Negative | Decreased risk for CVD and first heart |
|  | 1.1 | 2* | 2* | 1.2 | Negative | attack at younger age. |
|  | 1.1 | 1.1 | 2* | 1.2 | Negative | |
| 1d | 2* | 2* | 1.1 | 2.2 | Negative | Decreased risk for CVD and first heart |
|  | 1.1 | 2* | * | 2.2 | Negative | attack at younger age. |
|  | 2* | 1.1 | * | 2.2 | Negative | |
|  | 1.1 | 1.1 | * | 2.2 | Negative | |

"*" indicates that only one allele is required to be present for this genotype.

TABLE 7-3

Prevalence of the Risk Patterns by Ethnicity

| Pattern | Caucasian | Japanese | Chinese | Korean | Black |
|---|---|---|---|---|---|
| Increased risk | | | | | |
| 1a | 21% | 5% | 2% | 2% | 5% |
| 1b | 23.5% | 30% | 26% | 19% | 15% |
| 1c | 14.5% | 3% | 1% | 4% | 8% |
| Pattern 1 "At Increased Risk" Totals | 59% | 38% | 29% | 25% | 28% |
| Decreased risk | 40.5% | 62% | 72% | 75% | 72% |
| Totals | 99.5% | 100% | 101% | 100% | 100% |

Association of Increased Inflammatory Mediators with Composite Genotype Patterns Associated with Increased Risk of Cardiovascular Disease.

A DARIC (dental atherosclerotic risk in communities) study was performed to demonstrate the correlation between increased risk for CVD and first heart attack at younger age and increased expression of IL-1β and CRP biomarkers.

Composite genotype 1a patterns were associated with a 32% increase of GCF IL-1β (p=0.01) and a 24% increase of CRP in serum (p=0.087).

Composite genotype 1b patterns were associated with a 28% increase of GCF IL-1β (p=0.02) but were not significantly associated with increased levels of CRP in serum.

Composite genotype 1c patterns were not significantly associated with increased levels of GCF IL-1β but were associated with a 54% increase of CRP in serum (p=0.01).

Another study generated similar results, showing that pattern 1a is associated with an 81% increase of CRP in serum (p=0.0001), pattern 1b is not significantly associated with increased CRP in serum, and pattern 1c associated with a 32% increase of CRP in serum (p=0.04).

Additional studies relating to IL-1 gene variations and inflammatory mediators are described in Table 7-4.

TABLE 7-4

Summary of IL-1 Gene Variations and Inflammatory Mediators

| Mediator | Mediator Source | Disease exposure (note 1) | IL-1 polymorphisms associated with elevated mediator levels | Reference | Comments |
|---|---|---|---|---|---|
| IL-1β protein Association | PBMCs (note 2) | None | IL-1B −511 1* | Iacoviello (1) | LPS stimulated Results: 1.1 = 4500 pg/ml 1.2 = 2100 pg/ml 2.2 = 800 pg/ml |
| Non-Association | PBMCs | None | IL-1B −511 2* | Hall 2004 (2) | Due to the complicated in vitro design it is unclear what it was really being measured so this article is noted but the data not useful. |
| CRP Association | Serum | Coronary Heart Disease | IL-1B +3954 2* IL-1A +4845 2* | Berger 2002 (3) | Single SNP analysis as opposed to composite genotype-components consistent with 1a and 1c. |
| | Serum | None | IL-1B −511 1* IL-1B +3954 2* | Eklund 2003 (4) | Single SNP analysis as opposed to composite genotype |
| | Serum | Coronary Heart Disease | IL-1B +3954 2* | Latkovskis (5) | Single SNP analysis as opposed to composite genotype |

Note 1. Subjects in the study had the listed condition
Note 2. PMBCs are peripheral blood mononuclear cells
References for Table 7-4.
(1) Iacoviello et al. Arterioscler Thromb Vasc Biol 2005; 25: 222-227.
(2) Hall et al. Arthritis Rheum 2004; 50(6): 1976-1983.
(3) Berger et al. Cytokine. 2002; 17:171-174.
(4) Eklund et al. Eur Cytokine Netw 2003 July-September; 14(3): 168-171.
(5) Latkovskis et al. Eur J Immunogenet 2004; 31 (5): 207-213.

Of particular interest is the Iacoviello study, that demonstrated that the IL-1B (−511) 1.1 genotype is associated with increased risk for MI at younger age (for males <45 yrs and for females <50 yrs. (OR-2.2)). Further, the IL-1B (−511) 1.2 genotype is associated with increased risk for MI at younger age (for males <45 yrs and for females <50 yrs. (OR=1.8)).

Also of interest is a study performed with the Mayo clinic, which found that individuals with coronary artery disease were at greater risk for MI than those without disease, that those patients with multi-vessel disease (MVD) were at greater risk for MI than those with single vessel disease (SVD), and that, independent of the extent of coronary artery disease, those individuals positive for the CVD genotype at IL-1A +4845 and IL-1B+3954 (consistent with patterns 1a and 1c) were at added risk for MI than those who tested negative. The Mayo study also found that positive CVD genotypes at IL-1A (+4845) and IL-1B (+3954) (consistent with patterns 1a and 1c) were also significantly associated with a younger age at time of cardiac catheterization (2 years younger) and at time of presenting with typical and atypical chest pain (2 years younger). Finally, this study found that in individuals with coronary artery disease who tested positive for the CVD test (i.e., risk patterns 1a, 1b or 1c), there was a significant association with an increased risk for a documented prior heart attack.

The association of the CVD patterns with myocardial infarction was also determined, and provided below in Table 7-5.

TABLE 7-5

CVD Pattern 1 Association with Heart Attack

| Pattern 1 "at risk" genotypes | P-value | Odds ratio |
|---|---|---|
| 1a | 0.01 | 4.3 |
| 1b | 0.02 | 4.1 |
| 1c | 0.003 | 7.0 |

Example 8

Association of Composite IL-1 Genotypes with Predisposition to Cardiovascular Disease in Korean Men A study was performed that correlated IL-1 composite genotypes present in Korean men with the expression of inflammatory mediators and the risk for adverse cardiac events. Identified was a new genetic marker, the IL-1B (+3877) allele, and a composite genotype containing two copies of the IL-1B (+3877) allele 1, one copy of the IL-1B (−511) allele 1, and one copy of the IL-1B (−511) allele 2. Table 8-1 shows the pattern of IL-1 genotypes linked to CVD and the association of these alleles with other IL-1 gene cluster alleles.

TABLE 8-1

| Pattern | LD Block 1 (1) | LD Block 2 (2) |
|---|---|---|
| 1a | + | 1.1 |
| 1b | − | 1.1 |
| 1c | + | 1.2 |
| 1c' | − | 1.2 |
| 1d | + | 1.2 |
| Reference | − | 2.2 |

(1) Markers in Caucasians include IL-1A(+4845) allele 2 plus IL-1B(+3954) allele2; markers in Asians (e.g., Koreans) include IL-1B(+3877) 1.1.
(2) Markers of functional haplotypes in the IL-1B promoter, including IL-1B(−511)

A study was performed comparing Caucasian and Korean male subjects. The sample population was as follows: n=133 subjects that were CAD+ with MI (most ≦55 yrs), n=169 CAD+ without MI (most ≦55 yrs), and n=302 controls. The mean age was 54 yrs. C-reactive protein (CRP) measurements were as follows. The tertiles were distributed as follows: <0.37; 0.37-1.08; >1.08 mg/l. A CRP ≧3 mg/l was found in 12% of cohort.

CRP levels were associated with genotypes associated with CVD, as shown in Table 8-2. As in Table 8-1, markers in Caucasians include IL-1A (+4845) allele 2 plus IL-1B (+3954) allele2; markers in Asians (e.g., Koreans) include IL-1B (+3877) 1.1. Markers of functional haplotypes in the IL-1B promoter, include IL-1B (−511).

TABLE 8-2

| Pattern | LD Block 1 (1) | LD Block 2 (2) | Caucasian phenotype (risk of CVD) | Korean phenotype (risk of CVD) |
|---|---|---|---|---|
| 1a | + | 1.1 | Increased | (uncommon genotype) |
| 1b | − | 1.1 | | |
| 1c | + | 1.2 | Increased | Increased |
| 1c' | − | 1.2 | | |
| 1d | + | 1.2 | (uncommon genotype) | Increased |
| Reference | − | 2.2 | | |

The relative distribution of CVD-associated genotypes is provided in Table 8-3. As in Table 8-1, markers in Caucasians include IL-1A (+4845) allele 2 plus IL-1B (+3954) allele2; markers in Asians (e.g., Koreans) include IL-1B (+3877) 1.1.

TABLE 8-3

| Pattern | LD Block 1 | LD Block 2 | % of Caucasian subjects | Caucasian phenotype | % of Korean subjects | Korean phenotype |
|---|---|---|---|---|---|---|
| 1a | + | (−511) 1.1 | 21 | Early MI, CAD (1) | 1 | |
| 1b | − | (−511) 1.1 | 23.5 | Early MI, CAD (1) | 20 | Early MI vs CAD |
| 1c | + | (−511) 1.2 | 14.5 | Early MI | 7 | Early MI vs CAD; early MI vs. Controls |
| 1c' | − | (−511) 1.2 | 30 | Early MI | 50 | Early MI |
| 1d | + | (−511) 1.2 | 1 | | 10 | Early MI vs CAD; early MI vs. Controls |
| Reference | − | (−511) 2.2 | 10 | Reference group (2) | 12 | Reference group |

(1) indicates the increased risk of coronary artery disease in presence of a challenge such as oxPL;
(2) indicates the increased risk of coronary artery disease in absence of a challenge such as oxPL.

In this study, subjects having myocardial infarction (MI) were compared to control subjects. There were 133 CAD+ MI+ and 302 controls; the data were adjusted for age, BMI, and smoking. It was determined that a genotype pattern indicative of a risk of MI contains two copies of IL-1B (−511) allele 2 and two copies of IL-1B (+3877) allele 1 (pattern 1d; p=0.01). Another genotype pattern indicative of a risk of MI contains an IL-1B (−511) allele 1, an IL-1B (−511) allele 2 and two copies of IL-1B (+3877) allele 1 (pattern 1c; p=0.09).

In further analysis, younger (55 years or less) subjects having MI were compared to older (56 years or older) controls. There were 97 CAD+MI+subjects with an onset ≦55 yrs, and 132 controls, age 56 yrs or older. Data were adjusted for BMI and smoking. It was determined that a genotype pattern indicative of a risk of MI contains two copies of IL-1B (−511) allele 2 and two copies of IL-1B (+3877) allele 1 (pattern 1d; p=0.01). Another genotype pattern indicative of a risk of MI contains an IL-1B (−511) allele 1, an IL-1B (−511) allele 2 and two copies of IL-1B (+3877) allele 1 (pattern 1c; p=0.05).

Additionally, subjects having an MI were compared with non-MI controls. There were 133 MI positive subjects and 169 MI negative subjects. Generally, MI negative subjects were older, lighter, and had a higher alcohol intake. Data were adjusted for age, BMI, smoking, and medications that treat serum lipid levels. It was determined that a genotype pattern indicative of a risk of MI contains two copies of IL-1B (−511) allele 1 and an IL-1B (+3877) allele 2 (pattern 1b; p=0.15). Another genotype pattern indicative of a risk of MI contains an IL-1B (−511) allele 1, an IL-1B (−511) allele 2 and two copies of IL-1B (+3877) allele 1 (pattern 1c; p=0.02). Another genotype pattern indicative of a risk of MI contains two copies of IL-1B (−511) allele 2 and two copies of IL-1B (+3877) allele 1 (pattern 1d; p=0.02).

In further analysis, subjects aged 55 years or younger having CAD and MI were compared to controls having CAD without MI. There were 77 MI+ subjects and 79 MI− subjects. MI negative subjects tended to be older, lighter, and had a higher alcohol intake. Data were adjusted for BMI, smoking, and HDL content. It was determined that a genotype pattern indicative of a risk of MI contains two copies of IL-1B (−511) allele 1 and an IL-1B (+3877) allele 2 (pattern 1b; p=0.04). Another genotype pattern indicative of a risk of MI contains an IL-1B (−511) allele 1, an IL-1B (−511) allele 2 and two copies of IL-1B (+3877) allele 1 (pattern 1c; p=0.01). Another genotype pattern indicative of a risk of MI contains two copies of IL-1B (−511) allele 2 and two copies of IL-1B (+3877) allele 1 (pattern 1d; p=0.02).

Another aspect of the study compared HDL levels and risk of MI. There were 156 subjects having CAD aged 55 yrs or less. It was determined that in subjects having an HDL ≦40 mg/dl, there was no associated IL-1 risk of MI. For subjects having an HDL >40 mg/dl (n=95), the following MI risk patterns were observed. Pattern 1b (p=0.05); pattern 1c (p=0.04) and pattern 1d (p=0.02).

Further, CRP levels were determined in healthy control subjects. 302 subjects having a mean age of 54 yrs were analyzed. CRP tertiles were as follows: <0.37; 0.37-1.08; >1.08 mg/l. It was found that 12% of the cohort had CRP levels ≧3 mg/l. A genotype containing two copies of the IL-1B (+3877) allele 1 were associated with a 40% increase in CRP (p=0.03). This result was confirmed with all genotype combinations of IL-1B (−511).

What is claimed is:

1. A method for determining a human male subject's predisposition to increased risk for myocardial infarction at or before the age of 55, comprising detecting an allelic pattern of two copies of IL-1B (−511) allele 1, an IL-1B (+3954) allele 2, and an IL-1A (+4845) allele 2; wherein the presence of said pattern indicates that said subject is predisposed to myocardial infarction at or before the age of 55.

2. The method of claim 1, wherein said subject has increased expression of IL-1β and C-reactive protein.

* * * * *

SEQUENCE LISTING

<160> NUMBER OF SEQ ID NOS: 18

<210> SEQ ID NO 1
<211> LENGTH: 17
<212> TYPE: DNA
<213> ORGANISM: Artificial
<220> FEATURE:
<223> OTHER INFORMATION: Primer

<400> SEQUENCE: 1
ctcagcaaca ctcctat                                                17

<210> SEQ ID NO 2
<211> LENGTH: 17
<212> TYPE: DNA
<213> ORGANISM: Artificial
<220> FEATURE:
<223> OTHER INFORMATION: Primer

<400> SEQUENCE: 2
tcctggtctg caggtaa                                                17

<210> SEQ ID NO 3
<211> LENGTH: 27
<212> TYPE: DNA
<213> ORGANISM: Artificial
<220> FEATURE:
<223> OTHER INFORMATION: Primer

<400> SEQUENCE: 3
ctatctgagg aacaaccaac tagtagc                                     27

<210> SEQ ID NO 4
<211> LENGTH: 24
<212> TYPE: DNA
<213> ORGANISM: Artificial
<220> FEATURE:
<223> OTHER INFORMATION: Primer

<400> SEQUENCE: 4
taggacattg cacctagggt ttgt                                        24

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
tggcattgat ctggttcatc                                             20

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
gtttaggaat cttcccactt                                             20

```
<210> SEQ ID NO 7
<211> LENGTH: 25
<212> TYPE: DNA
<213> ORGANISM: Artificial
<220> FEATURE:
<223> OTHER INFORMATION: Primer

<400> SEQUENCE: 7
ctcaggtgtc ctcgaagaaa tcaaa                                          25

<210> SEQ ID NO 8
<211> LENGTH: 21
<212> TYPE: DNA
<213> ORGANISM: Artificial
<220> FEATURE:
<223> OTHER INFORMATION: Primer

<400> SEQUENCE: 8
gcttttttgc tgtgagtccc g                                              21

<210> SEQ ID NO 9
<211> LENGTH: 30
<212> TYPE: DNA
<213> ORGANISM: Artificial
<220> FEATURE:
<223> OTHER INFORMATION: Primer

<400> SEQUENCE: 9
atggttttag aaatcatcaa gcctagggca                                     30

<210> SEQ ID NO 10
<211> LENGTH: 30
<212> TYPE: DNA
<213> ORGANISM: Artificial
<220> FEATURE:
<223> OTHER INFORMATION: Primer

<400> SEQUENCE: 10
aatgaaagga ggggaggatg acagaaatgt                                     30

<210> SEQ ID NO 11
<211> LENGTH: 28
<212> TYPE: DNA
<213> ORGANISM: Artificial
<220> FEATURE:
<223> OTHER INFORMATION: Primer

<400> SEQUENCE: 11
gggatgttaa ccagaagacc ttctatct                                       28

<210> SEQ ID NO 12
<211> LENGTH: 27
<212> TYPE: DNA
<213> ORGANISM: Artificial
<220> FEATURE:
<223> OTHER INFORMATION: Primer

<400> SEQUENCE: 12
caaccactca ccttctaaat tgacatt                                        27

<210> SEQ ID NO 13
<211> LENGTH: 30
<212> TYPE: DNA
<213> ORGANISM: Artificial
<220> FEATURE:
<223> OTHER INFORMATION: Primer
```

```
<400> SEQUENCE: 13
aacaaccaac tagttgctgg atacttgcaa                                      30

<210> SEQ ID NO 14
<211> LENGTH: 25
<212> TYPE: DNA
<213> ORGANISM: Artificial
<220> FEATURE:
<223> OTHER INFORMATION: Primer

<400> SEQUENCE: 14
tgtacctaag cccacccttt agagc                                           25

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
tggcctccag aaacctccaa                                                 20

<210> SEQ ID NO 16
<211> LENGTH: 20
<212> TYPE: DNA
<213> ORGANISM: Artificial
<220> FEATURE:
<223> OTHER INFORMATION: Primer

<400> SEQUENCE: 16
gctgatattc tggtgggaaa                                                 20

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
ggcaagagca aaactctgtc                                                 20

<210> SEQ ID NO 18
<211> LENGTH: 27
<212> TYPE: DNA
<213> ORGANISM: Artificial
<220> FEATURE:
<223> OTHER INFORMATION: Primer

<400> SEQUENCE: 18
acaaccaact agttgccgga tacttgc                                         27
```